US006433145B1

(12) United States Patent
LaFleur et al.

(10) Patent No.: US 6,433,145 B1
(45) Date of Patent: Aug. 13, 2002

(54) KERATINOCYTE DERIVED INTERFERON

(75) Inventors: David W. LaFleur, Washington, DC (US); Paul A. Moore, Germantown; Steven M. Ruben, Olney, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/487,792

(22) Filed: Jan. 20, 2000

Related U.S. Application Data

(63) Continuation-in-part of application No. 09/358,587, filed on Jul. 21, 1999, now abandoned, and a continuation-in-part of application No. PCT/US99/16424, filed on Jul. 21, 1999.
(60) Provisional application No. 60/093,643.

(51) Int. Cl.$^7$ .................. C07K 17/00; C07K 14/00; A61K 38/21; C12Q 1/68

(52) U.S. Cl. .................. 530/351; 530/350; 424/85.4; 435/7.1

(58) Field of Search .................. 536/23.5, 23.52; 530/350, 351, 387.1; 435/69.1, 7.1; 424/85.4

(56) References Cited

U.S. PATENT DOCUMENTS 5,710,027 A 1/1998 Hauptmann et al.

FOREIGN PATENT DOCUMENTS

| WO | WO 00/05731 | 2/2000 |
|----|-------------|--------|
| WO | WO 01/42474 | 6/2001 |
| WO | WO 01/61009 | 8/2001 |

OTHER PUBLICATIONS

Mikayama et al. Moleuclar cloning and functional expression of a cDNA encoding glycosylation–inhibiting factor. 1993, Proc Natl Acad Sci USA. vol.90, pp. 10056–10060.*
Voet et al. Biochemistry, John Wiley & Sons, Inc. pp. 126–128, and 228–234.*
Genbank Accession No: AAF67468 (May 4, 2000).
LaFleur et al., "Interferonκ, a Novel Type 1 Interferon Expressed in Human Keratinocytes," J. Biol. Chem., 276(43):39765–39771 (Oct. 26, 2001).
Genbank Accession No. AF146759, Cao et al. (May 4, 2000).
GeneSeq Accession No. AAH75966, Shanghai Hauchen Biolog. Tech., Chinese Appl. No. CN 1299831 (Jun. 20, 2001).
GeneSeq Accession No. AAG66451, Cao et al. (Jun. 20, 2001).
GeneSeq Accession No. AAG66452, Cao et al. (Jun. 20, 2001).
Der et al., Proc. Natl. Acad. Sci., vol. 95:15623–15628 (1998).
Karpusas et al., Natl. Acad. Sci., vol. 94:11813–11818 (1997).
Whaley et al., J. Biol. Chem., vol. 269(14):10864–10868 (1994) abstract only.
Stark et al., Annu. Rev. Biochem., vol. 67:227–64 (1998) abstract only.
Genbank Accession No: AAA31503 (Mar. 23, 1999).
Genbank Accession No: CAA46506 (May 8, 1992).
Genbank Accession No: AAA72588 (Apr. 27, 1993).
Genbank Accession No: CAA01011 (Dec. 1, 1993).
Genbank Accession No: AAA36040 (Apr. 27, 1993).
Genbank Accession No: CAA00839 (Dec. 3, 1993).
Genbank Accession No: CAA24980 (Sep. 12, 1993).
Genbank Accession No: CAA24970 (Sep. 12, 1993).
Genbank Accession No: AAA52724 (Nov. 8, 1994).
Genbank Accession No: CAA23812 (Sep. 12, 1993).
Genbank Accession No: AAA36123 (May 4, 1994).
Genbank Accession No: AAA30580 (Apr. 27, 1993).
Genbank Accession No: AAA30579 (Apr. 27, 1993).
Genbank Accession No: AI155872 (Sep. 30, 1998).
International Search Report (PCT/US99/16424).
Danilkovitch et al., Hybridoma, vol. 16(1):69–75 (1997).
Danilkovitch et al., Immunology Letters, vol. 31:15–20 (1991).
Pontzer et al., J. of Interferon Res., vol. 14:133–141 (1994).
Protzer et al., Proc. Natl. Acad. Sci., vol. 96:10818–10823 (1999).
Genbank Accession No: CAA00963 (Dec. 1, 1993).
Genbank Accession No: AAA70091 (Jul. 19, 1995).
Genbank Accession No: CAA00397 (Jul. 12, 1993).
Genbank Accession No: CAA00399 (Jul. 12, 1993).
Genbank Accession No: CAA00401 (Jul. 12, 1993).
Geneseq Accession No: P70330 (May 20, 1991).
Geneseq Accession No: Y25093 (Aug. 24, 1999).
Geneseq Accession No: W70811 (Feb. 4, 1999).
Geneseq Accession No: W09278 (Apr. 8, 1997).
Geneseq Accession No: R99398 (Dec. 29, 1996).
Geneseq Accession No: W44117 (Jun. 16, 1998).
Geneseq Accession No: W31699 (Apr. 14, 1998).
Geneseq Accession No: W44111 (Jun. 16, 1998).
Genbank Accession No: CAA80408 (Nov. 3, 1993).
Yaar et al., The Journal of Cell Biol., vol. 103:1349–1354 (1986).
Dixon et al., Mol. Biol. Med., vol. 2(1):37–51 (1984).
Schwarz et al., Journal Immunol., vol. 138(5):1457–63 (1987).
Yaar et al., Ann N Y Acad Sci., vol. 548:299–311 (1988).
Eckert et al., Environ Health Perspect., vol. 80:109–16 (1989).

* cited by examiner

*Primary Examiner*—Jeffrey Stucker
*Assistant Examiner*—Jegatheesan Seharaseyon
(74) *Attorney, Agent, or Firm*—Human Genome Sciences, Inc.

(57) ABSTRACT

The present invention relates to a novel KDI protein which is a member of the interferon family. In particular, isolated nucleic acid molecules are provided encoding a human interferon polypeptide, called "KDI". KDI polypeptides are also provided as are vectors, host cells and recombinant methods for producing the same. The invention further relates to screening methods for identifying agonists and antagonists of KDI activity. Also provided are therapeutic methods for treating immune system-related disorders.

92 Claims, 9 Drawing Sheets

Keratinocyte Derived Interferon

```
  1 CCA CGC GTC CGG GAT TTT TTA GCT TGC AAA AAA AAT GAG CAC CAA ACC TGA TAT GAT TCA  60
  1                                                   M   S   T   K   P   D   M   I   Q   9

61 AAA GTG TTT GTG GCT TGA GAT CCT TAT GGG TAT ATT CAT TGC TGG CAC CCT ATC CCT GGA 120
 10  K   C   L   W   L   E   I   L   M   G   I   F   I   A   G   T   L   S   L   D  29

121 CTG TAA CTT ACT GAA CGT TCA CCT GAG AAG AGT CAC CTG GCA AAA TCT GAG ACA TCT GAG 180
 30  C   N   L   N   V   H   L   R   R   V   T   W   Q   N   L   R   H   L   S      49

181 TAG TAT GAG CAA TTC ATT TCC TGT AGA ATG TCT ACG AGA AAA CAT AGC TTT TGA GTT GCC 240
 50  S   M   S   N   S   F   P   V   E   C   L   R   E   N   I   A   F   E   L   P  69

241 CCA AGA GTT TCT GCA ATA CAC CCA ACC TAT GAA GAG GGA CAT CAA GAA GGC TTT CTA TGA 300
 70  Q   E   F   L   Q   Y   T   Q   P   M   K   R   D   I   K   K   A   F   Y   E  89

301 AAT GTC CCT ACA GGC CTT CAA CAT CTT CAG CCA ACA CAC TTT CAA ATA TTG GAA AGA GAG 360
 90  M   S   L   Q   A   F   N   I   F   S   Q   H   T   F   K   Y   W   K   E   R 109

361 ACA CCT CAA ACA AAT CCA AAT AGG ACT TGA TCA GCA AGC AGA GTA CCT GAA CCA ATG CTT 420
110  H   L   K   Q   I   Q   I   G   L   D   Q   Q   A   E   Y   L   N   Q   C   L 129

421 GGA GGA AGA CGA GAA TGA AAA TGA AGA CAT GAA AGA AAT GAA AGA GAA TGA GAT GAA ACC 480
130  E   E   D   E   N   E   N   E   D   M   K   E   M   K   E   N   E   M   K   P 149

481 CTC AGA AGC CAG GGT CCC CCA GCT GAG CAG CCT GGA ACT GAG GAG ATA TTT CCA CAG GAT 540
150  S   E   A   R   V   P   Q   L   S   S   L   E   L   R   R   Y   F   H   R   I 169

541 AGA CAA TTT CCT GAA AGA AAA GAA ATA CAG TGA CTG TGC CTG GGA GAT TGT CCG AGT GGA 600
170  D   N   F   L   K   E   K   K   Y   S   D   C   A   W   E   I   V   R   V   E 189

601 AAT CAG AAG ATG TTT GTA TTA CTT TTA CAA ATT TAC AGC TCT ATT CAG GAG GAA ATA AGA 660
190  I   R   R   C   L   Y   Y   F   Y   K   F   T   A   L   F   R   R   K   *     207

661 ATC ATC TAC CTT CAA GCA AGA ATT AAC AGA GAT TGT GGC TAC GCA AAT GCA CCA AAA AAG 720
721 GGT GAA ATA TAT CTG AAA TGT ACC TGG TTC TGC CCT TGG AAG CCA CTT CCT GCT CAT GCC 780
781 ACT AAC AGC ATG CTG CCA AAC TGT TCA GAT TCA AGA TTA TTC CAA GCG CAG GGC CCA AAT 840
841 GTT ATA GCC AAA GAA AGT CTT ATG ATA AAA GTG AGG CAA ATT TCA GCC AAG AAG TTA GAA 900
901 GAG ATG TTT AAA AGA ACA AGA ACA AAT TGT GGA TCA TGG TAT ATG CAG GCT ATC AGC AGA 960
961 AGG ATC AGA CAA TAA AAT GAG TTA GTG CAA ACC ATT AGT AAA AAA TAA CTA TCA GCA GAG 1020
1021 TTG TTC CAG ATT AAA AAT AGT ACT ACA AGC TTG TAA AGG AGT TAG GAC ATG CAA GCT ACT 1080
1081 GAG CAT AAA ATA TAT ACT TGC TAT TTT TCA TGA CTT TCT CTA ATA AAG TCT TTG ACT GTT 1140
1141 CTC TCT AAT AAA AAA AAA AAA AAA AAA AAA 1170
```

FIG. 1

```
HKAPI15    10  KCLWLEILMGIFIAG...TLSLDCNLLNVH..LRRVTWQNLRHLSSMSNS  54
               ..|::.:|  ::..:.:     .  ||:|:| . |   |.| |:  |:::..:|
INF-omega   1  MALLFPLLAALVMTSYSPVGSLGCDLPQNHGLLSRNTLVLLHQMRRIS..  48

HKAPI15    55  FPVECLRENIAFELPQEFLQYTQPMKRDIKKAFYEMSLQAFNIF.SQHTF 103
               |. ||::. .| :|||::. .|   |  .:....:.||   | |.:| .::.
INF-omega  49  .PFLCLKDRRDFRFPQEMVKGSQLQKAHVMSVLHEMLQQIFSLFHTERSS  97

HKAPI15   104  KYWKERHLKQIQIGLDQQAEYLNQCLEEDENENEDMKEMKENEMKPSEAR 153
               |.    |.|::.:|.||  :.|:  ||  :  .|.|.    .:..
INF-omega  98  AAWNMTLLDQLHTELHQQLQHLETCLLQVVGEGESAGAISS.........138

HKAPI15   154  VPQLSSLELRRYFHRIDNFLKEKKYSDCAWEIVRVEIRRCLYYFYKFTAL 203
               ..|.|||||: |  :|||||||||||:||:||.::|:.   .: .
INF-omega 139  ....PALTLRRYFQGIRVYLKEKKYSDCAWEVVRMEIMKSLFLSTNMQER 184

HKAPI15   204  FRRK 207
               :|.|
INF-omega 185  LRSK 188
```

FIG. 2

```
                    10           20           30           40
  1  C T G G A C T G T A A C T T A C T G A A C G T T C A C C T G A G A A G A G T C A   wt KDI orf
  1  C T G G A   T G   A A C   T   C T G A A C G T T C A   C T G   G       G   G T   A   s KDI orf 50           60           70           80
 41  C C T G G C A A A A T C T G A G A C A T C T G A G T A G T A T G A G C A A T T C   wt KDI orf
 41  C C T G G C A   A A   C T G   G   C A   C T G A G       T A T G A G C A A   T C   s KDI orf 90          100          110          120
 81  A T T T C C T G T A G A A T G T C T A C G A G A A A A C A T A G C T T T T G A G   wt KDI orf
 81    T T   C C   G T   G A   T G   C T   C G   G A A A A C A T   G C   T T T G A     s KDI orf 130          140          150          160
121  T T G C C C C A A G A G T T T C T G C A A T A C A C C C A A C C T A T G A A G A   wt KDI orf
121    T G C C   C A A G A   T T   C T G C A A T A C A C C C A   C C   A T G A A       s KDI orf 170          180          190          200
161  G G G A C A T C A A G A A G G C C T T C T A T G A A A T G T C C C T A C A G G C   wt KDI orf
161  G   G A   A T C A A G A A   G C   T T C T A   G A A A T G T C C C T   C A G G C   s KDI orf 210          220          230          240
201  C T T C A A C A T C T T C A G C C A A C A C A C C T T C A A A T A T T G G A A A   wt KDI orf
201    T T C A A C A T C T T C A G C C A   C A C A C C T T C A A A T A   T G G A A A   s KDI orf 250          260          270          280
241  G A G A G A C A C C T C A A A C A A A T C C A A A T A G G A C T T G A T C A G C   wt KDI orf
241  G A     G   C A C C T   A A A C A   A T C C A   A T   G G   C T   G A T C A G C   s KDI orf 290          300          310          320
281  A A G C A G A G T A C C T G A A C C A A T G C T T G G A G G A A G A C G A G A A   wt KDI orf
281  A A G C A G A   T A C C T G A A C C A   T G C   T G G A   G A A G A C G A G A A   s KDI orf 330          340          350          360
321  T G A A A A T G A A G A C A T G A A A G A A A T G A A A G A G A A T G A G A T G   wt KDI orf
321    G A A A A   G A A G A C A T G A A A G A A A T G A A A G A G A A   G A   A T G   s KDI orf 370          380          390          400
361  A A A C C C T C A G A A G C C A G G G T C C C C C A G C T G A G C A G C C T G G   wt KDI orf
361  A A A C C   T C   G A A G C     G   G T   C C   C A G C T G A G C       C T G G   s KDI orf 410          420          430          440
401  A A C T G A G G A G A T A T T T C C A C A G G A T A G A C A A T T T C C T G A A   wt KDI orf
401  A A C T G   G   G   G   T A   T T C C A C   G   A T   G A C A A   T T C C T G A A   s KDI orf 450          460          470          480
441  A G A A A A G A A A T A C A G T G A C T G T G C C T G G G A G A T T G T C C G A   wt KDI orf
441  A G A A A A G A A A T A C   T   T G A C T G   G C   T G G G A   A T   G T   C G     s KDI orf 490          500          510          520
481  G T G G A A A T C A G A A G A T G T T T G T A T T A C T T T T A C A A A T T T A   wt KDI orf
481  G T G G A A A T C   G     G   T G T   T G T A   T A C T T   T A C A A A T T   A   s KDI orf 530          540
521  C A G C T C T A T T C A G G A G G A A A                                           wt KDI orf
521  C   G C T C T   T T T C   G     G   A A A                                         s KDI orf
```

KERATINOCYTE DERIVED INTERFERON

CROSS-REFERENCE TO RELATED APPLICATIONS

This is application is a continuation-in-part of U.S. Ser. No. 09/358,587 filed Jul. 21, 1999, now abandoned, and of IPCT/US99/16424, filed Jul. 21, 1999, both of which are incorporated herein by reference in its entirety. This application also claims benefit under 35 U.S.C. section 119(e) to U.S. Provisional Application Ser. No. 60/093,643, filed July, 1998, incorporated herein by reference in its entirety.

FIELD OF THE INVENTION

The present invention relates to a novel human gene encoding a polypeptide which is a member of the interferon family. More specifically, isolated nucleic acid molecules are provided encoding a human polypeptide named "Keratinocyte Derived Interferon" or "KDI". KDI polypeptides are also provided, as are vectors, host cells and recombinant methods for producing the same. Also provided are diagnostic methods for detecting disorders related to the immune system, and therapeutic methods for treating disorders of the immune system. The invention further relates to screening methods for identifying agonists and antagonists of KDI.

BACKGROUND OF THE INVENTION

Human interferons (IFNs) are a well known family of cytokines secreted by a large variety of eukaryotic cells upon exposure to various stimuli. The interferons have been classified by their chemical and biological characteristics into five groups: IFN-alpha (leukocytes), IFN-beta (fibroblasts), IFN-gamma (lymphocytes), IFN-omega (leukocytes) and IFN-tau (trophoblasts). IFN-alpha, IFN-beta, IFN-omega and IFN-tau are known as Type I interferons; IFN-gamma is known as a Type-H or immune interferon. A single functional gene in the human genome codes for interferon omega (IFN-omega), a monomeric glycoprotein distantly related in structure to IFN-alpha and IFN-beta, but unrelated to IFN-gamma. IFN-omega is secreted by virus-infected leukocytes as a major component of human leukocyte interferon. The IFNs exhibit anti-viral, immunoregulatory, and antiproliferative activity. The clinical potential of interferons has been recognized, and will be summarized below.

The Interferons (IFNs) were initially identified by their anti-viral activity and are divided into two classes: type 1 and type II. The type I IFNs are further subdivided into three sub-groups. IFN alpha, a group of 14 individual genes with 13 functional and one pseudogene; their major site of synthesis is in leukocytes and they are 165–166 amino acids in length. IFN Beta, a group of 1 functional gene and no pseudogenes; its major site of synthesis is in viral induced fibroblasts and epithelial cells and it is 166 amino acids in length. IFN omega, a group of 7 individual genes with 1 functional and 6 pseudogenes; the functional gene is expressed upon viral induction in leukocytes. The third sub-group within the type I interferons is trophoblast interferon, IFN tau, which was originally discovered in ruminant trophoblasts and later in humans as well. Whaley et al., J. Biol. Chem. 269: 10864–8 (1994).

The structural genes for all type I IFNs are located within a 400,000 base pair region on the short arm of chromosome 9 (human). None of the genes contain an intron and the proteins encoded by the functional genes all appear to share a common receptor, the type I IFN-R composed of IFNAR1 and IFNAR2 subunits. IFNAR2 has a short, long and soluble form). While they bind the same receptor there appears to be subsequent signaling differences. In contrast to the type I IFNs there is only one member of the type II IFN, namely IFN gamma, which is encoded by a single gene (containing three introns) located on chromosome 12. The protein is produced predominantly by T lymphocytes and NK cells, is 166 amino acids in length and shows no homology to type I interferons.

A range of biological activities are associated with IFNs including antiviral, anti-proliferative and immunoregulatory activities. IFN alpha is marketed by Schering Plough (Intron; IFN alpha 2B) and Hoffman La Roche (Roferon; IFN alpha 2A). Therapeutic uses include the treatment of Hairy Cell leukemia, Chronic myelogenous leukemia, low grade non-Hodgkin lymphoma, cutaneous T cell lymphoma carcinoid tumors, renal cell carcinoma, squamous epithelial tumors of the head and neck, multiple myeloma, and malignant melanoma. With regards to viral disease, Interferon alpha has been found to aid the treatment of chronic active hepatitis, caused by either Hepatitis B or C viruses. IFN Beta has been demonstrated to have clinical benefit in the treatment of multiple sclerosis. Clinical trials with Interferon gamma have shown potential in the treatment of cutaneous and also visceral leishmanias.

Anti-viral

IFNs have been used clinically for anti-viral therapy, for example, in the treatment of AIDS (HIV infection) (Lane, Semin. Oncol. 18:46–52 (October, 1991)), viral hepatitis including chronic hepatitis B, hepatitis C (Woo, M. H. and Brunakis, T. G., Ann. Parmacother, 31:330–337 (March 1997); Gibas, A. L., Gastroenterologist, 1:129–142 (June 1993)), hepatitis D, papilloma viruses (Levine, L. A. et al., Urology 47:553–557 (April 1996)), herpes (Ho, M., Ann. Rev. Med. 38:51–59 (1987)), viral encephalitis (Wintergerst et al., Infection, 20:207–212 (July 1992)), respiratory syncytial virus, panencephalitis, mycosis fungoides and in the prophylaxis of rhinitis and respiratory infections (Ho, M., Annu. Rev. Med. 38:51–59 (1987)).

Anti-parasitic

IFNs have been suggested for anti-parasite therapy, for example, IFN-gamma for treating Cryptosporidium parvum infection (Rehg, J. E., J. Infect. Des. 5 174:229–232 (July 1996)).

Anti-bacterial

IFNs have been used clinically for anti-bacterial therapy. For example, IFN-gamma has been used in the treatment of multidrug-resistant pulmonary tuberculosis (Condos, R. et al., Lancet 349:1513–1515 (1997)).

Anti-cancer

Interferon therapy has been used in the treatment of numerous cancers (e.g., hairy cell leukemia (Hoffmann et al., Cancer Treat. Rev. 12 (Suppl. B):33–37 (December 1985)), acute myeloid leukemia (Stone, R. M. et al. Am. J. Clin. Oncol. 16:159–163 (April 1993)), osteosarcoma (Strander, H. et al., Acta Oncol. 34:877–880 (1995)), basal cell carcinoma (Dogan, B. et al., Cancer Lett. 91:215–219 (May 1995)), glioma (Fetell, M. R. et al., Cancer 65: 78–83 (January, 1990)), renal cell carcinoma (Aso, Y. et al. Prog. Clin. Biol. Res. 303:653–659 (1989)), multiple myeloma (Peest, D. et al., Br. J. Haematol. 94:425–432 (September, 1996)), melanoma (Ikic, D. et al., Int. J. Dermatol. 34:872–874 (December, 1995)), myelogenous leukemia, colorectal cancer, cutaneous T cell lymphoma, myelodysplastic syndrome, glioma, head and neck cancer, breast cancer, gastric cancer, anti-cancer vaccine therapy, and Hodgkin's disease (Rybak, M. E. et al., J. Biol. Response Mod. 9:1–4 (February, 1990)). Synergistic treatment of advanced cancer with a combination of alpha interferon and temozolomide has also been reported (Patent publication WO 9712630 to Dugan, M. H.).

Immunotherapy

IFNs have been used clinically for immunotherapy or more particularly, (1) for example, to prevent graft vs. host rejection, or to curtail the progression of autoimmune diseases, such as arthritis, multiple sclerosis, (2) or diabetes (3). IFN-beta is approved of sale in the United States for the treatment (i.e., as an immunosuppressant) of multiple sclerosis. Recently it has been reported that patients with multiple sclerosis have diminished production of type I interferons and interleukin-2 (Wandinger, K. P. et al., *J. Neurol. Sci.* 149: 87–93 (1997)). In addition, immunotherapy with recombinant IFN-alpha (in combination with recombinant human L-2) has been used successfully in lymphoma patients following autologous bone marrow or blood stem cell transplantation, that may intensify remission following translation (Nagler, A. et al., *Blood* 89: 3951–3959 (June, 1997)).

Anti-allergy

The administration of IFN-gamma has been used in the treatment of allergies in mammals (See, Patent Publication WO 8701288 to Parkin, J. M. and Pinching, A. J.). It has also recently been demonstrated that there is a reduced production of IL-12 and IL-12-dependent IFN-gamma release in patients with allergic asthma (van der Pouw Kraan, T. C. et al., *J. Immunol.* 158:5560–5565 (1997)). Thus, IFN may be useful in the treatment of allergy by inhibiting the humoral response.

Vaccine Adjuvantation

Interferons may be used as an adjuvant or coadjuvant to enhance or simulate the immune response in cases of prophylactic or therapeutic vaccination (Heath, A. W. and Playfair, J. H. L., *Vaccine* 10:427–434 (1992)), such as in anti-cancer vaccine therapy.

Miscellaneous

Interferons have been used to treat corneal haze.

Clearly, there exists a need in the art for the discovery of novel interferon proteins for numerous applications, in e.g., immunotherapy, as well as anti-viral, anti-parasitic, anti-bacterial, or anti-cancer therapies, or any medical condition or situation where increased interferon activity is desired.

SUMMARY OF THE INVENTION

The present invention provides isolated nucleic acid molecules comprising a polynucleotide encoding at least a portion of the KDI polypeptide having the complete amino acid sequence shown in SEQ ID NO:2 or the complete amino acid sequence encoded by the cDNA clone deposited as plasmid DNA as ATCC Deposit Number 203500 on Dec. 1, 1998. The nucleotide sequence determined by sequencing the deposited KDI clone (HKAPI15) which is shown in FIG. 1 (SEQ ID NO:1), contains an open reading frame encoding a full length polypeptide of 207 amino acid residues, including an initiation codon encoding an N-terminal methionine at nucleotide positions 35–37. Nucleic acid molecules of the invention include those encoding the complete amino acid sequence excepting the N-terminal methionine shown in SEQ ID NO:2, which molecules also can encode additional amino acids fused to the N-terminus of the KDI amino acid sequence.

The nucleotide sequence determined by sequencing the deposited KDI clone (HKAPI15) shown in FIG. 1 (SEQ ID NO:1) also contains an open reading frame encoding a polypeptide of 201 amino acid residues, including an initiation codon encoding an N-terminal methionine at nucleotide positions 53–55. Nucleic acid molecules of the invention include those encoding the amino acid sequence from M7-K207, excepting the N-terminal methionine shown in SEQ ID NO:2, which molecules also can encode additional amino acids fused to the N-terminus of the KDI amino acid sequence. The translation of KDI can begin at M1 or at M7. Translation from M1 or M7 in an optimal Kozak context directs expression of proteins that are potent activators of the interferon-stimulated response element (ISRE).

The encoded polypeptide has a predicted leader sequence of 27 amino acids underlined in FIG. 1; and the amino acid sequence of the predicted mature KDI protein is also shown in FIG. 1 as amino acid residues 28–207 and as residues 28–207 in SEQ ID NO:2. The encoded polypeptide also has a predicted leader sequence of 21 amino acids, from M7 to S27 shown in FIG. 1 (SEQ ID NO:2). The amino acid sequence of the predicted mature KDI protein is also shown in FIG. 1 as amino acid residues 28–207 in SEQ ID NO:2.

Thus, one aspect of the invention provides an isolated nucleic acid molecule comprising a polynucleotide comprising a nucleotide sequence selected from the group consisting of: (a) a nucleotide sequence encoding the KDI polypeptide having the complete amino acid sequence in SEQ ID NO:2; (b) a nucleotide sequence encoding the KDI polypeptide having the complete amino acid sequence in SEQ ID NO:2 excepting the N-terminal methionine (i.e., residues 2–207 of SEQ ID NO:2); (c) a nucleotide sequence encoding the mature KDI polypeptide shown as residues 28–207 in SEQ ID NO:2; (d) a nucleotide sequence encoding a KDI polypeptide shown as residues 7–207 in SEQ ID NO:2; (e) a nucleotide sequence encoding the complete polypeptide encoded by the human cDNA contained in clone HKAPI15; (f) a nucleotide sequence encoding the complete polypeptide encoded by the human cDNA contained in clone HKAPI 15 excepting the N-terminal methionine; (g) a nucleotide sequence encoding the mature polypeptide encoded by the human cDNA contained in clone HKAPI15; and (h) a nucleotide sequence complementary to any of the nucleotide sequences in (a), (b), (c), (d), (e), (f) or (g) above.

Further embodiments of the invention include isolated nucleic acid molecules that comprise a polynucleotide having a nucleotide sequence at least 80%, 85%, or 90% identical, more preferably at least 91%, 92%, 93%, and 94% and most preferably at least 95%, 96%, 97%, 98% or 99%, to any of the nucleotide sequences in (a), (b), (c), (d), (e), (f), (g) or (h), above, or a polynucleotide which hybridizes under stringent hybridization conditions to a polynucleotide in (a), (b), (c), (d), (e), (f), (g) or (h), above. This polynucleotide of the present invention,, which hybridizes under stringent conditions defined herein does not hybridize to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a KDI polypeptide having an amino acid sequence in (a), (b), (c), (d), (e), (f) or (g), above.

The present invention also relates to recombinant vectors, which include the isolated nucleic acid molecules of the present invention, to host cells containing the recombinant vectors, as well as to methods of making such vectors and host cells and for using them for production of KDI polypeptides or peptides by recombinant techniques.

The invention further provides an isolated KDI polypeptide comprising an amino acid sequence selected from the group consisting of: (a) the amino acid sequence of the full-length KDI polypeptide having the complete amino acid sequence shown in SEQ ID NO:2; (b) the amino acid sequence of the full-length KDI polypeptide having the complete amino acid sequence shown in SEQ ID NO:2 excepting the N-terminal methionine (i.e., residues 2 to 207 of SEQ ID NO:2); the amino acid sequence of the mature KDI polypeptide shown as residues 28–207 in SEQ ID NO:2; (d) the amino acid sequence shown as residues 7 to 207 of SEQ ID NO:2; (e) the full length KDI polypeptide encoded by the human cDNA contained in clone HKAPI15; (f) the full-length KDI polypeptide encoded by the human cDNA contained in clone HKAPI15 excepting the N-terminal methionine; and (g) the mature KDI polypeptide encoded by the human cDNA contained in clone HKAPI15. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e), (f) or (g) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a KDI polypeptide having an amino acid sequence described in (a), (b), (c), (d), (e), (f), or (g), above. Peptides or polypeptides having the amino acid sequence of an epitope-bearing portion of a KDI polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a KDI polypeptide having an amino acid sequence described in (a), (b), (c), (d), (e), (f) or (g) above. The invention further provides methods for isolating antibodies that bind specifically to a KDI polypeptide having an amino acid sequence as described herein. Such antibodies are useful therapeutically as described below.

The invention also provides for pharmaceutical compositions comprising KDI polypeptides which may be employed, for instance, to treat immune system-related disorders such as viral infection, parasitic infection, bacterial infection, cancer, autoimmune disease, multiple sclerosis, lymphoma and allergy. Methods of treating individuals in need of interferon polypeptides are also provided.

The invention further provides compositions comprising a KDI polynucleotide or a KDI polypeptide for administration to cells in vitro, to cells ex vivo and to cells in vivo, or to a multicellular organism. In certain particularly preferred embodiments of this aspect of the invention, the compositions comprise a KDI polynucleotide for the expression of a KDI polypeptide in a host organism for use to treat a disease. Particularly preferred in this regard is expression in a human patient for treatment of a dysfunction associated with aberrant endogenous activity of an interferon.

The present invention also provides a screening method for identifying compounds capable of enhancing or inhibiting a biological activity of the KDI polypeptide, which involves contacting a receptor which is activated by the KDI polypeptide with the candidate compound in the presence of a KDI polypeptide, assaying, for example, anti-viral activity in the presence of the candidate compound and the KDI polypeptide, and comparing the activity to a standard level of activity, the standard being assayed when contact is made between the receptor and KDI in the absence of the candidate compound. In this assay, an increase in activity over the standard indicates that the candidate compound is an agonist of KDI activity and a decrease in activity compared to the standard indicates that the compound is an antagonist of KDI activity.

KDI is expressed mainly in keratinocytes, dentritic cells, monocytes and tonsil. KDI may be present in others cell and tissue types at much lower levels. KDI expression can be regulated by double stranded RNA as well as other cytokines, such as IFN gamma and Tumor Necrosis Factor (TNF). Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the immune system, significantly higher or lower levels of KDI gene expression may be detected in certain tissues (e.g., cancerous and wounded tissues), cells or bodily fluids (e.g., serum, plasma, urine, synovial fluid or spinal fluid) taken from an individual having such a disorder, relative to a "standard" KDI gene expression level, i.e., the KDI expression level in healthy tissue from an individual not having the immune system disorder. Thus, the invention provides a diagnostic method useful during diagnosis of such a disorder, which involves: (a) assaying KDI gene expression level in cells or body fluid of an individual; (b) comparing the KDI gene expression level with a standard KDI gene expression level, whereby an increase or decrease in the assayed KDI gene expression level compared to the standard expression level is indicative of disorder in the immune system.

An additional aspect of the invention is related to a method for treating an individual in need of an increased level of interferon activity in the body comprising administering to such an individual a composition comprising a therapeutically effective amount of an isolated KDI polypeptide of the invention or an agonist thereof, or administration of DNA encoding the KDI polypeptide of the present invention.

A still further aspect of the invention is related to a method for treating an individual in need of a decreased level of interferon activity in the body comprising, administering to such an individual a composition comprising a therapeutically effective amount of a KDI antagonist. Preferred antagonists for use in the present invention are KDI-specific antibodies.

BRIEF DESCRIPTION OF THE FIGURES

FIG. 1 shows the nucleotide sequence (SEQ ID NO:1) and the deduced amino acid sequence (SEQ ID NO:2) of KDI. The predicted leader sequence located at about amino acids 1–27 is underlined.

FIG. 2 shows the regions of identity between the amino acid sequences of the KDI protein and translation product of the human mRNA for Interferon Omega (SEQ ID NO:3), determined by the computer program Bestfit (Wisconsin Sequence Analysis Package, Version 8 for Unix, Genetics Computer Group, University Research Park, 575 Science Drive, Madison, Wis. 53711).

Figure 3:
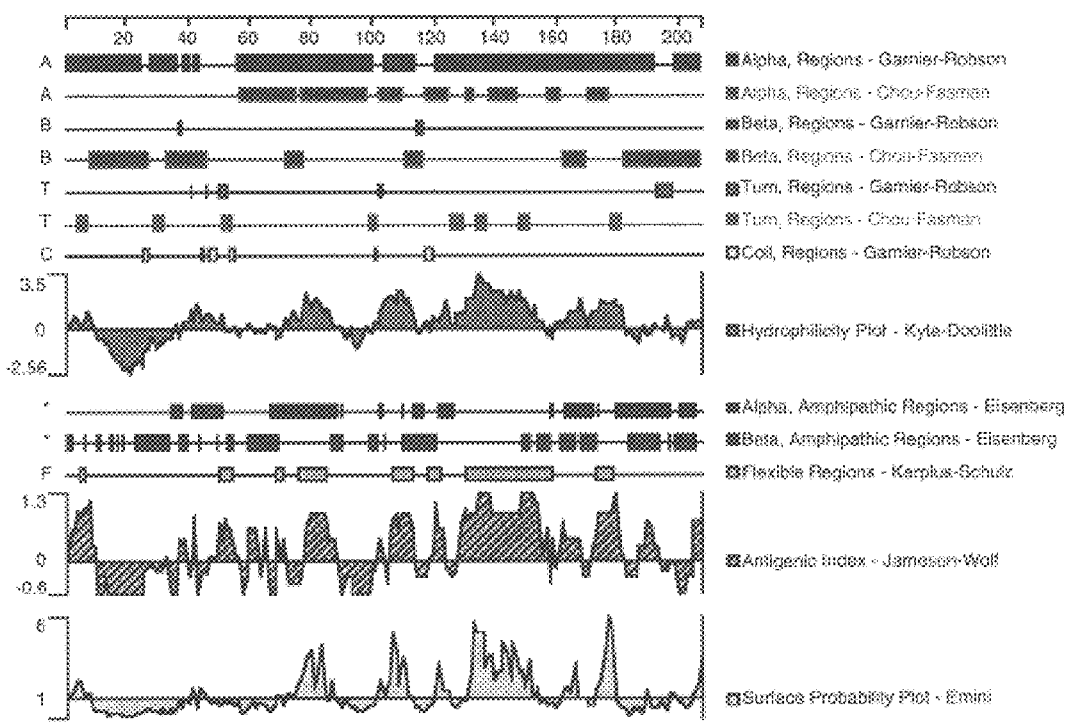
FIG. 3 shows an analysis of the KDI amino acid sequence. Alpha, beta, turn and coil regions; hydrophilicity and hydrophobicity; amphipathic regions; flexible regions; antigenic index and surface probability are shown, and all were generated using the default settings. In the "Antigenic Index—Jameson-Wolf" graph, the positive peaks indicate locations of the highly antigenic regions of the KDI protein, i.e., regions from which epitope-bearing peptides of the invention can be obtained. The domains defined by these graphs are contemplated by the present invention.
Figure 4A:
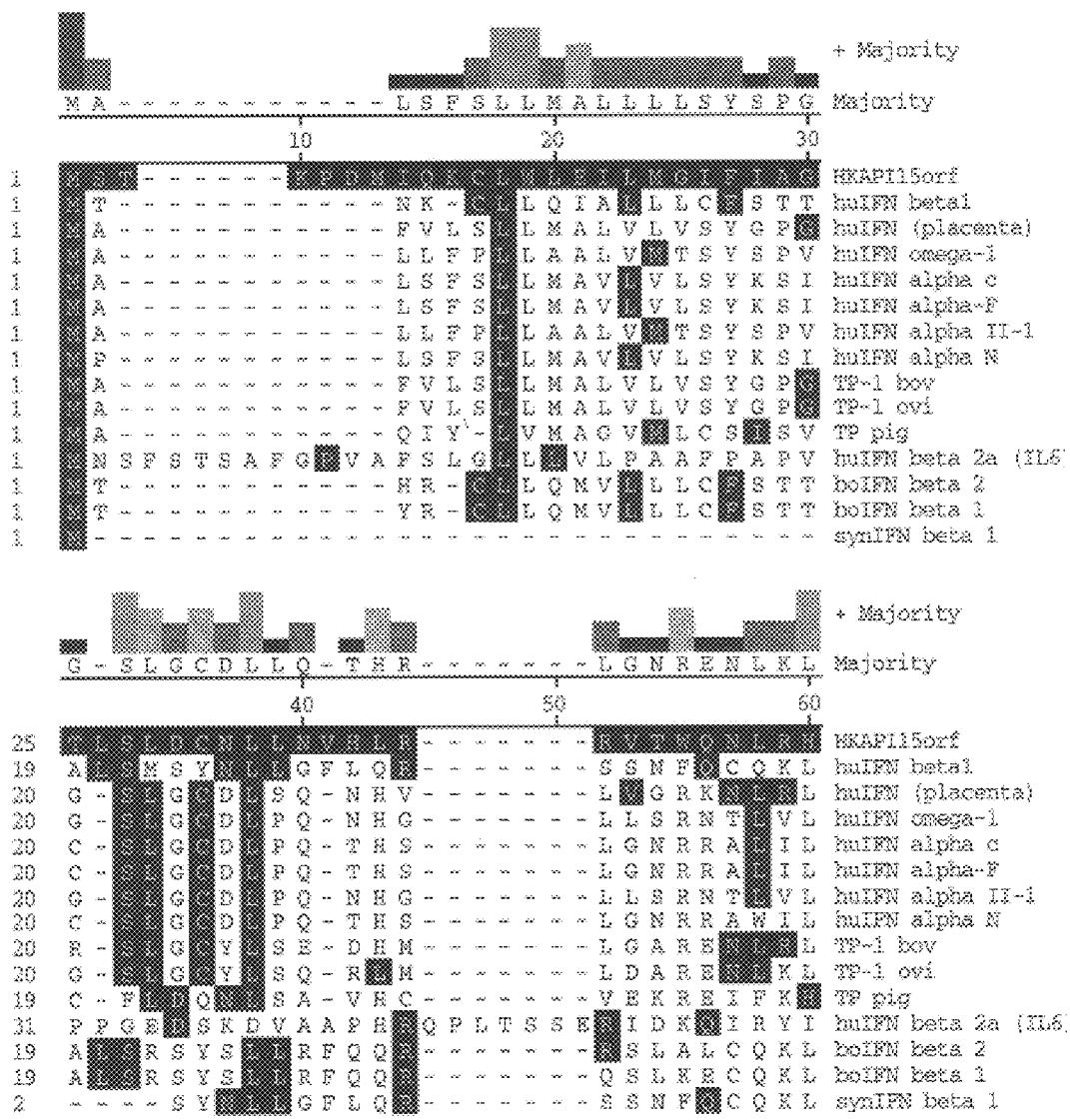
Figure 4B:
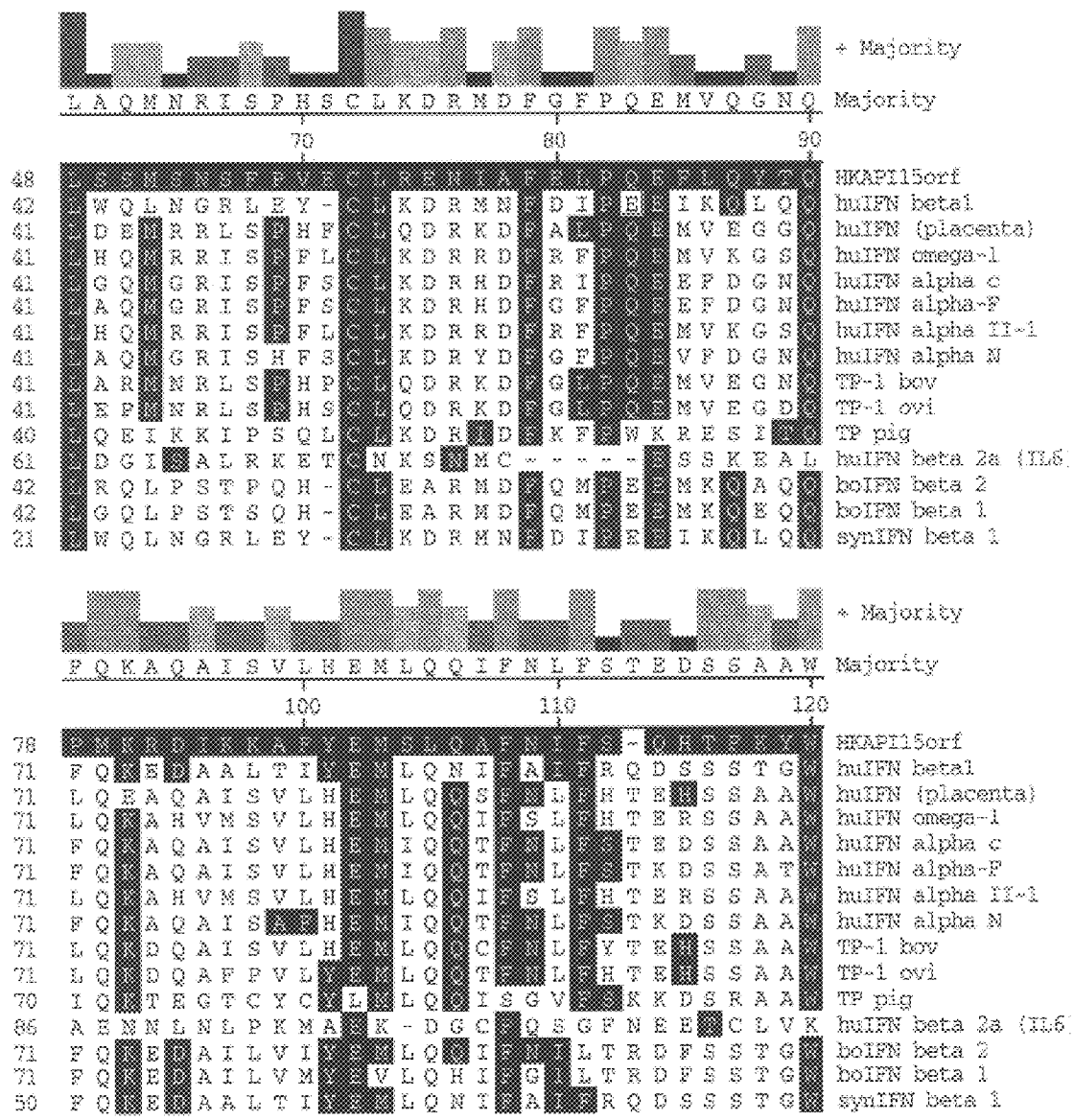
Figure 4C:
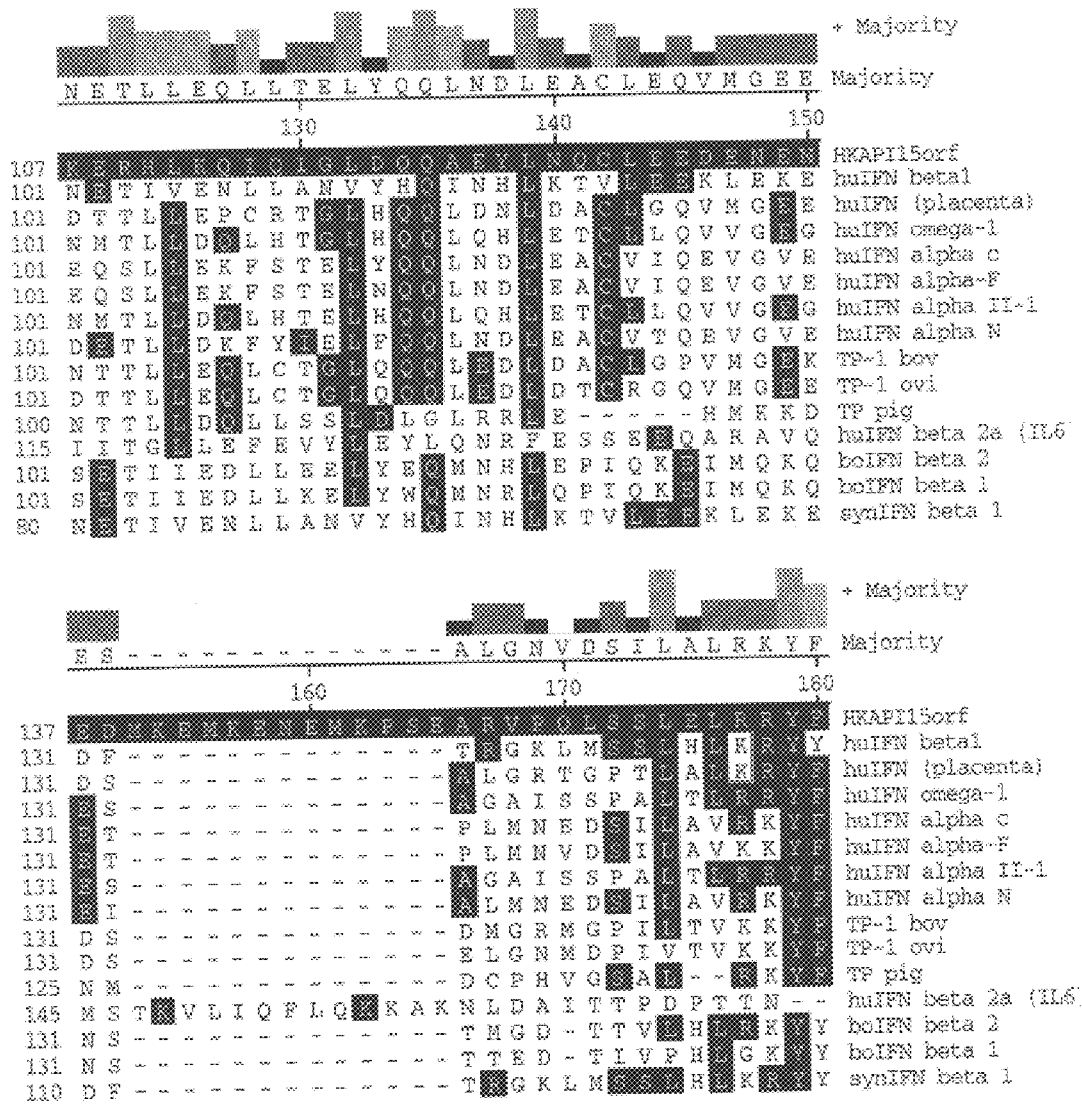
Figure 4D:
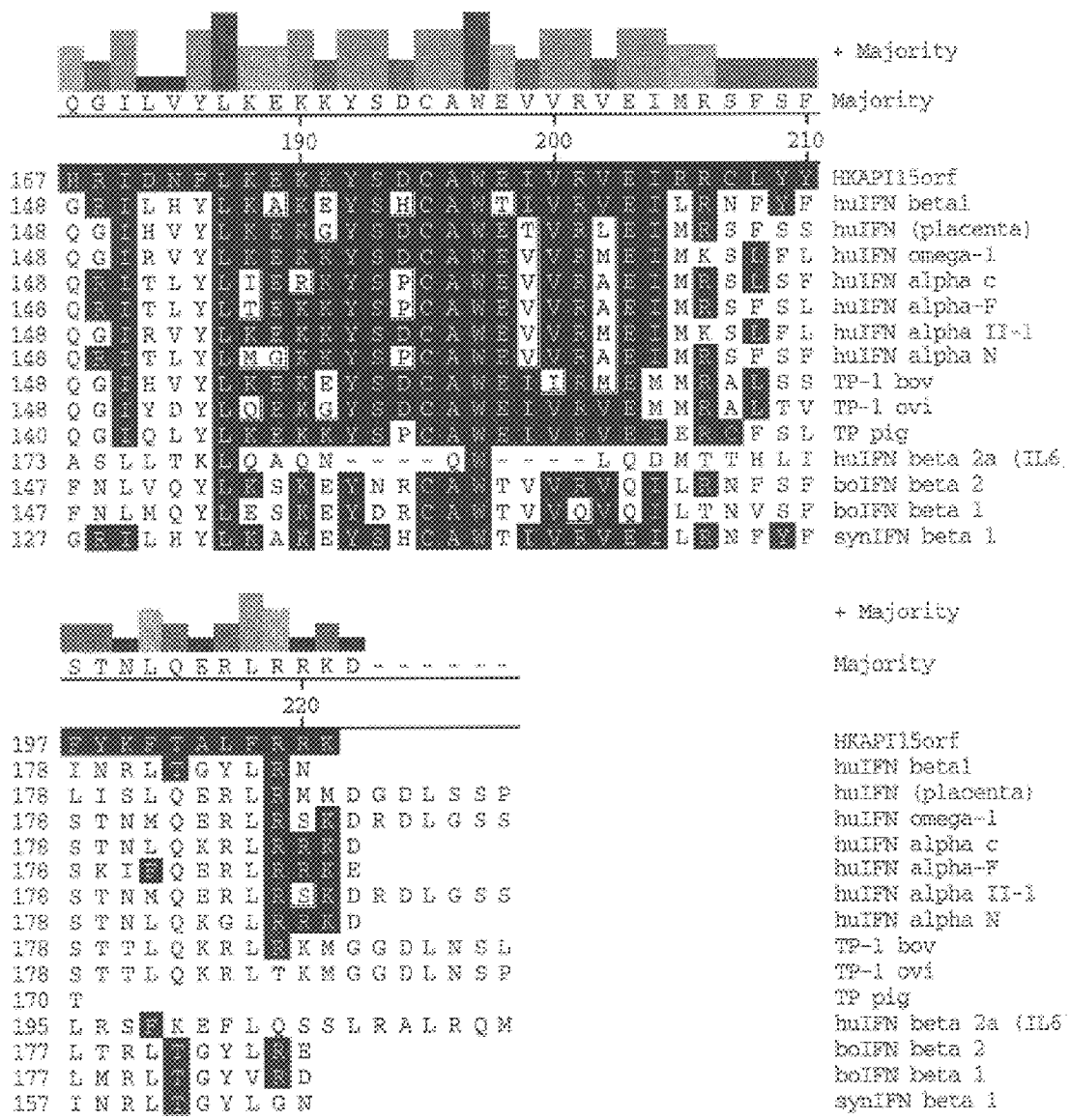

The data presented in FIG. 3 are also represented in tabular form in Table I. The columns are labeled with the headings "Res", "Position", and Roman Numerals I–XIII. The column headings refer to the following features of the amino acid sequence presented in FIG. 3, and Table I: "Res": amino acid residue of SEQ ID NO:2 and FIGS. 1; "Position": position of the corresponding residue within SEQ ID NO:2 and FIGS. 1; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson VI: Turn, Regions—Chou-Fasman; VII: Coil, Regions—Garnier-Robson; VIII: Hydrophilicity Plot—Kyte-Doolittle; IX: Alpha, Amphipathic Regions—Eisenberg; X: Beta, Amphipathic Regions—Eisenberg; XI: Flexible Regions—Karplus-Schulz; XII: Antigenic Index—Jameson-Wolf; and XIII: Surface Probability Plot—Emini.

FIG. 4 shows an alignment of the KDI polypeptide (SEQ ID NO:2) of the present invention with several other members of the interferon polypeptide family. Shown is human interferon beta-1 (SEQ ID NO:4), human placental interferon (SEQ ID NO:5), human interferon omega (SEQ ID NOS:3 and 6), human interferon alpha-c (SEQ ID NO:7), human interferon alpha-F (SEQ ID NO:8), human interferon II-1 (SEQ ID NO:9), human alpha interferon-N (SEQ ID NO:10), bovine TP-1 (SEQ ID NO:11), ovi TP-1 (SEQ ID NO:12), pig TP (SEQ ID NO:13), human interferon beta 2a (IL-6) (SEQ ID NO:14), bovine interferon beta-2 (SEQ ID NO:15), bovine interferon beta-1 (SEQ ID NO:20), and synthetic interferon beta-1 (SEQ ID NO:21). The alignment was produced by the Megalign routine using the Clustal method with PAM250 residue weight table. Megalign is contained within the DNAstar suite of programs. Amino acids identical to the KDI polypeptide (labeled HKAPI15orf) are boxed. By examining the regions of the boxed amino acids, the skilled artisan can readily identify conserved domains between the polypeptides. These conserved domains are preferred embodiments of the present invention.

FIG. 5 shows the human cDNA nucleotide sequence (SEQ ID NO:1) encoding KDI (designated "wt KDI orf") of the present invention as compared to the *E. coli* codon optimized, or "synthetic" nucleotide sequence (SEQ ID NO:22) encoding KDI (designated "s KDI orf"). The percent similarity of the synthetic DNA encoding KDI of the present invention as compared to the human cDNA encoding KDI of the present invention is 80.6%.

Figure 6:
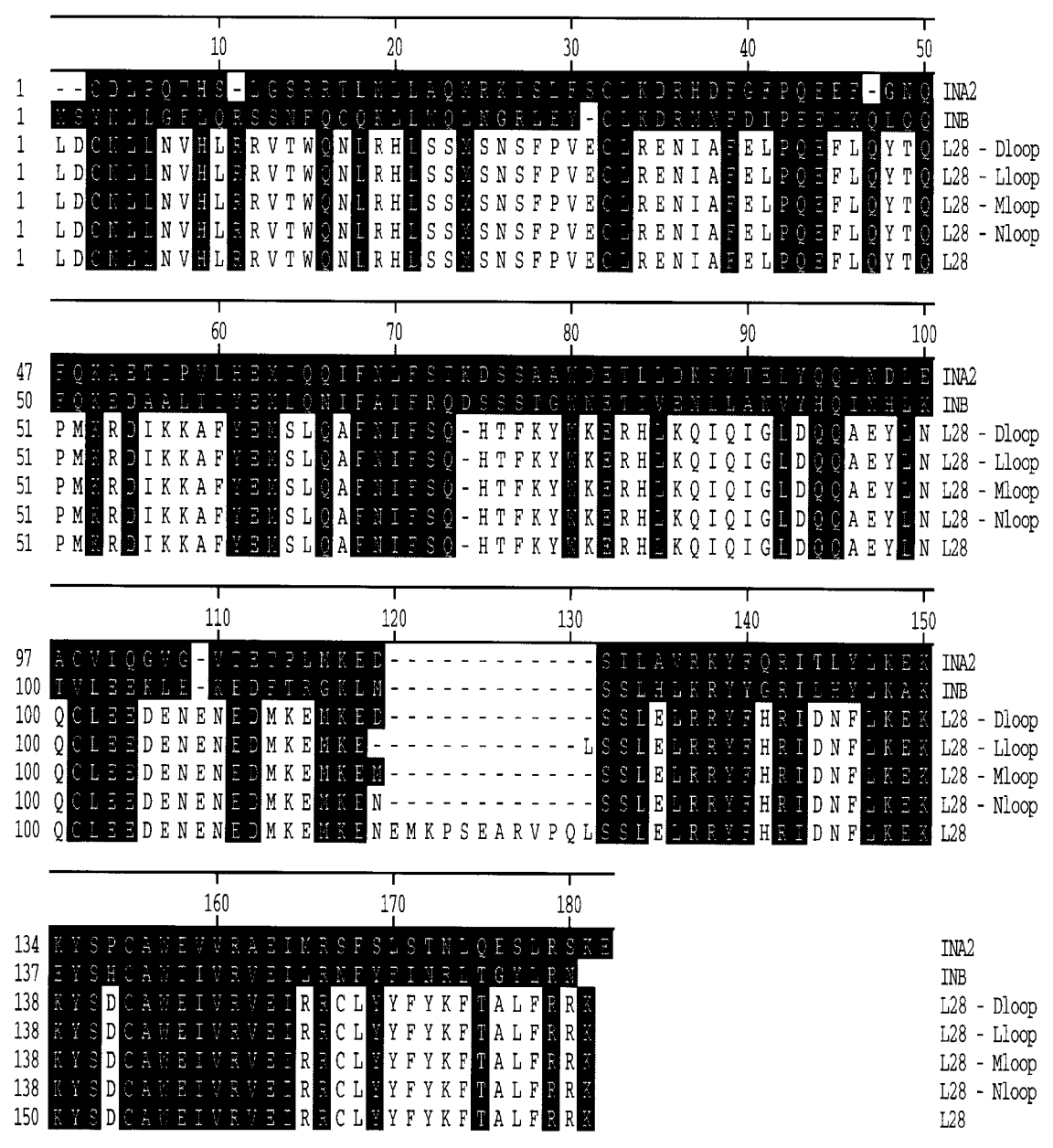

FIG. 6 shows a comparison of the amino acid sequence of the mature KDI polypeptide "L28" with that of the various KDI non-homologous loop deletion mutants. "L28" shows the amino acid sequence of the mature KDI protein. "L28-Dloop" shows a KDI polypeptide in which the non-homologous loop region at residues 173–184 is deleted, "L28-Lloop" shows a KDI polypeptide in which the non-homologous loop region at residues 172–183 is deleted; "L28-Mloop" shows a KDI polypeptide in which the non-homologous loop region at residues 173–184 is deleted and N172 is altered to M172, "L28-Nloop" shows a KDI polypeptide in which the non-homologous loop region at residues 173–184 is deleted. "INA2" shows the amino acid sequence of IFN alpha2, while "INB" shows the amino acid sequence of IFN beta.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" KDI protein refers to a protein capable of being directed to the ER, secretory vesicles, or the extracellular space as a result of a signal sequence, as well as a KDI protein released into the extracellular space without necessarily containing a signal sequence. If the KDI secreted protein is released into the extracellular space, the KDI secreted protein can undergo extracellular processing to produce a "mature" KDI protein. Release into the extracellular space can occur by many mechanisms, including exocytosis and proteolytic cleavage.

A "membrane" associated KDI polypeptide of the present invention may be utilized as a polypeptide integrated in a lipid membrane, such as a membrane-bound polypeptide, an intracellular polypeptide expressed in the cell's secretory pathway, a polypeptide expressed in the plasma membrane at the cell surface or as a polypeptide integrated synthetically into membrane-like structures such as in liposomes or micelles.

As used herein, a KDI "polynucleotide" refers to a molecule having a nucleic acid sequence contained in SEQ ID NO:1 or the cDNA contained within the clone deposited with the ATCC. For example, the KDI polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a KDI "polypeptide" refers to a molecule having the translated amino acid sequence generated from the polynucleotide as defined in the present invention.

The present invention provides isolated nucleic acid molecules comprising a polynucleotide encoding a Keratinocyte-Derived Interferon polypeptide (hereinafter "KDI") having the amino acid sequence shown in SEQ ID NO:2. The nucleotide sequence shown in FIG. 1 (SEQ ID NO:1) was obtained by sequencing the human HKAPI15 cDNA clone which was deposited on Dec. 1, 1998 at the American Type Culture Collection, 10801 University Boulevard, Manassas, Va. 20110-2209, USA, and given accession number ATCC 203500. The deposited cDNA is contained in the plasmid pCMVSport 2.0 (Life Technologies, Gaithersburg Md.) and can be excised by the SalI/NotI restriction enzyme sites flanking the human cDNA.

A KDI "polynucleotide" also includes those polynucleotides capable of hybridizing, under stringent hybridization conditions, to sequences contained in SEQ ID NO:1, the complement thereof, or the cDNA within the deposited clone. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the KDI polynucleotides under lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE×3M NaCl; 0.2M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The KDI polynucleotide can be composed of any polyribonucleotide or polydeoxribonucleotide, which may be unmodified RNA or DNA or modified RNA or DNA. For example, KDI polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the KDI polynucleotides can be composed of triple-stranded regions comprising RNA or DNA or both RNA and DNA. KDI polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

KDI polypeptides can be composed of amino acids joined to each other by peptide bonds or modified peptide bonds, i.e., peptide isosteres, and may contain amino acids other than the 20 gene-encoded amino acids. The KDI polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the KDI polypeptide, including the peptide backbone, the amino acid side-chains and the amino or carboxyl termini. It will be appreciated that the same type of modification may be present in the same or varying degrees at several sites in a given KDI polypeptide. Also, a given KDI polypeptide may contain many types of modifications. KDI polypeptides may be branched, for example, as a result of ubiquitination, and they may be cyclic, with or without branching. Cyclic, branched, and branched cyclic KDI polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).) "SEQ ID NO:1" refers to a KDI polynucleotide sequence while "SEQ ID NO:2" refers to a KDI polypeptide sequence.

A KDI polypeptide "having biological activity" refers to polypeptides exhibiting activity similar, but not necessarily identical to, an activity of a KDI polypeptide, including mature forms, as measured in a particular biological assay, with or without dose dependency. In the case where dose dependency does exist, it need not be identical to that of the KDI polypeptide, but rather substantially similar to the dose-dependence in a given activity as compared to the KDI polypeptide (i.e., the candidate polypeptide will exhibit greater activity or not more than about 25-fold less and, preferably, not more than about tenfold less activity, and most preferably, not more than about three-fold less. activity relative to the KDI polypeptide.)

The KDI protein of the present invention shares sequence homology with many members of the interferon family, noteably the translation product of the human mRNA for IFN-omega (FIG. 2) (SEQ ID NOS:3 and 6). IFN-omega has been shown to inhibit the proliferation of a variety of tumor cell lines in vitro, stimulate natural killer cell activity, enhance expression of major histocompatibility complex class I (but not class II) antigens and inhibit proliferation of lymphocytes stimulated with mitogens or allogeneic cells. Adolf, G. R., Human Interferon Omega—A Review, *Mult Scler* 1995;1 Suppl 1:S44–S47.

KDI is expressed mainly in keratinocytes, dentritic cells, monocytes and tonsil. KDI may be present in others cell and tissue types at much lower levels. KDI expression can be regulated by double stranded RNA as well as other cytokines, such as IFN gamma and Tumor Necrosis Factor (TNF). Stimulation of keratinocytes with TNF-α or PolyIC (simulating viral infection) specifically and rapidly stimulates overexpression of the KDI transcript. KDI is upregulated by INF gamma in monocytes and keratinocytes. Based on its structural similarity to IFN-omega and its increased expression in response to simulated viral infection, KDI is believed to share many of its biological activities of INF-Omega and other interferon proteins, including, inhibition of tumor proliferation, antiviral activities, NK cell activiation, and immune system enhancement.

Nucleic Acid Molecules

Unless otherwise indicated, all nucleotide sequences determined by sequencing a DNA molecule herein are determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C. and U), where each thymidine deoxyribonucleotide (T) in the specified deoxyribonucleotide sequence is replaced by the ribonucleotide uridine (U).

Using the information provided herein, such as the nucleotide sequence in FIG. 1 (SEQ ID NO:1), a nucleic acid molecule of the present invention encoding a KDI polypeptide may be obtained using standard molecular biology procedures, such as those for cloning cDNAs using mRNA as starting material. Illustrative of the invention, the nucleic acid molecule described in FIG. 1 (SEQ ID NO:1) was discovered in a cDNA library derived from isolated keratinocytes.

The nucleotide sequence of the KDI DNA of FIG. 1(SEQ ID NO:1) contains an open reading frame encoding a protein of 207 amino acid residues, with an initiation codon at nucleotide positions 35–37 of the nucleotide sequence in FIG. 1 (SEQ ID NO:1). The amino acid sequence of the KDI protein shown in SEQ ID NO:2 is about 35% identical to IFN-omega, (FIG. 2; SEQ ID NOS:3 and 6). The sequences of INF-Omega can be accessed through GenBank with Accession No. gb|A12140.

As one of ordinary skill would appreciate, due to the possibilities of sequencing errors discussed above, the actual complete KDI polypeptide encoded by the deposited cDNA, which comprises about 207 amino acids, may be somewhat longer or shorter. More generally, the actual open reading frame may be anywhere in the range of ±20 amino acids, more likely in the range of ±10 amino acids, of that predicted from the methionine codon at the N-terminus shown in FIG. 1 (SEQ ID NO:1).

The KDI nucleotide sequence identified as SEQ ID NO:1 was assembled from partially homologous ("overlapping") sequences obtained from the deposited clone. The overlapping sequences were assembled into a single contiguous sequence of high redundancy resulting in a final sequence identified as SEQ ID NO:1.

Therefore, SEQ ID NO:1 and the translated SEQ ID NO:2 are sufficiently accurate and otherwise suitable for a variety of uses well known in the art and described further below. For instance, SEQ ID NO:1 is useful for designing nucleic acid hybridization probes that will detect nucleic acid sequences contained in SEQ ID NO:1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used, for example, to generate antibodies which bind specifically to proteins KDI.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a human cDNA of KDI deposited with the ATCC. The nucleotide sequence of the deposited KDI clone can readily be determined by sequencing the deposited clone in accordance with known methods. The predicted KDI amino acid sequence can then be verified from such deposits. Moreover, the amino acid sequence of the protein encoded by the deposited clone can also be directly determined by peptide sequencing or by expressing the protein in a suitable host cell containing the deposited human KDI cDNA, collecting the protein, and determining its sequence.

The present invention also relates to the KDI gene corresponding to SEQ ID NO:1, SEQ ID NO:2, or the deposited clone. The KDI gene can be isolated in accordance with known methods using the sequence information disclosed herein. Such methods include preparing probes or primers from the disclosed sequence and identifying or amplifying the KDI gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:1, SEQ ID NO:2, or a the deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The KDI polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The KDI polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

KDI polypeptides are preferably provided in an isolated form, and preferably are substantially purified. A recombinantly produced version of a KDI polypeptide, including the secreted polypeptide, can be substantially purified using techniques described herein or otherwise known in the art,such as, for example, by the one-step method described in Smith and Johnson, Gene 67:31–40 (1988). KDI polypeptides also can be purified from natural, synthetic or recombinant sources using techniques described herein or otherwise known in the art, such as, for example, antibodies of the invention raised against the KDI protein.

The present invention provides a polynucleotide comprising, or alternatively consisting of, the nucleic acid sequence of SEQ ID NO:1, and/or a cDNA contained in ATCC deposit 203500. The present invention also provides a polypeptide comprising, or alternatively, consisting of, the polypeptide sequence of SEQ ID NO:2 and/or a polypeptide encoded by the cDNA contained in ATCC deposit 203500. Polynucleotides encoding a polypeptide comprising, or alternatively consisting of the polypeptide sequence of SEQ ID NO:2 and/or a polypeptide sequence encoded by the cDNA contained in ATCC deposit 203500 are also encompassed by the invention.

Leader and Mature Sequences

The amino acid sequence of the complete KDI protein includes a leader sequence and a mature protein, as shown in SEQ ID NO:2. More in particular, the present invention provides nucleic acid molecules encoding a mature form of the KDI protein having the polypeptide sequence of SEQ ID NO:2 and/or the polypeptide sequence encoded by the cDNA in a deposited clone. Polynucleotides encoding the mature forms (such as, for example, the polynucleotide sequence in SEQ ID NO:1 and/or the polynucleotide sequence contained in the cDNA of a deposited clone) are also encompassed by the invention. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. In some instances, proteins having a signal or leader sequence may be retained intracellularly or at the cell surface. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature KDI polypeptide having the amino acid sequence encoded by the human cDNA in clone HKAPI15 (ATCC Deposit No. 203500). By the "mature KDI polypeptide having the amino acid sequence encoded by the human cDNA in clone HKAPI15" is meant the mature form(s) of the KDI protein produced by expression in a mammalian cell (e.g., COS cells, as described below) from the open reading frame encoded by the human DNA sequence of the clone contained in the deposited vector or a portion of the DNA sequence of the clone contained in the deposited vector fused to a heterologous signal sequence.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues –13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete KDI polypeptide was analyzed by a computer program "PSORT", available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The computation analysis above predicted one potential cleavage site within the complete amino acid sequence shown in SEQ ID NO:2; that is, between residues 27 and 28 in FIG. 1 (SEQ ID NO:2). Of course the exact address of the cleavage site used by naturally occurring enzymes may vary slightly from the predicted cleavage site and may vary between species. The leucine at amino acid residue 28 of SEQ ID NO:2 is the N-terminal residue of KDI expressed in CHO and SF9 cells.

Accordingly, mature polypeptides beginning from about residue 20 to about residue 34 are provided. More in particular, the invention provides a polypeptide having a portion of SEQ ID NO:2 as follows: residues 20–207 in SEQ ID NO:2, residues 21–207 in SEQ ID NO:2, residues 22–207 in SEQ ID NO:2, residues 23–207 in SEQ ID NO:2, residues 24–207 in SEQ ID NO:2, residues 25–207 in SEQ ID NO:2, residues 26–207 in SEQ ID NO:2, residues 27–207 in SEQ ID NO:2, residues 28–207 in SEQ ID NO:2, residues 29–207 in SEQ ID NO:2, residues 30–207 in SEQ ID NO:2, residues 31–207 in SEQ ID NO:2, residues 32–207 in SEQ ID NO:2, residues 33–207 in SEQ ID NO:2, and residues 34–207 in SEQ ID NO:2, with a preferred mature polypeptide having residues 28–207 of SEQ ID NO:2. The invention also provides polynucleotides encoding such polypeptides.

As indicated, nucleic acid molecules of the present invention may be in the form of RNA, or in the form of DNA. The DNA may be double-stranded or single-stranded. Single-stranded DNA or RNA may be the coding strand, also known as the sense strand, or it may be the non-coding strand, also referred to as the anti-sense strand.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the KDI gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells, purified (partially or substantially) DNA molecules in solution and synthetic polynucleotides. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogenous solution containing the clone and other members of the library) or a chromosome isolated or removed from a cell or cell lysate (e.g., a "chromosome spread", as in a karyotype), is not "isolated" for the purposes of this invention. As discussed further herein, isolated nucleic acid molecules according to the present invention may be produced naturally, recombinantly or synthetically.

Isolated nucleic acid molecules of the present invention include DNA molecules comprising an open reading frame (ORF) with an initiation codon at positions 35–37 of the nucleotide sequence shown in FIG. 1 (SEQ ID NO:1).

Also included are DNA molecules comprising the coding sequence for the KDI protein lacking an N-terminal methionine shown at positions 2–207 of SEQ ID NO:2.

In addition, isolated nucleic acid molecules of the invention include DNA molecules which comprise a sequence substantially different from those described above but which, due to the degeneracy of the genetic code, still encodes a KDI polypeptide of the present invention. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as E. coli).

In another aspect, the invention provides isolated nucleic acid molecules encoding the KDI polypeptide having an amino acid sequence encoded by the human cDNA in clone HKAPI15 (ATCC Deposit No. 203500). Preferably, this nucleic acid molecule will encode the mature polypeptide encoded by the above-described deposited human cDNA.

The invention further provides an isolated nucleic acid molecule having the nucleotide sequence shown in FIG. 1 (SEQ ID NO:1) or the nucleotide sequence of the KDI cDNA contained in the above-described deposited clone, or a nucleic acid molecule having a sequence complementary to one of the above sequences. Such isolated molecules, particularly DNA molecules, are useful for production of the KDI polypeptide of the invention and as a probe for detection of mRNA in cells transfected with a vector for the purpose of producing KDI; i.e., as a marker for determining expression of the heterologous gene in a host cell.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO: I which consists of positions 35–655 of SEQ ID NO:1. Other particularly preferred polynucleotide fragments of the invention comprise, or alternatively, consist of nucleotide residues 38–655, 41–655, 44–655, 47–655, 50–655, 53–655, 56–655, 59–655, 62–655, 65–655, 68–655, 71–655, 74–655, 77–655, 80–655, 83–655, 86–655, 89–655, 92–655, 95–655, 98–655, 101–655, 104–655, 107–655, 110–655, 113–655, 116–655, 119–655, 122–655, 125–655, 128–655, 131–655, 134–655, 137–655, 140–655, 143–655, 146–655, 149–655, 152–655, 155–655, 158–655, 161–655, 164–655, 167–655, 170–655, 173–655, 176–655, 179–655, 182–655, 185–655, 188–655, 191–655, 194–655, 197–655, 200–655, 203–655, 206–655, 209–655, 212–655, 215–655, 218–655, 221–655, 224–655, 227–655, 230–655, 233–655, 236–655, 239–655, 242–655, 245–655, 248–655, 251–655, 254–655, 257–655, 260–655, 263–655, 266–655, 269–655, 272–655, 275–655, 278–655, 281–655, 284–655, 287–655, 290–655, 293–655, 296–655, 299–655, 302–655, 305–655, 308–655, 311–655, 314–655, 317–655, 320–655, 323–655, 326–655, 329–655, 332–655, 335–655, 338–655, 341–655, 344–655, 347–655, 350–655, 353–655, 356–655, 359–655, 362–655, 365–655, 368–655, 371–655, 374–655, 377–655, 380–655, 383–655, 386–655, 389–655, 392–655, 395–655, 398–655, 401–655, 404–655, 407–655, 410–655, 413–655, 416–655, 419–655, 422–655, 425–655, 428–655, 431–655, 434–655, 437–655, 440–655, 443–655, 446–655, 449–655, 452–655, 455–655, 458–655, 461–655, 464–655, 467–655, 470–655, 473–655, 476–655, 479–655, 482–655, 485–655, 488–655, 491–655, 494–655, 497–655, 500–655, 503–655, 506–655, 509–655, 512–655, 515–655, 518–655, 521–655, 524–655, 527–655, 530–655, 533–655, 536–655, 539–655, 542–655, 545–655, 548–655, 551–655, 554–655, 557–655, 560–655, 563–655, 566–655, 569–655, 572–655, 575–655, 578–655, 581–655, 584–655, 587–655, 590–655, 593–655, 596–655, 599–655, 602–655, 605–655, 608–655, 611–655, 614–655, 617–655, 620–655, 623–655, 626–655, 629–655, 632–655, and 635–655 of SEQ ID NO:1. Still other particularly preferred polynucleotide fragments of the invention comprise, or alternatively, consist of nucleotide residues 38–68, 38–71, 38–74, 38–77, 38–80, 38–83, 38–86, 38–89, 38–92, 38–95, 38–98, 38–101, 38–104, 38–107, 38–110, 38–113, 38–116, 38–119, 38–122, 38–125, 38–128, 38–131, 38–134, 38–137, 38–140, 38–143, 38–146, 38–149, 38–152, 38–155, 38–158, 38–161, 38–164, 38–167, 38–170, 38–173, 38–176, 38–179, 38–182, 38–185, 38–188, 38–191, 38–194, 38–197, 38–200, 38–203, 38–206, 38–209, 38–212, 38–215, 38–218, 38–221, 38–224, 38–227, 38–230, 38–233, 38–236, 38–239, 38–242, 38–245, 38–248, 38–251, 38–254, 38–257, 38–260, 38–263, 38–266, 38–269, 38–272, 38–275, 38–278, 38–281, 38–284, 38–287, 38–290, 38–293, 38–296, 38–299, 38–302, 38–305, 38–308, 38–311, 38–314, 38–317, 38–320, 38–323, 38–326, 38–329, 38–335, 38–338, 38–341, 38–344, 38–347, 38–350, 38–353, 38–356, 38–359, 38–362, 38–365, 38–368, 38–371, 38–374, 38–377, 38–380, 38–383, 38–386, 38–389, 38–392, 38–395, 38–398, 38–401, 38–404, 38–407, 38–410, 38–413, 38–416, 38–419, 38–422, 38–425, 38–428, 38–431, 38–434, 38–437, 38–440, 38–443, 38–446, 38–449, 38–452, 38–455, 38–458, 38–461, 38–464, 38–467, 38–470, 38–473, 38–476, 38–479, 38–482, 38–485, 38–488, 38–491, 38–494, 38–497, 38–500, 38–503, 38–506, 38–509, 38–512, 38–515, 38–518, 38–521, 38–524, 38–527, 38–530, 38–533, 38–536, 38–539, 38–542, 38–545, 38–548, 38–551, 38–554, 38–557, 38–560, 38–563, 38–566, 38–569, 38–572, 38–575, 38–578, 38–581, 38–584, 38–587, 38–590, 38–593, 38–596, 38–599, 38–602, 38–605, 38–608, 38–611, 38–614, 38–617, 38–620, 38–623, 38–626, 38–629, 38–632, and 38–635 of SEQ ID NO:1.

Further, the invention includes a polynucleotide comprising any portion of at least about 30 contiguous nucleotides, preferably at least about 50 contiguous nucleotides, of SEQ ID NO:1.

More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–600 nt in length (fragments of 400 nt, 450 nt, 500 nt, 550 nt and 600 nt in length are specifically contemplated as are fragments of all lengths between 15 and 600 but will not be specifically recited for space considerations) are also useful according to the present invention as are fragments corresponding to most, if not all, of the nucleotide sequence of the deposited cDNA or as shown in FIG. 1 (SEQ ID NO:1). By a fragment "at least 20 nt in length", for example, is intended fragments which include 20 or more contiguous bases from the nucleotide sequence of the deposited cDNA or the nucleotide sequence as shown in FIG. 1 (SEQ ID NO:1) and may, of course, comprise additional nucleic acid sequences not derived from SEQ ID NO:1 (or the deposited cDNA) fused to either end of the 20+ contiguous bases from SEQ ID NO:1 or the deposited cDNA. Preferred nucleic acid fragments of the present invention include nucleic acid molecules encoding epitope-bearing portions of the KDI polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the human cDNA in clone HKAPI15 (ATCC Deposit No. 203500) to sequences contained in SEQ ID NO:1, or the complement thereof. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1³³ SSC at about 65 degree C.

Also contemplated are nucleic acid molecules that hybridize to the KDI polynucleotides under lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using digo dT as a primer).

The KDI polynucleotide can be composed of any polyribonucleotide or polydeoxribonucleotide, which may be unmodified RNA or DNA or modified RNA or DNA. For example, KDI polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the KDI polynucleotides can be composed of triple-stranded regions comprising RNA or DNA or both RNA and DNA. KDI polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 75 kb, or 5 kb in length.

KDI polypeptides can be composed of amino acids joined to each other by peptide bonds or modified peptide bonds, i.e., peptide isosteres, and may contain amino acids other than the 20 gene-encoded amino acids. The KDI polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the KDI polypeptide, including the peptide backbone, the amino acid side-chains and the amino or carboxyl termini. it will be appreciated that the same type of modification may be present in the same or varying degrees at several sites in a given KDI polypeptide.

Also, a given KDI polypeptide may contain many types of modifications. KDI polypeptides may be branched, for example, as a result of ubiquitination, and they may be cyclic, with or without branching. Cyclic, branched, and branched cyclic KDI polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racerization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1" refers to a KDI polynucleotide sequence while "SEQ ID NO:2" refers to a KDI polypeptide sequence.

A KDI polypeptide "having biological activity" refers to polypeptides exhibiting activity similar, but not necessarily identical to, an activity of a KDI polypeptide, including mature forms, as measured in a particular biological assay, with or without dose dependency. Examples of preferred biological assays include: assessment of anti-viral activity, assessment of anti-proliferative activity, interferon receptor binding, activation of the Jak/STAT signally pathway and activation of interferon inducible genes. In the case where dose dependency does exist, it need not be identical to that of the KDI polypeptide, but rather substantially similar to the dose-dependence in a given activity as compared to the KDI polypeptide (i.e., the candidate polypeptide will exhibit greater activity or not more than about 25-fold less and, preferably, not more than about tenfold less activity, and most preferably, not more than about three-fold less activity relative to the KDI polypeptide).

As indicated, nucleic acid molecules of the present invention which encode a KDI polypeptide may include, but are not limited to those encoding the amino acid sequence of the complete polypeptide, by itself, and the coding sequence for the complete polypeptide and additional sequences, such as those encoding an added secretory leader sequence, such as a pre-, or pro- or prepro-protein sequence.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification or identification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Nati. Acad. Sci. USA 86:821–824(1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37:767 (1984). In another preferred embodiment of this aspect of the invention, the FLAG amino acid sequence provides for the convenient identification of the fusion protein. As discussed below, other such fusion proteins include the KDI fused to Fc at the N- or C-terminus.

Variant and Mutant Polynucleotides

The present invention is directed to variants of the polynucleotide sequence disclosed in SEQ ID NO:1, the complementary strand thereto, and/or the cDNA sequence contained in a deposited clone.

The present invention also encompasses variants of the polypeptide sequence disclosed in SEQ ID NO:2 and/or encoded by a deposited clone.

The present invention further relates to variants of the nucleic acid molecules of the present invention, which encode portions, analogs or derivatives of the KDI protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the KDI protein or portions thereof. Also especially preferred in this regard are conservative substitutions.

Further embodiments include an isolated nucleic acid molecule which comprise, or alternatively consist of, a polynucleotide having a nucleotide sequence at least 80%, 85%, or 90% identical, more preferably at least 91%, 92%, 93%, and 94% and most preferably at least 95%, 96%, 97%, 98% or 99% identical to a polynucleotide selected from the group consisting of: (a) a nucleotide sequence encoding the KDI polypeptide having the complete amino acid sequence in SEQ ID NO:2; (b) a nucleotide sequence encoding the KDI polypeptide having the complete amino acid sequence in SEQ ID NO:2 excepting the N-terminal methionine (i.e., residues 2–161 of SEQ ID NO:2); (c) a nucleotide sequence encoding the mature KDI polypeptide having the sequence shown as residues 28–207 in SEQ ID NO:2; (d) a nucleotide sequence encoding residues 7–207 in SEQ ID NO:2; (e) a nucleotide sequence encoding the complete amino acid sequence encoded by the human cDNA contained in clone HKAPI15; (f) a nucleotide sequence encoding the complete amino acid sequence encoded by the human cDNA contained in clone HKAPI15 excepting the N-terminal methionine; (g) a nucleotide sequence encoding the amino acid sequence of the mature polypeptide encoded by the human cDNA contained in clone HKAPI15; (h) a nucleotide sequence encoding polynucleotide fragments of (a), (b), (c), (d), (e), (f), and/or (g); and (i) a nucleotide sequence complementary to any of the nucleotide sequences in (a), (b), (c), (d), (e), (f), (g), (h), and (i) above.

Further embodiments of the invention include isolated nucleic acid molecules that comprise a polynucleotide having a nucleotide sequence at least 80%, 85%, or 90% identical, more preferably at least 91%, 92%, 93%, or 94% and most and most preferably at least 95%, 96%, 97%, 98% or 99% identical, to any of the nucleotide sequences in (a), (b), (c), (d), (e), (f), (g), (h), or (i) above, or a polynucleotide which hybridizes under stringent hybridization conditions to a polynucleotide in (a), (b), (c), (d), (e), (f), (g), (h), or (i) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a KDI polypeptide having an amino acid sequence in (a), (b), (c), (d), (e), (f), (g), or (h) above.

The present invention also relates to recombinant vectors, which include the isolated nucleic acid molecules of the present invention, and to host cells containing the recombinant vectors, as well as to methods of making such vectors and host cells and for using them for production of KDI polypeptides or peptides by recombinant techniques.

By a polynucleotide having a nucleotide sequence at least, for example, 95% "identical" to a reference nucleotide sequence encoding a KDI polypeptide is intended that the nucleotide sequence of the polynucleotide is identical to the reference sequence except that the polynucleotide sequence may include up to five point mutations per each 100 nucleotides of the reference nucleotide sequence encoding the KDI polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The query sequence may be an entire sequence shown of SEQ ID NO:1, the ORF (open reading frame), or any fragment specified as described herein. The preferred reference sequences are the polynucleotides of the present invention, such as a codon optimized polynucleotide sequence of the present invention.

One example of a codon optimized polynucleotide of the present invention is the sequence of "synthetic KDI" shown in FIG. 5 (SEQ ID NO:22), which encodes amino acids residues L28 to K207 of SEQ ID NO:2. The percent similarity of synthetic DNA encoding KDI as compared to human cDNA is 80.6%. Other codon optimized polynucleotides of the present invention may be produced by those of skill in the art, which can have similarities that are both lower and higher than 80%. Not only may the "synthetic KDI" polynucleotide sequence of FIG. 5 (SEQ ID NO:22) be used to express KDI in bacterial cells, but it can also be used to express KDI in mammalian cells.

As a practical matter, whether any particular nucleic acid molecule is at least 80%, 85%, 90%, 91%, 92%, 93%, 94%, 95%, 96%, 97%, 98% or 99% identical to a nucleotide sequence of the present invention, for instance, the nucleotide sequence shown in FIG. 1 or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (Advances in *Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The KDI variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. KDI polynucleotide variants can be produced for a variety of reasons, e.g., to optimize codon expression for a particular host (change codons in the human mRNA to those preferred by a bacteria host such as E. coli).

Naturally occurring KDI variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the KDI polypeptides. For instance, one or more amino acids can be deleted from the N-terminus or C-terminus of the secreted protein without substantial loss of biological function. The authors of Ron et al., J. Biol. Chem. 268: 2984–2988 (1993), reported variant KDI proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1α. They used random mutagenesis to generate over 3,500 individual IL-1α mutants that averaged 2.5 amino acid chances per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes KDI polypeptide variants which show substantial biological activity. Such variants include deletions, insertions, inversions, repeats, and substitutions selected according to general rules known in the art so as have little effect on activity.

The present application is directed to nucleic acid molecules at least 80%, 85%, 90%, 95%, 96%, 97%, 98% or 99% identical to the nucleic acid sequence shown in FIG. 1 (SEQ ID NO:1) or to the nucleic acid sequence of the deposited DNA or disclosed herein elsewhere, (e.g., encoding a polypeptide having the amino acid sequence of an N and/or C terminal deletion disclosed below as m-n of SEQ ID NO:2), irrespective of whether they encode a polypeptide having KDI activity. This is because even where a particular nucleic acid molecule does not encode a polypeptide having KDI activity, one of skill in the art would still know how to use the nucleic acid molecule, for instance, as a hybridization probe or a polymerase chain reaction (PCR) primer. Uses of the nucleic acid molecules of the present invention that do not encode a polypeptide having KDI activity include, inter alia, (1) isolating a KDI gene or allelic or splice variants thereof in a cDNA library; (2) in situ hybridization (e.g., "FISH") to metaphase chromosomal spreads to provide precise chromosomal location of the KDI gene, as described in Verma et al., Human Chromosomes: A Manual of Basic Techniques, Pergamon Press, New York (1988); and (3) Northern Blot analysis for detecting KDI mRNA expression in specific tissues.

Preferred, however, are nucleic acid molecules having sequences at least 80%, 85%, 90%, 95%, 96%, 97%, 98% or 99% identical to the nucleic acid sequence shown in FIG. 1(SEQ ID NO:1) or to the nucleic acid sequence of the deposited DNA which do, in fact, encode a polypeptide having KDI protein activity. By "a polypeptide having KDI activity" is intended polypeptides exhibiting activity similar, but not necessarily identical, to an activity of the KDI protein of the invention (e.g., complete (full-length) KDI, mature KDI and soluble KDI (e.g., having sequences contained in the extracellular domain of KDI), as measured, for example, in a particular immunoassay or biological assay. For example, the KDI protein of the present invention may inhibit bone marrow colony formation in-vitro. An example of a method for assessing bone marrow colony formation in vitro is that of Tiefenthaler M. et al., Interjeron Cytokine Res, (1997) 17(6):327–329, incorporated herein by reference in its entirety. In addition, KDI may inhibit GM-CSF induced proliferation of the erythroleukaemic cell line TF-1, which can be assayed according the the methods reported by Mire-Sluis A. R. et al., J. Immunol. Methods (1996) 9:195:55–61, incorporated herein by reference in its entirety. Also, KDI may be assayed for classical anti-viral activity by any of several assays known to those of skill in the art, for example, in the assay reported by Sugiyama, K. et al., Yakugaku Zasshi (1995) 115:390–393. Human cDNAs encoding KDI can be used for somatic cell hybrid mapping to a human chromosome. See Example 8, below. KDI induces MxA mRNA in Daudi cells, keratinocytes and dendritic cells which is an indicator of clinical responsiveness to interferon therapy. See Examples 5 and 6, below. MxA is indicative of anti-viral activity. MxA has also been shown to be induced in respone to Interferon-alpha2 treatment. See Antonelli et al., J. Interferon Cytokine Res 19:243–51 (1999).

The KDI protein of the present invention inhibits bone marrow proliferation and shows anti-viral activity in a dose-dependent manner in the above-described assays. Thus, "a polypeptide having KDI protein activity" includes polypeptides that also exhibit any of the same activities in the above-described assays in a dose-dependent manner. Although the degree of dose-dependent activity need not be identical to that of the KDI protein, preferably, "a polypeptide having KDI protein activity" will exhibit substantially similar dose-dependence in a given activity as compared to the KDI protein (i.e., the candidate polypeptide will exhibit greater activity or not more than about 25-fold less and, preferably, not more than about tenfold less activity relative to the reference KDI protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1), or fragments thereof, will encode a polypeptide "having KDI protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having KDI protein activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For example, site directed changes at the amino acid level of KDI can be made by replacing a particular amino acid with a conservative amino acid. Preferred conservative mutations include: M1replaced with A, G, I, L, S, T, or V; S2 replaced with A, G, I, L, T, M, or V; T3 replaced with A, G, I, L, S, M, or V; K4 replaced with H, or R; D6 replaced with E; M7 replaced with A, G, I, L, S, T, or V; I8 replaced with A, G, L, S, T, M, or V; Q9 replaced with N; K10 replaced with H, or R; L12 replaced with A, G, I, S, T, M, or V; W13 replaced with F, or Y; L14 replaced with A, G, I, S, T, M, or V; E15 replaced with D; I16 replaced with A, G, L, S, T, M, or V; L17 replaced with A, G, I, S, T, M, or V; M18 replaced with A, G, I, L, S, T, or V; G19 replaced with A, I, L, S, T, M, or V; 120 replaced with A, G, L, S, T, M, or V; F21 replaced with W, or Y; 122 replaced with A, G, L, S, T, M, or V; A23 replaced with G, I, L, S, T, M, or V; G24 replaced with A, I, L, S, T, M, or V; T25 replaced with A, G, I, L, S, M, or V; L26 replaced with A, G, I, S, T, M, or V; S27 replaced with A, G, I, L, T, M, or V; L28 replaced with A, G, I, S, T, M, or V; D29 replaced with E; N31 replaced with Q; L32 replaced with A, G, I, S, T, M, or V; L33 replaced with A, G, I, S, T, M, or V; N34 replaced with Q; V35 replaced with A, G, I, L, S, T, or M; H36 replaced with K, or R; L37 replaced with A, G, I, S, T, M, or V; R38 replaced with H, or K; R39 replaced with H, or K; V40 replaced with A, G, I, L, S, T, or M; T41 replaced with A, G, I, L, S, M, or V; W42 replaced with F, or Y; Q43 replaced with N; N44 replaced with Q; L45 replaced with A, G, I, S, T, M, or V; R46 replaced with H, or K; H47 replaced with K, or R; L48 replaced with A, G, I, S, T, M, or V; S49 replaced with A, G, I, L, T, M, or V; S50 replaced with A, G, I, L, T, M, or V; M51 replaced with A, G, I, L, S, T, or V; S52 replaced with A, G, I, L, T, M, or V; N53 replaced with Q; S54 replaced with A, G, I, L, T, M, or V; F55 replaced with W, or Y; V57 replaced with A, G, I, L, S, T, or M; E58 replaced with D; L60 replaced with A, G, I, S, T, M, or V; R61 replaced with H, or K; E62 replaced with D; N63 replaced with Q; I64 replaced with A, G, L, S, T, M, or V; A65 replaced with G, I, L, S, T, M, or V; F66 replaced with W, or Y; E67 replaced with D; L68 replaced with A, G, I, S, T, M, or V; Q70 replaced with N; E71 replaced with D; F72 replaced with W, or Y; L73 replaced with A, G, I, S, T, M, or V; Q74 replaced with N; Y75 replaced with F, or W; T76 replaced with A, G, I, L, S, M, or V; Q77 replaced with N; M79 replaced with A, G, I, L, S, T, or V; K80 replaced with H, or R; R81 replaced with H, or K; D82 replaced with E; I83 replaced with A, G, L, S, T, M, or V; K84 replaced with H, or R; K85 replaced with H, or R; A86 replaced with G, I, L, S, T, M, or V; F87 replaced with W, or Y; Y88 replaced with F, or W; E89 replaced with D; M90 replaced with A, G, I, L, S, T, or V; S91 replaced with A, G, I, L, T, M, or V; L92 replaced with A, G, I, S, T, M, or V; Q93 replaced with N; A94 replaced with G, I, L, S, T. M, or V; F95 replaced with W, or Y; N96 replaced with Q; I97 replaced with A, G, L, S, T, M, or V; F98 replaced with W, or Y; S99 replaced with A, G, I, L, T, M, or V; Q100 replaced with N; H101 replaced with K, or R; T102 replaced with A, G, I, L, S, M, or V; F103 replaced with W, or Y; K104 replaced with H, or R; Y105 replaced with F., or W; W106 replaced with F, or Y; K107 replaced with H, or R; E108 replaced with D; R109 replaced with H, or K; H110 replaced with K, or R; L111 replaced with A, G, I, S, T, M, or V; K112 replaced with H, or R; Q113 replaced with N; I114 replaced with A, G, L, S, T, M, or V; Q115 replaced with N: I116 replaced with A, G, L, S, T, M, or V; G117 replaced with A, I, L, S, T, M, or V; L118 replaced with A, G, I, S, T, M, or V; D119 replaced with E; Q120 replaced with N; Q121 replaced with N; A122 replaced with G, I, L, S, T, M, or V; E123 replaced with D; Y124 replaced with F, or W; L125 replaced with A, G, I, S, T, M, or V; N126 replaced with Q; Q127 replaced with N; L129 replaced with A, G, I, S, T, M, or V: E 130 replaced with D; E131 replaced with D; D132 replaced with E; E 133 replaced with D; N134 replaced with Q; E135 replaced with D; N136 replaced with Q; E137 replaced with D; D138 replaced with E; M139 replaced with A, G, I, L, S, T, or V; K140 replaced with H, or R; E141 replaced with D; M142 replaced with A, G, I, L, S, T, or V: K143 replaced with H, or R; E144 replaced with D; N145 replaced with Q; E146 replaced with D; M147 replaced with A, G, I, L, S, T, or V; K148 replaced with H, or R; S150 replaced with A, G, I, L, T, M, or V; E151 replaced with D; A152 replaced with G, I, L, S, T, M, or V: R153 replaced with H, or K; V154 replaced with A, G, I, L, S, T, or M; Q156 replaced with N; L157 replaced with A, G, I, S, T, M, or V; S158 replaced with A, G, I, L, T, M, or V; S159 replaced with A, G, I, L, T, M, or V; L160 replaced with A, G, I, S, T, M, or V; E161 replaced with D: L162 replaced with A, G, I, S, T, M, or V; R163 replaced with H, or K; R164 replaced with H, or K; Y165 replaced with F, or W; F166 replaced with W, or Y; H167 replaced with K, or R; R168 replaced with H, or K; I169 replaced with A, G, L, S, T, M, or V; D170 replaced with E; N171 replaced with Q; F172 replaced with W, or Y; L173 replaced with A, G, I, S, T, M, or V; K174 replaced with H, or R; E175 replaced with D; K176 replaced with H, or R; K177 replaced with H, or R; Y178 replaced with F, or W; S179 replaced with A, G, I, L, T, M, or V; D180 replaced with E; A182 replaced with G, I, L, S, T, M, or V; W183 replaced with F, or Y; E184 replaced with D; I185 replaced with A, G, L, S, T, M, or V; V 186 replaced with A, G, I, L, S, T, or M; R 187 replaced with H, or K; V 188 replaced with A, G, I, L, S, T, or M; E 189 replaced with D; I190 replaced with A, G, L, S, T, M, or V; R191 replaced with H, or K; R192 replaced with H, or K; L194 replaced with A, G, I, S, T, M, or V; Y195 replaced with F, or W; Y 196 replaced with F, or W; F197 replaced with W, or Y; Y198 replaced with F, or W; K199 replaced with H, or R; F200 replaced with W, or Y; T201 replaced with A, G, I, L, S, M, or V; A202 replaced with G, I, L, S, T, M, or V; L203 replaced with A, G, I, S, T, M, or V; F204 replaced with W, or Y; R205 replaced with H, or K; R206 replaced with H, or K; and/or K207 replaced with H, or R in SEQ ID NO:2.

The resulting constructs can be routinely screened for activities or functions described throughout the specification and known in the art. Preferably, the resulting constructs have an increased and/or a decreased KDI activity or function, while the remaining KDI activities or functions are maintained. More preferably, the resulting constructs have more than one increased and/or decreased KDI activity or function, while the remaining KDI activities or functions are maintained.

Besides conservative amino acid substitution, variants of KDI include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, KDI polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 1993).)

For example, preferred non-conservative substitutions of KDI include: M1 replaced with D, E, H, K, R, N, Q, F, W, Y, P, or C; S2 replaced with D, E, H, K, R, N, Q, F, W, Y, P, or C; T3 replaced with D, E, H, K, R, N, Q, F, W, Y, P, or C; K4 replaced with D, E, A, G, I, L, S, T, M, V, N, Q, F, W, Y, P, or C; P5 replaced with D, E, H, K, R, A, G, I, L, S, T, M, V, N, Q, F, W, Y, or C; D6 replaced with H, K, R, A, G, I, L, S, T, M, V, N, Q, F, W, Y, P, or C; M7 replaced with D, E, H, K, R, N, Q, F, W, Y, P, or C; 18 replaced with D, E, H, K, R, N, Q, F, W, Y, P, or C; Q9 replaced with D, E, H, K, R, A, G, I, L, S, T, M, V, F, W, Y, P, or C; K10 replaced with D, E, A, G, I, L, S, T, M, V, N, Q, F, W, Y, P, or C; C11 replaced with D, E, H, K. R, A, G, I, L, S, T, M, V, N, Q, F, W, Y, or P; L12 replaced with D, E, H, K, R, N, Q, F, W, Y, P, or C; W13 replaced with D, B, H, K, R, N, Q, A, G, I, L, S, T, M, V, P, or C; L14 replaced with D, E, H, K, R, N, Q, F, W, Y, P, or C; E15 replaced with H, K, R, A, G, I, L, S, T, M, V, N, Q, F, W, Y, P, or C; I16 replaced with D, E, H, K, R, N, Q, F, W, Y, P, or C; L17 replaced with D, E, H, K, R, N, Q, F, W, Y, P, or C; M18 replaced with D, E, H, K, R, N, Q, F, W, Y, P, or C; G19 replaced with D, E, H, K, R, N, Q, F, W, Y, P, or C; 120 replaced with D, E, H, K, R, N, Q, F, W, Y, P, or C; F21 replaced with D, E, H, K, R, N, Q, A, G, I, L, S, T, M, V, P, or C; I22 replaced with D, E, H, K, R, N, Q, F, W, Y, P, or C; A23 replaced with D, E, H, K, R, N, Q, F, W, Y, P, or C; G24 replaced with D, E, H, K, R, N, Q, F, W, Y, P, or C; T25 replaced with D, E, H, K, R, N, Q, F, W, Y, P, or C; L26 replaced with D, E, H, K, R, N, Q, F, W, Y, P, or C; S27 replaced with D, E, H, K, R, N, Q, F, WI Y, P, or C; L28 replaced with D, E, H, K, R, N, Q, F, W, Y, P, or C; D29 replaced with H, K, R, A, G, I, L, S, T, M, V, N, Q, F, W, Y, P, or C; C30 replaced with D, E, H, K, R, A, G, I, L, S, T, M, V, N, Q, F, W, Y, or P; N31 replaced with D, E, H, K, R, A, G, I, L, S, T, M, V, F, W, Y, P, or C; L32 replaced with D, E, H, K, R, N, Q, F, W, Y, P, or C; L33 replaced with D, E, H, K, R, N, Q, F, W, Y, P, or C; N34 replaced with D, E, H, K, R, A, G, I, L, S, T, M, V, F, W, Y, P, or C; V35 replaced with D, E, H, K, R, N, Q, F, W, Y, P, or C; H36 replaced with D, E, A, G, I, L, S, T, M, V, N, Q, F, W, Y, P, or C; L37 replaced with D, E, H, K, R, N, Q, F, W, Y, P, or C; R38 replaced with D, E, A, G, I, L, S, T, M, V, N, Q, F, W, Y, P, or C; R39 replaced with D, E, A, G, I, L, S, T, M, V, N, Q, F, W, Y, P, or C; V40 replaced with D, E, H, K, R, N, Q, F, W, Y, P, or C; T41 replaced with D, E, H, K, R, N, Q, F, W, Y, P, or C; W42 replaced with D, E, H, K, R, N, Q, A, G, I, L, S, T, M, V, P, or C; Q43 replaced with D, E, H, K, R, A, G, I, L, S, T, M, V, F, W, Y, P, or C; N44 replaced with D, E, H, K, R, A, G, I, L, S, T, M, V, F, W, Y, P, or C; L45 replaced with D, E, H, K, R, N, Q, F, W, Y, P, or C; R46 replaced with D, E, A, G, I, L, S, T, M, V, N, Q, F, W, Y, P, or C; H47 replaced with D, E, A, G, I, L, S, T, M, V, N, Q, F, W, Y, P, or C; L48 replaced with D, E, H, K, R, N, Q, F, W, Y, P, or C; S49 replaced with D, E, H, K, R, N, Q, F, W, Y, P, or C; S50 replaced with D, E, H, K, R, N, Q, F, W, Y, P, or C; M51 replaced with D, E, H, K, R, N, Q, F, W, Y, P, or C; S52 replaced with D, E, H, K, R, N, Q, F, W, Y, P, or C; N53 replaced with D, E, H, K, R, A, G, I, L, S, T, M, V, F, W, Y, P, or C; S54 replaced with D, E, H, K, R, N, Q, F, W, Y, P, or C; F55 replaced with D, E, H, K, R, N, Q, A, G, I, L, S, T, M, V, P, or C; P56 replaced with D, E, H, K, R, A, G, I, L, S, T, M, V, N, Q, F, W, Y, or C; V57 replaced with D, E, H, K, R, N, Q, F, W, Y, P, or C; E58 replaced with H, K, R, A, G, I, L, S, T, M, V, N, Q, F, W, Y, P, or C; C59 replaced with D, E, H, K, R, A, G, I, L, S, T, M, V, N, Q, F, W, Y, or P; L60 replaced with D, E, H, K, R, N, Q, F, W, Y, P, or C; R61 replaced with D, E, A, G, I, L, S, T, M, V, N, Q, F, W, Y, P, or C; E62 replaced with H, K, R, A, G, I, L, S, T, M, V, N, Q, F, W, Y, P, or C; N63 replaced with D, E, H, K, R, A, G, I, L, S, T, M, V, F, W, Y, P, or C; I64 replaced with D, E, H, K, R, N, Q, F, W, Y, P, or C; A65 replaced with D, E, H, K, R, N, Q, F, W, Y, P, or C; F66 replaced with D, E, H, K, R, N, Q, A, G, I, L, S, T, M, V, P, or C; E67 replaced with H, K, R, A, G, I, L, S, T, M, V, N, Q, F, W, Y, P, or C; L68 replaced with D, E, H, K, R, N, Q, F, W, Y, P, or C; P69 replaced with D, E, H, K, R, A, G, I, L, S, T, M, V, N, Q, F, W, Y, or C; Q70 replaced with D, E, H, K, R, A, G, I, L, S, T, M, V, F, W, Y, P, or C; E71 replaced with H, K, R, A, G, I, L, S, T, M, V, N, Q, F, W, Y, P, or C; F72 replaced with D, E, H, K, R, N, Q, A, G, I, L, S, T, M, V, P, or C; L73 replaced with D, E, H, K, R, N, Q, F, W, Y, P, or C; Q74 replaced with D, E, H, K, R, A, G, I, L, S, T, M, V, F, W, Y, P, or C; Y75 replaced with D, E, H, K, R, N, Q, A, G, I, L, S, T, M, V, P, or C; T76 replaced with D, E, H, K, R, N, Q, F, W, Y, P, or C; Q77 replaced with D, E, H, K, R, A, G, I, L, S, T, M, V, F, W, Y, P, or C; P78 replaced with D, E, H, K, R, A, G, I, L, S, T, M, V, N, Q, F, W, Y, or C; M79 replaced with D, E, H, K, R, N, Q, F, W, Y, P, or C; K80 replaced with D, E, A, G, I, L, S, T, M, V, N, Q, F, W, Y, P, or C; R81 replaced with D, E, A, G, I, L, S, T, M, V, N, Q, F, W, Y, P. or C; D82 replaced with H, K, R, A, G, I, L, S, T, M, V, N, Q, F, W, Y, P, or C; I83 replaced with D, E, H, K, R, N, Q, F, W, Y, P, or C; K84 replaced with D, E, A, G, I, L, S, T, M, V, N, Q, F, W, Y, P, or C; K85 replaced with D, E, A, G, I, L, S, T, M, V, N, Q, F, W, Y, P, or C; A86 replaced with D, E, H, K, R, N, Q, F, W, Y, P, or C; F87 replaced with D, E, H, K, R, N, Q, A, G, I, L, S, T, M, V, P, or C; Y88 replaced with D, E, H, K, R, N, Q, A, G, I, L, S, T, M, V, P, or C; E89 replaced with H, K, R, A, G, I, L, S, T, M, V, N, Q, F, W, Y, P, or C; M90 replaced with D, E, H, K, R, N, Q, F, W, Y, P, or C; S91 replaced with D, E, H, K, R, N, Q, F, W, Y, P, or C; L92 replaced with D, E, H, K, R, N, Q, F, W, Y, P, or C; Q93 replaced with D, E, H, K, R, A, G, I, L, S, T, M, V, F, W, Y, P, or C; A94 replaced with D, E, H, K, R, N, Q, F, W, Y, P, or C; F95 replaced with D, E, H, K, R, N, Q, A, G, I, L, S, T, M, V, P, or C; N96 replaced with D, E, H, K, R, A, G, I, L, S, T, M, V, F, W, Y, P, or C; I97 replaced with D, E, H, K, R, N, Q, F, W, Y, P, or C; F98 replaced with D, E, H, K, R, N, Q, A, G, I, L, S, T, M, V, P, or C; S99 replaced with D, E, H, K, R, N, Q, F, W, Y, P, or C; Q100 replaced with D, E, H, K, R, A, G, I, L, S, T, M, V, F, W, Y, P, or C; H101 replaced with D, E, A, G, I, L, S, T, M, V, N, Q, F, W, Y, P, or C; T102 replaced with D, E, H, K, R, N, Q, F, W, Y, P, or C; F103 replaced with D, E, H, K, R, N, Q, A, G, I, L, S, T, M, V, P, or C; K104 replaced with D, E, A, G, I, L, S, T, M, V, N, Q, F, W, Y, P, or C; Y105 replaced with D, E, H, K, R, N, Q, A, G, I, L, S, T, M, V, P, or C; W106 replaced with D, E, H, K, R, N, Q, A, G, I, L, S, T, M, V, P, or C; K107 replaced with D, E, A, G, I, L, S, T, M, V, N, Q, F, W, Y, P, or C; E108 replaced with H, K, R, A, G, I, L, S, T, M, V, N, Q, F, W, Y, P, or C; R109 replaced with D, E, A, G, I, L, S, T, M, V, N, Q, F, W, Y, P, or C; H110 replaced with D, E, A,G, I, L, S, T, M, V, N, Q, F, W, Y, P, or C; L111 replaced with D, E, H, K, R, N, Q, F, W, Y, P, or C; K112 replaced with D, E, A, G, I, L, S, T, M, V, N, Q, F, W, Y, P, or C; Q113 replaced with D, E, H, K, R, A, G, I, L, S, T, M, V, F, W, Y, P, or C; I114 replaced with D, E, H, K, R, N, Q, F, W, Y, P, or C; Q115 replaced with D, E, H, K, R, A, G, I, L, S, T, M, V, F, W, Y, P, or C; I116 replaced with D, E, H, K, R, N, Q, F, W, Y, P, or C; G117 replaced with D, E, H, K, R, N, Q, F, W, Y, P, or C; L118 replaced with D, E, H, K, R, N, Q, F, W, Y, P, or C; D119 replaced with H, K, R, A, G, I, L, S, T, M, V, N, Q, F, W, Y, P, or C; Q120 replaced with D, E, H, K, R, A, G, I, L, S, T, M, V, F, W, Y, P, or C; Q121 replaced with D, E, H, K, R, A, G, I, L, S, T, M, V, F, W, Y, P, or C; A122 replaced with D, E, H, K, R, N, Q, F, W, Y, P, or C; E123 replaced with H, K, R, A, G, I, L, S, T, M, V, N, Q, F, W, Y, P, or C; Y124 replaced with D, E, H, K, R, N, Q, A, G, I, L, S, T, M, V, P, or C; L125 replaced with D, E, H, K, R, N, Q, F, W, Y, P, or C; N126 replaced with D, E, H, K, R, A, G, I, L, S, T, M, V, F, W, Y, P, or C; Q127 replaced with D, E, H, K, R, A, G, I, L, S, T, M, V, F, W, Y, P, or C; C128 replaced with D, E, H, K, R, A, G, I, L, S, T, M, V, N, Q, F, W, Y, or P; L129 replaced with D, E, H, K, R, N, Q, F, W, Y, P, or C; E130 replaced with H, K, R, A, G, I, L, S, T, M, V, N, Q, F, W, Y, P, or C; E131 replaced with H, K, R, A, G, I, L, S, T, M, V, N, Q, F, W, Y, P, or C; D132 replaced with H, K, R, A, G, I, L, S, T, M, V, N, Q, F, W, Y, P, or C; E133 replaced with H, K, R, A, G, I, L, S, T, M, V, N, Q, F, W, Y, P, or C; N134 replaced with D, E, H, K, R, A, G, I, L, S, T, M, V, F, W, Y, P, or C; E135 replaced with H, K, R, A, G, I, L, S, T, M, V, N, Q, F, W, Y, P, or C; N136 replaced with D, E, H, K, R, A, G, I, L, S, T, M, V, F, W, Y, P, or C; E137 replaced with H, K, R, A, G, I, L, S, T, M, V, N, Q, F, W, Y, P, or C; D138 replaced with H, K, R, A, G, I, L, S, T, M, V, N, Q, F, W, Y, P, or C; M139 replaced with D, E, H, K, R, N, Q, F, W, Y, P, or C; K140 replaced with D, E, A, G, I, L, S, T, M, V, N, Q, F, W, Y, P, or C; E141 replaced with H, K, R, A, G, I, L, S, T, M, V, N, Q, F, W, Y, P, or C; M142 replaced with D, E, H, K, R, N, Q, F, W, Y, P, or C; K143 replaced with D, E, A, G, I, L, S, T, M, V, N, Q, F, W, Y, P, or C; E144 replaced with H, K, R, A, G, I, L, S, T, M, V, N, Q, F, W, Y, P, or C; N145 replaced with D, E, H, K, R, A, G, I, L, S, T, M, V, F, W, Y, P, or C; E146 replaced with H, K, R, A, G, I, L, S, T, M, V, N, Q, F, W, Y, P, or C; M147 replaced with D, E, H, K, R, N, Q, F, W, Y, P, or C; K148 replaced with D, E, A, G, I, L, S, T, M, V, N, Q, F, W, Y, P, or C; P149 replaced with D, E, H, K, R, A, G, I, L, S, T, M, V, N, Q, F, W, Y, or C; S150 replaced with D, E, H, K, R, N, Q, F, W, Y, P, or C; E151 replaced with H, K, R, A, G, I, L, S, T, M, V, N, Q, F, W, Y, P, or C; A152 replaced with D, E, H, K, R, N, Q, F, W, Y, P, or C; R153 replaced with D, E, A, G, I, L, S, T, M, V, N, Q, F, W, Y, P, or C; V154 replaced with D, E, H, K, R, N, Q, F, W, Y, P, or C; P155 replaced with D, E, H, K, R, A, G, I, L, S, T, M, V, N, Q, F, W, Y, or C; Q156 replaced with D, E, H, K, R, A, G, I, L, S, T, M, V, F, W, Y, P, or C; L157 replaced with D, E, H, K, R, N, Q, F, W, Y, P, or C; S158 replaced with D, E, H, K, R, N, Q, F, W, Y, P, or C; S159 replaced with D, E, H, K, R, N, Q, F, W, Y, P, or C; L160 replaced with D, E, H, K, R, N, Q, F, W, Y, P, or C; E161 replaced with H, K, R, A, G, I, L, S, T, M, V, N, Q, F, W, Y, P, or C; L162 replaced with D, E, H, K, R, N, Q, F, W, Y, P, or C; R163 replaced with D, E, A, G, I, L, S, T, M, V, N, Q, F, W, Y, P, or C; R164 replaced with D, E, A, G, I, L, S, T, M, V, N, Q, F, W, Y, P, or C; Y165 replaced with D, E, H, K, R, N, Q, A, G, I, L, S, T, M, V, P, or C; F166 replaced with D, E, H, K, R, N, Q, A, G, I, L, S, T, M, V, P, or C; H167 replaced with D, E, A, G, I, L, S, T, M, V, N, Q, F, W, Y, P, or C; R168 replaced with D, E, A, G, I, L, S, T, M, V, N, Q, F, W, Y, P, or C; I169 replaced with D, E, H, K, R, N, Q, F, W, Y, P, or C; D170 replaced with H, K, R, A, G, I, L, S, T, M, V, N, Q, F, W, Y, P, or C; N171 replaced with D, E, H, K, R, A, G, I, L, S, T, M, V, F, W, Y, P, or C; F172 replaced with D, E, H, K, R, N, Q, A, G, I, L, S, T, M, V, P, or C; L173 replaced with D, E, H, K, R, N, Q, F, W, Y, P, or C; K174 replaced with D, E, A, G, I, L, S, T, M, V, N, Q, F, W, Y, P, or C; E175 replaced with H, K, R, A, G, I, L, S, T, M, V, N, Q, F, W, Y, P, or C; K176 replaced with D, E, A, G, I, L, S, T, M, V, N, Q, F, W, Y, P, or C; K177 replaced with D, E, A, G, I, L, S, T, M, V, N, Q, F, W, Y, P, or C; Y178 replaced with D, E, H, K, R, N, Q, A, G, I, L, S, T, M, V, P, or C; S179 replaced with D, E, H, K, R, N, Q, F, W, Y, P, or C; D180 replaced with H, K, R, A, G, I, L, S, T, M, V, N, Q, F, W, Y, P, or C; C181 replaced with D, E, H, K, R, A, G, I, L, S, T, M, V, N, Q, F, W, Y, or P; A182 replaced with D, E, H, K, R, N, Q, F, W, Y, P, or C; W183 replaced with D, E, H, K, R, N, Q, A, G, I, L, S, T, M, V, P, or C; E184 replaced with H, K, R, A, G, I, L, S, T, M, V, N, Q, F, W, Y, P, or C; I185 replaced with D, E, H, K, R, N, Q, F, W, Y, P, or C; V186 replaced with D, E, H, K, R, N, Q, F, W, Y, P, or C; R187 replaced with D, E, A, G, I, L, S, T, M, V, N, Q, F, W, Y, P, or C; V188 replaced with D, E, H, K, R, N, Q, F, W, Y, P, or C; E189 replaced with H, K, R, A, G, I, L, S, T, M, V, N, Q, F, W, Y, P, or C; I190 replaced with D, E, H, K, R, N, Q, F, W, Y, P, or C; R191 replaced with D, E, A, G, I, L, S, T, M, V, N, Q, F, W, Y, P, or C; R192 replaced with D, E, A, G, I, L, S, T, M, V, N, Q, F, W, Y, P, or C; C193 replaced with D, E, H, K, R, A, G, I, L, S, T, M, V, N, Q, F, W, Y, or P; L194 replaced with D, E, H, K, R, N, Q, F, W, Y, P, or C; Y195 replaced with D, E, H, K, R, N, Q, A, G, I, L, S, T, M, V, P, or C; Y196 replaced with D, E, H, K, R, N, Q, A, G, I, L, S, T, M, V, P, or C; F197 replaced with D, E, H, K, R, N, Q, A, G, I, L, S, T, M, V, P, or C; Y198 replaced with D, E, H, K, R, N, Q, A, G, I, L, S, T, M, V, P, or C; K199 replaced with D, E, A, G, I, L, S, T, M, V, N, Q, F, W, Y, P, or C; F200 replaced with D, E, H, K, R, N, Q, A, G, I, L, S, T, M, V, P, or C; T201 replaced with D, E, H, K, R, N, Q, F, W, Y, P, or C; A202 replaced with D, E, H, K, R, N, Q, F, W, Y, P, or C; L203 replaced with D, E, H, K, R, N, Q, F, W, Y, P, or C; F204 replaced with D, E, H, K, R, N, Q, A, G, I, L, S, T, M, V, P, or C; R205 replaced with D, E, A, G, I, L, S, T, M, V, N, Q, F, W, Y, P, or C; R206 replaced with D, E, A, G, I, L, S, T, M, V, N, Q, F, W, Y, P, or C; and/or K207 replaced with D, E, A, G, I, L, S, T, M, V, N, Q, F, W, Y, P, or C in SEQ ID NO:2.

The resulting constructs can be routinely screened for activities or functions described throughout the specification and known in the art. Preferably, the resulting constructs have an increased and/or decreased KDI activity or function, while the remaining KDI activities or functions are maintained. More preferably, the resulting constructs have more than one increased and/or decreased KDI activity or function, while the remaining KDI activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of KDI protein, as well as the N- and C-terminal deletion mutants, having the general formula m-n, listed below.

A further embodiment of the invention relates to a polypeptide which comprises the amino acid sequence of a KDI polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a KDI polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIG. 1 or fragments thereof (e.g., the mature form and/or other fragments described herein), is 1–5, 5–10, 5–25, 5–50, 10–50 or 50–150, conservative amino acid substitutions are preferable.

Polypeptides and Fragments

The invention further provides an isolated KDI polypeptide having the amino acid sequence encoded by the deposited DNA, or the amino acid sequence in SEQ ID NO:2, or a peptide or polypeptide comprising a portion of the above polypeptides.

Variant and Mutant Polypeptides

To improve or alter the characteristics of KDI polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

In the present invention, a "polypeptide fragment" refers to an amino acid sequence which is a portion of that contained in SEQ ID NO:2 or encoded by the cDNA contained in the deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–27, 28–40, 41–60, 61–80, 81–100, 102–120, 121–140, 141–160, 161–180, or 181 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, since the protein of the invention is a member of the interferon polypeptide family, deletions of N-terminal amino acids up to the cysteine at position 59 as shown in SEQ ID NO:2 may retain some biological activity such as antiviral activity or inhibition of bone marrow proliferation. Polypeptides having further N-terminal deletions including the Cys-59 residue in SEQ ID NO:2 would not be expected to retain such biological activities because it is known that this residue in an interferon-related polypeptide is conserved among many, if not all, members of the family as is Leucine residue immediately adjacent to it (residue 60). The cysteine residue at position 59 is thought to be required for forming a disulfide bridge to provide structural stability which is needed for receptor binding and signal transduction.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete protein generally will be retained when less than the majority of the residues of the complete protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the KDI shown in SEQ ID NO:2, up to the Cys-59, and polynucleotides encoding such polypeptides. In particular, the present invention provides polypeptides comprising the amino acid sequence of residues n-207 of SEQ ID NO:2, where n is an integer in the range of 1–58 and where Cys-59 is the position of the first residue from the N-terminus of the complete KDI polypeptide (shown in SEQ ID NO:2) believed to be required for activity of the KDI protein.

More in particular, the invention provides polypeptides having the amino acid sequence of residues 1–207, 2–207, 3–207, 4–207, 5–207, 6–207, 7–207, 8–207, 9–207, 10–207, 11–207, 12–207, 13–207, 14–207, 15–207, 16–207, 17–207, 18–207, 19–207, 20–207, 21–207, 22–207, 23–207, 24–207, 25–207, 26–207, 27–207, 28–207, 29–207, 30–207, 31–207, 32–207, 33–207, 34–207, 35–207, 36–207, 37–207, 38–207, 39–207, 40–207, 41–207, 42–207, 43–207, 44–207, 45–207, 46–207, 47–207, 48–207, 49–207, 50–207, 51–207, 52–207, 53–207, 54–207, 55–207, 56–207, 57–207, and 58–207, all of SEQ ID NO:2. The preferred mature KDI polypeptide has amino acid sequend of residues Leu 28 to Lys 207 of SEQ ID NO:2. Polynucleotides encoding these polypeptides also are provided.

Preferred N- and C-terminal deletions are polypeptides having the amino acid sequence of residues 27–207, 23–207, 24–207, 30–207, 30–192, 30–182, 30–192 in which R192 is altered to K192, 28–192, 28–182, 30–199, 30–199 in which R192 is altered to K192, 30–193, in which C193 is altered to S193, 30–192 in which R192 is altered to K192, 30–207 in which R192 is altered to K192, 7–207, 30–207, 1–192, 27–207, 1–182, 7–182, 28–182, 30–182, 1–192, 7–192, 28–192, 30–192 of residues all of SEQ ID NO:2. Any of the described polypeptides and N- and C-terminal deletions of the polypeptides of the present invention may include any one or combination of the following alterations: R192 altered to K192, C193 altered to S193, C30 altered to S30, C59 altered to S59, C128 altered to S128, C181 altered to S181, N172 is altered to D172, the non-homologous loop region at residues 172–183 is deleted ("Lloop"), the non-homologous loop region at residues 173–184 is deleted ("Dloop"), the non-homologous loop region at residues 173–184 is deleted and N172 is altered to M172 ("Mloop"), and the non-homologous loop region at residues 173–184 is deleted ("Nloop"). Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Döbeli et al., *J. Biotechnology* 7:199–216 (1988). In the present case, since the protein of the invention is a member of the interferon polypeptide family, deletions of C-terminal amino acids up to the tryptophan residue at position 183 (W-183) in SEQ ID NO:2 may retain some biological activity, such as antiviral activity or inhibition of bone marrow proliferation. Polypeptides having further C-terminal deletions including Trp-183 of SEQ ID NO:2 may lose a biological activity because it is known that this residue in an interferon-related polypeptide is conserved among many members and is thought to be important for receptor binding and signal transduction. Furthermore, the cysteine residue at position 181 is highly conserved and known to be required for antiviral activity of members of the interferon family.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete protein generally will be retained when less than the majority of the residues of the complete protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the KDI shown in SEQ ID NO:2, up to Trp-183 of SEQ ID NO:2, and polynucleotides encoding such polypeptides. In particular, the present invention provides polypeptides having the amino acid sequence of residues 1-m of the amino acid sequence in SEQ ID NO:2, where m is any integer in the range of 182–207 and residue Trp-183 is the position of the first residue from the C-terminus of the complete KDI polypeptide (shown in SEQ ID NO:2) believed to be required for activity of the KDI protein.

More in particular, the invention provides polypeptides having the amino acid sequence of residues 1–182, 1–183, 1–184, 1–185, 1–186, 1–187, 1–188, 1–189, 1–190, 1–191, 1–192, 1–193, 1–194, 1–195, 1–196, 1–197, 1–198, 1–199, 1–200, 1–201, 1–203, 1–204, 1–205, 1–206 and 1–207 of SEQ ID NO:2. Polynucleotides encoding these polypeptides also are provided.

The invention also provides polypeptides having one or more amino acids deleted from both the amino and the carboxyl termini, which may be described generally as having residues n-m of SEQ ID NO:2, where n and m are integers as described above. Furthermore, the invention provides these mutant polypeptides optionally having an N-terminal methionine. The polypeptides may therefore also be described by the formula x-n-m where X is either $NH_2$ or Met and n and m are integers as described above. Polynucleotides encoding these polypeptides are, of course, also provided.

More in particular, the invention preferably provides polypeptides having the amino acid sequence of residues: 20–183, 21–183, 22–183, 23–183, 24–183, 25–183, 26–183, 27–183, 28–183, 29–183, 30–183, 31–183, 32–183, 33–183, 34–183, 35–183, 36–183, 37– 38–183, 39–183, 40–183, 41–183, 42–183, 43–183, 44–183, 45–183, 46–183, 47–183, 48–183, 49–183, 50–183, 51–183, 52–183, 53–183, 54–183, 55–183, 56–183, 57–183, 58–183, 59–183, 20–184, 21–184, 22–184, 23–184, 24–184, 25–184, 26–184, 27–184, 28–184, 29–184, 30–184, 31–184, 32–184, 33–184, 34–184, 35–184, 36–184, 37–184, 38–184, 39–184, 40–184, 41–184, 42–184, 43–184, 44–184, 45–184, 46–184, 47–184, 48–184, 49–184, 50–184, 51–184, 52–184, 53–184, 54–184, 55–184, 56–184, 57–184, 58–184, 59–184, 20–185, 21–185, 22–185, 23–185, 24–185, 25–185, 26–185, 27–185, 28–185, 29–185, 30–185, 31–185, 32–185, 33–185, 34–185, 35–185, 36–185, 37–185, 38–185, 39–185, 40–185, 41–185, 42–185, 43–185, 44–185, 45–185, 46–185, 47–185, 48–185, 49–185, 50–185, 51–185, 52–185, 53–185, 54–185, 55–185, 56–185, 57–185, 58–185, 59–185, 20–186, 21–186, 22–186, 23–186, 24–186, 25–186, 26–186, 27–186, 28–186, 29–186, 30–186, 31–186, 32–186, 33–186, 34–186, 35–186, 36–186, 37–186, 38–186, 39–186, 40–186, 41–186, 42–186, 43–186 44–186, 45–186, 46–186, 47–186, 48–186, 49–186, 50–186, 51–186, 52–186, 53–186, 54–186, 55–186, 56–186, 57–186, 58–186, 59–186, 20–187, 21–187, 22–187, 23–187, 24–187, 25–187, 26–187, 27–187, 28–187, 29–187, 30–187, 31–187, 32–187, 33–187, 34–187, 35–187, 36–187, 37–187, 38–187, 39–187, 40–187, 41–187, 42–187, 43–187, 44–187, 45–187, 46–187, 47–187, 48–187, 49–187, 50–187, 51–187, 52–187, 53–187, 54–187, 55–187, 56–187, 57–187, 58–187, 59–187, 20–188, 21–188, 22–188, 23–188, 24–188, 25–188, 26–188, 27–188, 28–188, 29–188, 30–188, 31–188, 32–188, 33–188, 34–188, 35–188, 36–188, 37–188, 38–188, 39–188, 40–188, 41–188, 42–188, 43–188, 44–188, 45–188, 46–188, 47–188, 48–188, 49–188, 50–188, 51–188, 52–188, 53–188, 54–188, 55–188, 56–188, 57–188, 58–188, 59–188, 20–189, 21–189, 22–189, 23–189, 24–189, 25–189, 26–189, 27–189, 28–189, 29–189, 30–189, 31–189, 32–189, 33–189, 34–189, 35–189, 36–189, 37–189, 38–189, 39–189, 40–189, 41–189, 42–189, 43–189, 44–189, 45–189, 46–189, 47–189, 48–189, 49–189, 50–189, 51–189, 52–189, 53–189, 54–189, 55–189, 56–189, 57–189, 58–189, 59–189, 20–190, 21–190, 22–190, 23–190, 24–190, 25–190, 26–190, 27–190, 28–190, 29–190, 30–190, 31–190, 32–190, 33–190, 34–190, 35–190, 36–190, 37–190, 38–190, 39–190, 40–190, 41–190, 42–190, 43–190, 44–190, 45–190, 46–190, 47–190, 48–190, 49–190, 50–190, 51–190, 52–190, 53–190, 54–190, 55–190, 56–190, 57–190, 58–190, 59–190, 20–191, 21–191, 22–191, 23–191, 24–191, 25–191, 26–191, 27–191, 28–191, 29–191, 30–191, 31–191, 32–191, 33–191, 34–191, 35–191, 36–191, 37–191, 38–191, 39–191, 40–191, 41–191, 42–191, 43–191, 44–191, 45–191, 46–191, 47–191, 48–191, 49–191, 50–191, 51–191, 52–191, 53–191, 54–191, 55–191, 56–191, 57–191, 58–191, 59–191, 20–192, 21–192, 22–192, 23–192, 24–192, 25–192, 26–192, 27–192, 28–192, 29–192, 30–192, 31–192, 32–192, 33–192, 34–192, 35–192, 36–192, 37–192, 38–192, 39–192, 40–192, 41–192, 42–192, 43–192, 44–192, 45–192, 46–192, 47–192, 48–192, 49–192, 50–192, 51–192, 52–192, 53–192, 54–192, 55–192, 56–192, 57–192, 58–192, 59–192, 20–193, 21–193, 22–193, 23–193, 24–193, 25–193, 26–193, 27–193, 28–193, 29–193, 30–193, 31–193, 32–193, 33–193, 34–193, 35–193, 36–193, 37–193, 38–193, 39–193, 40–193, 41–193, 42–193, 43–193, 44–193, 45–193, 46–193, 47– 193, 48–193, 49–193, 50–193, 51–193, 52–193, 53–193, 54–193, 55–193, 56–193, 57–193, 58–193, 59–193, 20–194, 21–194, 22–194, 23–194, 24–194, 25–194, 26–194, 27–194, 28–194, 29–194, 30–194, 31–194, 32–194, 33–194, 34–194, 35–194, 36–194, 37–194, 38–194, 39–194, 40–194, 41–194, 42–194, 43–194, 44–194, 45–194, 46–194, 47–194, 48–194, 49–194, 50–194, 51–194, 52–194,53–194, 54–194, 55–194, 56–194, 57–194, 58–194, 59–194, 20–195, 21–195, 22–195, 23–195, 24–195, 25–195, 26–195, 27–195, 28–195, 29–195, 30–195, 31–195, 32–195, 33–195, 34–195, 35–195, 36–195, 37–195, 38–195, 39–195, 40–195, 41–195, 42–195, 43–195, 44–195, 45–195, 46–195, 47–195, 48–195, 49–195, 50–195, 51–195, 52–195, 53–195, 54–195, 55–195, 56–195, 57–195, 58–195, 59–195, 20–196, 21–196, 22–196, 23–196, 24–196, 25–196, 26–196, 27–196, 28–196, 29–196, 30–196, 31–196, 32–196, 33–196, 34–196, 35–196, 36–196, 37–196, 38–196, 39–196, 40–196, 41–196, 42–196, 43–196, 44–196, 45–196, 46–196, 47–196, 48–196, 49–196, 50–196, 51–196, 52–196, 53–196, 54–196, 55–196, 56–196, 57–196, 58–196, 59–196, 20–197, 21–197, 22–197, 23–197, 24–197, 25–197, 26–197, 27–197, 28–197, 29–197, 30–197, 31–197, 32–197, 33–197, 34–197, 35–197, 36–197, 37–197, 38–197, 39–197, 40–197, 41–197, 42–197, 43–197, 44–197, 45–197, 46–197, 47–197, 48–197, 49–197, 50–197, 51–197, 52–197, 53–197, 54–197, 55–197, 56–197, 57–197, 58–197, 59–197, 20–198, 21–198, 22–198, 23–198, 24–198, 25–198, 26–198, 27–198, 28–198, 29–198, 30–198, 31–198, 32–198, 33–198, 34–198, 35–198, 36–198, 37–198, 38–198, 39–198, 40–198, 41–198, 42–198, 43–198, 44–198, 45–198, 46–198, 47–198, 48–198, 49–198, 50–198, 51–198, 52–198, 53–198, 54–198, 55–198, 56–198, 57–198, 58–198, 59–198, 20–199, 21–199, 22–199, 23–199, 24–199, 25–199, 26–199, 27–199, 28–199, 29–199, 30–199, 31–199, 32–199, 33–199, 34–199, 35–199, 36–199, 37–199, 38–199, 39–199, 40–199, 41–199, 42–199, 43–199, 44–199, 45–199, 46–199, 47–199, 48–199, 49–199, 50–199, 51–199, 52–199, 53–199, 54–199, 55–199, 56–199, 57–199, 58–199, 59–25 199, 20–200, 21–200, 22–200, 23–200, 24–200, 25–200, 26–200, 27–200, 28–200, 29–200, 30–200, 31–200, 32–200, 33–200, 34–200, 35–200, 36–200, 37–200, 38–200, 39–200, 40–200, 41–200, 42–200, 43–200, 44–200, 45–200, 46–200, 47–200, 48–200, 49–200, 50–200, 51–200, 52–200, 53–200, 54–200, 55–200, 56–200, 57–200, 58–200, 59–200, 20–201, 21–201, 22–201, 23–201, 24–201, 25–201, 26–201, 27–201, 28–201, 29–201, 30–201, 31–201, 32–201, 33–201, 34–201, 35–201, 36–201, 37–201, 38–201, 39–201, 40–201, 41–201, 42–201, 43–201, 44–201, 45–201, 46–201, 47–201, 48–201, 49–201, 50–201, 51–201, 52–201, 53–201, 54–201, 55–201, 56–201, 57–201, 58–201, 59–201, 20–202, 21–202, 22–202, 23–202, 24–202, 25–202, 26–202, 27–202, 28–202, 29–202, 30–202, 31–202, 32–202, 33–202, 34–202, 35–202, 36–202, 37–202, 38–202, 39–202, 40–202, 41–202, 42–202, 43–202, 44–202, 45–202, 46–202, 47–202, 48–202, 49–202, 50–202, 51–202, 52–202, 53–202, 54–202, 55–202, 56–202, 57–202, 58–202, 59–202, 20–203, 21–203, 22–203, 23–203, 24–203, 25–203, 26–203, 27–203, 28–203, 29–203, 30–203, 31–203, 32–203, 33–203, 34–203, 35–203, 36–203, 37–203, 38–203, 39–203, 40–203, 41–203, 42–203, 43–203, 44–203, 45–203, 46–203, 47–203, 48–203, 49–203, 50–203, 51–203, 52–203, 53–203, 54–203, 55–203, 56–203, 57–203, 58–203, 59–203, 20–204, 21–204, 22–204, 23–204, 24–204, 25–204, 26–204, 27–204, 28–204, 29–204, 30–204, 31–204, 32–204, 33–204, 34–204, 35–204, 36–204, 37–204, 38–204, 39–204, 40–204, 41–204, 42–204, 43–204, 44–204, 45–204, 46–204, 47–204, 48–204, 49–204, 50–204, 51–204, 52–204, 53–204, 54–204, 55–204, 56–204, 57–204, 58–204, 59–204, 20–205, 21–205, 22–205, 23–205, 24–205, 25–205, 26–205, 27–205, 28–205, 29–205, 30–205, 31–205, 32–205, 33–205, 34–205, 35–205, 36–205, 37–205, 38–205, 39–205, 40–205, 41–205, 42–205, 43–205, 44–205, 45–205, 46–205, 47–205, 48–205, 49–205, 50–205, 51–205, 52–205, 53–205, 54–205, 55–205, 56–205, 57–205, 58–205, 59–205, 20–206, 21–206, 22–206, 23–206, 24–206, 25–206, 26–206, 27–206, 28–206, 29–206, 30–206, 31–206, 32–206, 33–206, 34–206, 35–206, 36–206, 37–206, 38–206, 39–206, 40–206, 41–206, 42–206, 43–206, 44–206, 45–206, 46–206, 47–206, 48–206, 49–206, 50–206, 51–206, 52–206, 53–206, 54–206, 55–206, 56–206, 57–206, 58–206 and 59–206 of SEQ ID NO:2. Each of the foregoing polypeptides may additionally include an N-terminal methionine residue. Polynucleotides encoding each of these polypeptides, with or without an N-terminal methionine residues are also are provided.

Also included are polypeptides consisting of a portion of the complete KDI amino acid sequence encoded by the human cDNA in clone HKAPI15, where this portion excludes from 1to about 58 amino acids from the amino terminus of the complete amino acid sequence encoded by the human cDNA in clone HKAPI15, or from 1 to about 24 amino acids from the carboxy terminus, or any combination of the above amino terminal and carboxy terminal deletions, of the complete amino acid sequence encoded by the human cDNA in clone HKAPI15. Polynucleotides encoding all of the above deletion mutant polypeptide forms also are provided.

Particularly, N-terminal deletions of the KDI polypeptide can be described by the general formula m-207, where m is an integer from 2 to 202, where m corresponds to the position of the amino acid residue identified in SEQ ID NO:2. More in particular, the invention provides polynucleotides encoding polypeptides comprising, or alternatively consisting of, the amino acid sequence of residues: S-2 to K-207; T-3 to K-207; K-4 to K-207; P-5 to K-207; D-6 to K-207; M-7 to K-207; I-8 to K-207; Q-9 to K-207; K-207; C-11 to K-207; L-12 to K-207; W-13 to K-207; L-14 to K-207; E-15 to K-207; I-16 to K-207; L-17 to K-207; M-18 to K-207; G-19 to K-207; I-20 to K-207; F-21 to K-207; I-22 to K-207; A-23 to K-207; G-24 to K-207; T-25 to K-207; L-26 to K-207; S-27 to K-207; L-28 to K-207; D-29 to K-207; C-30 to K-207; N-31 to K-207; L-32 to K-207; L-33 to K-207; N-34 to K-207; V-35 to K-207; H-36 to K-207; L-37 to K-207; R-38 to K-207; R-39 to K-207; V-40 to K-207; T-41 to K-207; W-42 to K-207; Q-43 to K-207; N-44 to K-207; L-45 to K-207; R-46 to K-207; H-47 to K-207; L-48 to K-207; S-49 to K-207; S-50 to K-207; M-51 to K-207; S-52 to K-207; N-53 to K-207; S-54 to K-207; F-55 to K-207; P-56 to K-207; V-57 to K-207; E-58 to K-207; C-59 to K-207; L-60 to K-207; R-61 to K-207; E-62 to K-207; N-63 to K-207; 1–64 to K-207; A-65 to K-207; F-66 to K-207; E-67 to K-207; L-68 to K-207; P-69 to K-207; Q-70 to K-207; E-71 to K-207; F-72 to K-207; L-73 to K-207; Q-74 to K-207; Y-75 to K-207; T-76 to K-207; Q-77 to K-207; P-78 to K-207; M-79 to K-207; K-80 to K-207; R-81 to K-207; D-82 to K-207; 1–83 to K-207; K-84 to K-207; K-85 to K-207; A-86 to K-207; F-87 to K-207; Y-88 to K-207; E-89 to K-207; M-90 to K-207; S-91 to K-207; L-92 to K-207; Q-93 to K-207; A-94 to K-207; F-95 to K-207; N-96 to K-207; 1–97 to K-207; F-98 to K-207; S-99 to K-207; Q-100 to K-207; H-101 to K-207; T-102 to K-207; F-103 to K-207; K-104 to K-207; Y-105 to K-207; W-106 to K-207; K-107 to K-207; E-108 to K-207; R-109 to K-207; H-110 to K-207; L-111 to K-207; K-112 to K-207; Q-113 to K-207; I-114 to K-207; Q-115 to K-207; I-116 to K-207; G-117 to K-207; L-118 to K-207; D-119 to K-207; Q-120 to K-207; Q-121 to K-207; A-122 to K-207; E-123 to K-207; Y-124 to K-207; L-125 to K-207; N-126 to K-207; Q-127 to K-207; C-128 to K-207; L-129 to K-207; E-130 to K-207; E-131 to K-207; D-132 to K-207; E-133 to K-207; N-134 to K-207; E-135 to K-207; N-136 to K-207; E-137 to K-207; D-138 to K-207; M-139 to K-207; K-140 to K-207; E-141 to K-207; M-142 to K-207; K-143 to K-207; E-144 to K-207; N-145 to K-207; E-146 to K-207; M-147 to K-207; K-148 to K-207; P-149 to K-207; S-150 to K-207; E-151 to K-207; A-152 to K-207; R-153 to K-207; V-154 to K-207; P-155 to K-207; Q-156 to K-207; L-157 to K-207; S-158 to K-207; S-159 to K-207; L-160 to K-207; E-161 to K-207; L-162 to K-207; R-163 to K-207; R-164 to K-207; Y-165 to K-207; F-166 to K-207; H-167 to K-207; R-168 to K-207; I-169 to K-207; D-170 to K-207; N-171 to K-207; F-172 to K-207; L-173 to K-207; K-174 to K-207; E-175 to K-207; K-176 to K-207; K-177 to K-207; Y-178 to K-207; S-179 to K-207; D-180 to K-207; C-181 to K-207; A-182 to K-207; W-183 to K-207; E-184 to K-207; 1–185 to K-207; V-186 to K-207; R-187 to K-207; V-188 to K-207; E-189 to K-207; 1–190 to K-207; R-191 to K-207; R-192 to K-207; C-193 to K-207; L-194 to K-207; Y-195 to K-207; Y-196 to K-207; F-197 to K-207; Y-198 to K-207; K-199 to K-207; F-200 to K-207; T-201 to K-207; and/or A-202 to K-207 of SEQ ID NO:2. Polynucleotides encoding these polypeptides are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the KDI polypeptide described above. The present invention also encompasses the above polynucleotide sequences fused to a heterologous polynucleotide sequence.

Also as mentioned above, even if deletion of one or more amino acids from the C-terminus of a protein results in modification of loss of one or more biological functions of the protein, other functional activities (e.g., biological activities, ability to multimerize, ability to bind KDI ligand) may still be retained. For example the ability of the shortened KDI mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an KDI mutein with a large number of deleted C-terminal amino acid residues may retain some biological or immunogenic activities. In fact, peptides composed of as few as six KDI amino acid residues may often evoke an immune response.

Accordingly, the present invention further provides polypeptides having one or more residues deleted from the carboxy terminus of the amino acid sequence of the KDI polypeptide shown in FIG. 1 (SEQ ID NO:2), as described by the general formula 1-n, where n is an integer from 6 to 206 where n corresponds to the position of amino acid residue identified in SEQ ID NO:2. More in particular, the invention provides polynucleotides encoding polypeptides comprising, or alternatively consisting of, the amino acid sequence of residues: M-1 to R-206; M-1 to R-205; M-1 to F-204; M-1 to L-203; M-1 to A-202; M-1 to T-201; M-1 to F-200; M-1 to K-199; M-1 to Y-198; M-l to F-197; M-1 Y-196; M-1 to Y-195; M-1 to L-194; M-1 to C-193; M-1 to R-192; M-1 to R-191; M-1 to I-190; M-1 to E-189; M-1 to V-188; M-1 to R-187; M-1 to V-186; M-1 to I-185; M-1 to E-184; M-1 to W-183; M-1 to A-182; M-1 to C-181; M-1 to D-180; M-1 to S-179; M-1 to Y-178; M-1 to K-177; M-1 to K-176; M-1 to E-175; M-1 to K-174; M-1 to L-173; M-1 to F-172; M-1 to N-171; M-1 to D-170; M-1 to 1–169; M-1 to R-168; M-1 to H-167; M-1 to 166; M-1 to Y-165; M-1 to R-164; M-1 to R-163; M-1 to L-162; M-1 to E-161; M-1 to L-160; M-1 to S-159; M-1 to S-158; M-1 to L-157; M-1 to Q-156; M-1 to P-155; M-1 to V-154; M-1 to R-153; M-1 to A-152; M-1 to E-151; M-1 to S-150; M-1 to P-149; M-1 to K-148; M-1 to M-147; M-1 to E-146; M-1 to N-145; M-1 to E-144; M-1 to K-143; M-1 to M-142; M-1 to E-141; M-1 to K-140; M-1 to M-139; M-1 to D-138; M-1 to E-137; M-1 to N-136; M-1 to E-135; M-1 to N-134; M-1 to E-133; M-1 to D-132; M-1 to E-131; M-1 to E-130; M-1 to L-129; M-1 to C-128; M-1 to Q-127; M-1 to N-126; M-1 to L-125; M-1 to Y-124; M-1 to E-123; M-1 to A-122; M-1 to Q-121; M-1 to Q-120; M-1 to D-119; M-1 to L-118; M-1 to G-117; M-1 to I-116; M-1 to Q-115; M-1 to I-114; M-1 to Q-113; M-1 to K-112; M-1 to L-111; M-1 to H-110; M-1 to R-109; M-1 to E-108; M-1 to K-107; M-1 to W-106; M-1 to Y-105; M-1 to K-104; M-1 to F-103; M-1 to T-102; M-1 to H-101; M-1 to Q-100; M-1 to S-99; M-1 to F-98; M-1 to I97; M-1 to N-96; M-1 to F-95; M-1 to A-94; M-1 to Q-93; M-1 to L-92; M-1 to S-91; M-1 to M-90; M-1 to E-89; M-1 to Y-88; M-1 to F-87 M-1 to A-86; M-1 to K-85; M-1 to K-84; M-1 to I83; M-1 to D-82; M-1 to R-81; M-1 to K-80; M-1 to M-79; M-1 to P-78; M-1 to Q-77; M-1 to T-76; M-1 to Y-75; M-1 to Q-74; M-1 to L-73; M-1 to F-72; M-1 to E-71; M-1 to Q-70; M-1 to P-69; M-1 to L-68; M-1 to E-67; M-1 to F-66; M-1 to A-65; M-1 to I64; M-1 to N-63; M-1 to E-62; M-1 to L-60; M-1 to C-59; M-1 to E-58; M-1 to V-57; M-1 to P-56; M-1 to F-55; M-1 to S-54; M-1 to N-53; M-1 to S-52; M-1 to M-51; M-1 to S-50; M-1 to S-49; M-1 to L-48; M-1 to H47; M-1 to R-46; M-1 to L-45; M-1 to N-44; M-1 to Q43; M-1 to W-42; M-1 to T41; M-1 to V-40; M-1 to R-39; M-1 to R-38; M-1 to L-37; M-1 to H-36; M-1 to V-35; M-1 to N-34; M-1 to L-33; M-1 to L-32; M-1 to N-31; M-1 to C-30; M-1 to D-29; M-1 to L-28; M-1 to S-27; M-1 to L-26; M-1 to T-25; M-1 to G-24; M-1 to A-23; M-1 to I22; M-1 to F-21; M-1 to I20; M-1 to G-19; M-1 to M-18; M-1 to L-17; M-1 to I-16; M-1 to E-15; M-1 to L-14; M-1 to W-13; M-1 to L-12; M-1 to C-11; M-1 to K-10; M-1 to Q-9; M-1 to I8; M-1 to M-7 of SEQ ID NO:2. Polynucleotides encoding these polypeptides are also encompassed by the invention.

Moreover, a signal sequence may be added to these C-terminal contructs. For example, amino acids 1–27 of SEQ ID NO:2, amino acids 2–27 of SEQ ID NO:2, amino acids 3–27 of SEQ ID NO:2, amino acids 4–27 of SEQ ID NO:2, amino acids 5–27 of SEQ ID NO:2, amino acids 6–27 of SEQ ID NO:2, amino acids 7–27 of SEQ ID NO:2, amino acids 8–27 of SEQ ID NO:2, amino acids 9–27 of SEQ ID NO:2, amino acids 10–27 of SEQ ID NO:2, amino acids 11–27 of SEQ I) NO:2, amino acids 12–27 of SEQ ID NO:2, amino acids 13–27 of SEQ ID NO:2, amino acids 14–27 of SEQ ID NO:2, amino acids 15–27 of SEQ ID NO:2, amino acids 16–27 of SEQ ID NO:2, amino acids 17–27 of SEQ ID NO:2, amino acids 18–27 of SEQ ID NO:2, amino acids 19–27 of SEQ ID NO:2, amino acids 20–27 of SEQ ID NO:2, amino acids 21–27 of SEQ ID NO:2, amino acids 22–27 of SEQ ID NO:2, amino acids 23–27 of SEQ ID NO:2, amino acids 24–27 of SEQ ID NO:2, amino acids 25–27 of SEQ ID NO:2, or amino acids 26–27 of SEQ ID NO:2 can be added to the N-terminus of each C-terminal constructs listed above.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the KDI polypeptide described above. The present invention also encompasses the above polynucleotide sequences fused to a heterologous polynucleotide sequence.

In addition, any of the above listed N- or C-terminal deletions can be combined to produce a N- and C-terminal deleted KDI polypeptide. The invention also provides polypeptides having one or more amino acids deleted from both the amino and the carboxyl termini, which may be described generally as having residues m-n of SEQ ID NO:2, where n and m are integers as described above. Polynucleotides encoding these polypeptides are also encompassed by the invention.

Also included are a nucleotide sequence encoding a polypeptide consisting of a portion of the complete KDI amino acid sequence encoded by the cDNA clone contained in ATCC Deposit No. 203500, where this portion excludes any integer of amino acid residues from 1 to about 197 amino acids from the amino terminus of the complete amino acid sequence encoded by the cDNA clone contained in ATCC Deposit No. 203500, or any integer of amino acid residues from 1 to about 197 amino acids from the carboxy terminus, or any combination of the above amino terminal and carboxy terminal deletions, of the complete amino acid sequence encoded by the cDNA clone contained in ATCC Deposit No. 203500. Polynucleotides encoding all of the above deletion mutant polypeptide forms also are provided.

The present application is also directed to proteins containing polypeptides at least 90%, 92%, 93%, 94%, 95%, 96%, 97%, 98% or 99% identical to the KDI polypeptide sequence set forth herein m-n. In preferred embodiments, the application is directed to proteins containing polypeptides at least 90%, 95%, 96%, 97%, 98% or 99% identical to polypeptides having the amino acid sequence of the specific KDI N- and C-terminal deletions recited herein. Polynucleotides encoding these polypeptides are also encompassed by the invention.

Additional preferred polypeptide fragments comprise, or alternatively consist of, the amino acid sequence of residues: M-1 to E-15; S-2 to 1–16; T-3 to L-17; K-4 to M-18; P-5 to G-19; D-6 to I20; M-7 to F-21; I8 to I22; Q-9 to A-23; K-10 to G-24; C-11 to T-25; L-12 to L-26; W-13 to S-27; L-14 to L-28; E-15 to D-29; I-16 to C-30; L-17 to N-31; M-18 to L-32; G-19 to L-33; I-20 to N-34; F-21 to V-35; I22 to H-36; A-23 to L-37; G-24 to R-38; T-25 to R-39; L-26 to V-40; S-27 to T-41; L-28 to W-42; D-29 to Q-43; C-30 to N-44; N-31 to L-45; L-32 to R-46; L-33 to H-47; N-34 to L-48; V-35 to S-49; H-36 to S-50; L-37 to M-51; R-38 to S-52; R-39 to N-53; V-40 to S-54; T-41 to F-55; W-42 to P-56; Q-43 to V-57; N-44 to E-58; L-45 to C-59; R-46 to L-60; H-47 to R-61; L-48 to E-62; S-49 to N-63; S-50 to I-64; M-51 to A-65; S-52 to F-66; N-53 to E-67; S-54 to L-68; F-55 to P-69; P-56 to Q-70; V-57 to E-71; E-58 to F-72; C-59 to L-73; L-60 to Q-74; R-61 to Y-75 E-62 to T-76; N-63 to Q-77; I-64 to P-78; A-65 to M-79; F-66 to K-80; E-67 to R-8 1; L-68 to D-82; P-82; P-69 to I-83; Q-70 to K-84; E-71 to K-85; F-72 to A-86; L-73 to F-87; Q-74 to Y-88; Y-75 to E-89; T-76 to M-90; Q-77 to S-91; P-78 to L-92; M-79 to Q-93; K-80 to A-94; R-81 to F-95; D-82 to N-96; I-83 to I97; K-84 to F-98; K-85 to S-99; A-86 to Q-100; F-87 to H-101; Y-88 to T-102; E-89 to F-103; M-90 to K-104; S-91 to Y-105; L-92 to W-106; Q-93 to K-107; A-94 to E-108; F-95 to R-109; N-96 to H-110; I-97 to L-111; F-98 to K-112; S-99 to Q-113; Q-100 to I-114; H-101 to Q-115; T-102 to I-116; F-103 to G-117; K-104 to L-118; Y-105 to D-119; W-106 to Q-120; K-107 to Q-121; E-108 to A-122; R-109 to E-123; H-110 to Y-124; L-111 to L-125; K-112 to N-126; Q-113 to Q-127; I-114 to C-128; Q-115 to L-129; I-116 to E-130; G-117 to E-131; L-118 to D-132; D-119 to E-133; Q-120 to N-134; Q-121 to E-135; A-122 to N-136; E-123 to E-137; Y-124 to D-138; L-125 to M-139; N-126 to K-140; Q-127 to E-141; C-128 to M-142; L-129 to K-143; E-130 to E-144; E-131 to N-145; D-132 to E-146;

E-133 to M-147; N-134 to K-148; E-135 to P-149; N-136 to S-150; E-137 to E-151; D-138 to A-152; M-139 to R-153; K-140 to V-154; E-141 to P-155; M-142 to Q-156; K-143 to L-157; E-144 to S-158; N-145 to S-159; E-146 to L-160; M-147 to E-161; K-148 to L-162; P-149 to R-163; S-150 to R-164; E-151 to Y-165; A-152 to F-166; R-153 to H-167; V-154 to R-168; P-155 to I-169; Q-156 to D-170; L-157 to N-171; S-158 to F-172; S-159 to L-173; L-160 to K-174; E-161 to E-175; L-162 to K-176; R-163 to K-177; R-164 to Y-178; Y-165 to S-179: F-166 to D-180; H-167 to C-181; R-168 to A-182; I-169 to W-183; D-170 to E-184; N-171 to I-185; F-172 to V-186; L-173 to R-187; K-174 to V-188; E-175 to E-189; K-176 to I-190; K-177 to R-191; Y-178 to R-192; S-179 to C-193; D-180 to L-194; C-181 to Y-195; A-182 to Y-196; W-183 to F-197; E-184 to Y-198; I-185 to K-199; V-186 to F-200; R-187 to T-201; V-188 to A-202; E-189 to L-203; I-190 to F-204; R-191 to R-205; R-192 to R-206; and/or C-193 to K-207 of SEQ ID NO:2. These polypeptide fragments may retain the biological activity of KDI polypeptides of the invention and/or may be useful to generate or screen for antibodies, as described further below. Polynucleotides encoding these polypeptide fragments are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the KDI polypeptide described above. The present invention also encompasses the above polynucleotide sequences fused to a heterologous polynucleotide sequence.

Additionally, the present application is also directed to proteins containing polypeptides at least 90%, 92%, 93%, 94%, 95%, 96%, 97%, 98% or 99% identical to the KDI polypeptide fragments set forth above. Polynucleotides encoding these polypeptides are also encompassed by the invention.

Preferably, the polynucleotide fragments of the invention encode a polypeptide which demonstrates a KDI functional activity. By a polypeptide demonstrating a KDI "functional activity" is meant, a polypeptide capable of displaying one or more known functional activities associated with a full-length (complete) KDI protein. Such functional activities include, but are not limited to, biological activity, antigenicity [ability to bind (or compete with a KDI polypeptide for binding) to an anti-KDI antibody], immunogenicity (ability to generate antibody which binds to a KDI polypeptide), ability to form multimers with KDI polypeptides of the invention, and ability to bind to a receptor or ligand for a KDI polypeptide.

The functional activity of KDI polypeptides, and fragments, variants derivatives, and analogs thereof, can be assayed by various methods.

For example, in one embodiment where one is assaying for the ability to bind or compete with full-length KDI polypeptide for binding to anti-KDI antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a KDI ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of KDI binding to its substrates (signal transduction) can be assayed.

In addition, assays described herein (see Examples) and otherwise known in the art may routinely be applied to measure the ability of KDI polypeptides and fragments, variants derivatives and analogs thereof to elicit KDI related biological activity (either in vitro or in vivo). Other methods will be known to the skilled artisan and are within the scope of the invention.

Other Mutants

In addition to terminal deletion forms of the protein discussed above, it also will be recognized by one of ordinary skill in the art that some amino acid sequences of the KDI polypeptide can be varied without significant effect on the structure or function of the protein. If such differences in sequence are contemplated, there will be critical areas on the protein which determine activity that are considered.

Thus, the invention further includes variations of the KDI polypeptide which show substantial KDI polypeptide activity or which include regions of KDI protein such as the protein portions discussed below. Such mutants include deletions, insertions, inversions, repeats, splice variants and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the KDI polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the KDI of the present invention may include one or more amino acid substitutions, deletions or additions, either from natural mutations or human manipulation. As indicated, changes are preferably of a minor nature, such as conservative amino acid substitutions that do not significantly affect the folding or activity of the protein. Additional variant polypeptides of the present invention include expression variants that enhance secretion or increase the biological activity of the polypeptide of the present invention.

Amino acids in the KDI protein of the present invention that are essential for function can be identified by methods known in the art, such as site-directed mutagenesis or alanine-scanning mutagenesis (Cunningham and Wells, *Science* 244:1081–1085 (1989).) The latter procedure introduces single alanine mutations at every residue in the molecule. The resulting mutant molecules are then tested for biological activity such as receptor binding, in vitro proliferative activity or interferon receptor activation.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).)

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Particularly preferred substitutions for each of the KDI polypeptides described herein is the replacement of the arginine residues at position 192 with lysine (sometimes hereinafter referred to as "R192K"), and replacement of the cysteine residue at position 193 with a serine residue (sometimes hereinafter referred to as "C193S"). These substitutions can be found in a KDI polypeptide individually or they can occur in the same KDI polypeptide. The present invention provides polynucleotides encoding each of the foregoing substitution-containing KDI polypeptides.

The polypeptides of the present invention are preferably provided in an isolated form, and preferably are substantially purified. A recombinantly produced version of the KDI polypeptide can be substantially purified by the one-step method described in Smith and Johnson, *Gene* 67:31–40 (1988). Polypeptides of the invention also can be purified from natural or recombinant sources using anti-KDI antibodies of the invention in methods which are well known in the art of protein purification.

The invention further provides an isolated KDI polypeptide comprising an amino acid sequence selected from the group consisting of: (a) the amino acid sequence of the full-length KDI polypeptide having the complete amino acid sequence shown in SEQ ID NO:2; (b) the amino acid sequence of the full-length KDI polypeptide having the complete amino acid sequence shown in SEQ ID NO:2 excepting the N-terminal methionine (i.e., residues 2 to 207 of SEQ ID NO:2); the amino acid sequence of the mature KDI polypeptide shown as residues 28–207 in SEQ ID NO:2; (d) the amino acid sequence shown in SEQ ID NO:2 as residues 7 to 207; (e) the full length KDI polypeptide encoded by the human cDNA contained in clone HKAPI15; (f) the full-length KDI polypeptide encoded by the human cDNA contained in clone HKAPI15 excepting the N-terminal methionine; and (g) the mature KDI polypeptide encoded by the human cDNA contained in clone HKAPI15.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited DNA or to the polypeptide of SEQ ID NO:2, and also include portions of such polypeptides with at least 10, 20 or 30 amino acids and more preferably at least 50 amino acids.

A further embodiment of the invention relates to a peptide or polypeptide which comprises the amino acid sequence of a KDI polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a peptide or polypeptide to have an amino acid sequence which comprises the amino acid sequence of a KDI polypeptide, which contains at least one, but not more than 10, 9, 8, 7, 6, 5, 4, 3, 2 or 1 conservative amino acid substitutions.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a query amino acid sequence of a KDI polypeptide of the invention it is intended that the amino acid sequence of the subject polypeptide is identical to the query sequence except that the subject polypeptide sequence may include up to five amino acid alterations per each 100 amino acids of the query KDI amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid, or a number of amino acids up to 5% of the total amino acid residues in the query sequence may be inserted into the subject sequence. These alterations of the subject sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, (1) the amino acid sequence shown in SEQ ID NO:2; (2) the amino acid sequence encoded by deposited cDNA clone; (3) the amino acid sequence of the mature KDI protein shown in SEQ ID NO:2; or (4) the amino acid sequence of the mature KDI protein encoded by the deposited cDNA clone, each of which can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. Manual adjustment includes elimination or truncation of the native signal peptide. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are corrected manually.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting KDI protein expression as described below or as agonists and antagonists capable of enhancing or inhibiting KDI protein function. Further, such polypeptides can be used in the yeast two-hybrid system to "capture" KDI protein binding proteins which are also candidate agonists and antagonists according to the present invention. The yeast two hybrid system is described in Fields and Song, Nature 340:245–246 (1989).

Among the especially preferred polypeptide fragments of the invention are fragments characterized by structural or functional attributes of KDI. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) KDI (SEQ ID NO:2). Certain preferred regions are those set out in FIG. 3 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; Karplus-Schulz predicted flexible regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of KDI. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of KDI.

Interferon alpha possesses a wide variety of antiviral, anti-proliferative and immunomodulative biological activities. As discussed above, these multiple activities of interferon are mediated through interaction with specific cell-surface receptors. The interferon receptor receptor consists of more than one individual polypeptide component and different parts of the interferon molecule can contribute to certain interferon activities via interaction with distinct chains of the interferon receptor complex. Wang et al., J. Immunol 152:705–715; Uze et al. J. Mol. Biol 243:245–257 (1994). The structure-functional organization of the type 1 interferon molecule, the interferon receptor complex, and the role of distinct receptor chains in signal transduction has been analyzed. Danilkovitch et al. Hybridoma 16:69–75 (1997); Pontzer et al. J. Interferon Res 14: 133–141 (1994); Danilkovich et al., Immunology Letters 31:15–20 (1991). KDI polypeptide fragments, therefore, may be used to mediate antiviral, antiproliferative and immunomodulative biological activities.

Polypeptide fragments from the C-terminus of Interferon-alpha2 exhibit antiproliferative activity on normal human peripheral blood lymphocytes. Epitopes involving amino acids 124–144 of the Interferon-alpha2 molecule may be responsible for receptor binding and the manifestation of interferon antiproliferative properties. Danilkovich et al. Immunology Letters, supra. Polypeptide fragments from the carboxy-terminal region of Interferon-tau are involved in the antiviral activity by a mechanism and specificity shared by alpha Interferons. Pontzer et al. Proc. Natl. Acad. Sci. USA 87:5945–5949 (1990). Polypeptide fragments of KDI can be used, therefore, as physiological regulators of tumor cell growth, anti-proliferative activity, anti-viral activity and immunomodulatory activity.

Preferred embodiments of the present invention are directed to N-terminal deletions and C-terminal polypeptide fragments of KDI that can be used as an anti-tumor agent, such as the fragment comprising amino acid residues 168 through 182 of FIG. 1 (SEQ ID NO: 2). Additional preferred embodiments of the present invention are directed to N-terminal deletions and C-terminal polypeptide fragments of KDI that can be used as an anti-viral agent. Additional embodiments are directed to polypeptide fragments of KDI having the following residues shown in FIG. 1 (SEQ ID NO:2): 165–183, 7–207, fragments in which C193 is altered to S193, fragments in which the non-homologous loop region at residues 172–184 is deleted, fragments in which the non-homologous loop region at residues 172–183 is deleted ("Lloop"), fragments in which the non-homologous loop region at residues 173–184 is deleted and N172 is altered to D172 ("Dloop"), fragments in which the non-homologous loop region at residues 173–184 is deleted and N172 is altered to M172 ("Mloop"), fragments in which the non-homologous loop region at residues 173–184 is deleted ("Nloop"). One of the activities of the deletion mutants of the present invention is improved expression and or purification. Further embodiments discussed below are directed to antibodies developed against the carboxy-terminal fragments of the present invention that can neutralize the activities of KDI.

Additional mutations of the KDI polypeptide of the present invention include (1) alterations of C193 to S193 alone or in combination with other mutant forms of KDI; (2) alterations of N63 to R63 alone or in combination with other mutant forms of KDI; (3) alterations of R192 to K192 alone or in combination with other mutant forms of KDI; (4) alterations of C30 to S30 alone or in combination with other mutant forms of KDI; (5) alterations of C59 to S59 alone or in combination with other mutant forms of KDI; (6) alterations of C128 to S128 alone or in combination with other mutant forms of KDI; and (7) alterations of C181 to S181 alone or in combination with other mutant forms of KDI. C193 is potentially unpaired within the KDI molecule but may be involved with dimerization, along with the other cysteines. The dimerization of IFN beta has been described. See Karpusas et al., Proc. Natl. Acad. Sci. USA 94:11813–18 (1997), which is hereby incorporated by reference in its entirety.

The data representing the structural or functional attributes of KDI set forth in FIG. 3 and/or Table I, as described above, was generated using the various modules and algorithms of the DNA*STAR set on default parameters. In a preferred embodiment, the data presented in columns VIII, XII, and XIII of Table I can be used to determine regions of KDI which exhibit a high degree of potential for antigenicity. Regions of high antigenicity are determined from the data presented in columns VIII, XII, and/or XIII, by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) also was used to present the data of FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIG. 1. As set out in FIG. 3 and in Table I, such preferred regions include Gamier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII |
|---|---|---|---|---|---|---|---|---|---|---|---|---|---|---|
| Met | 1 | A | . | . | . | . | . | . | 0.57 | . | * | . | 0.65 | 1.43 |
| Ser | 2 | A | . | . | . | . | . | . | 0.96 | . | * | . | 0.65 | 1.73 |
| Thr | 3 | A | . | . | . | . | . | . | 0.74 | . | . | . | 0.95 | 2.27 |
| Lys | 4 | A | . | . | . | . | T | . | 0.24 | . | . | . | 0.85 | 2.27 |
| Pro | 5 | A | . | . | . | . | T | . | 0.63 | . | . | F | 1.00 | 1.19 |
| Asp | 6 | A | . | . | . | . | T | . | 1.28 | . | * | F | 1.00 | 1.42 |
| Met | 7 | A | . | . | . | . | T | . | 0.91 | . | . | . | 1.15 | 1.42 |
| Ile | 8 | A | . | . | B | . | . | . | 0.41 | . | . | . | 0.30 | 0.49 |
| Gln | 9 | A | . | . | B | . | . | . | 0.08 | . | . | . | 0.30 | 0.24 |
| Lys | 10 | A | . | . | B | . | . | . | −0.52 | . | . | . | −0.60 | 0.26 |
| Cys | 11 | A | . | . | B | . | . | . | −0.52 | . | * | . | −0.60 | 0.30 |
| Leu | 12 | A | . | . | B | . | . | . | −0.81 | . | . | . | −0.30 | 0.30 |
| Trp | 13 | A | . | . | B | . | . | . | −0.73 | . | . | . | −0.60 | 0.11 |
| Leu | 14 | A | . | . | B | . | . | . | −1.33 | . | . | . | −0.60 | 0.16 |
| Glu | 15 | A | . | . | B | . | . | . | −1.72 | . | * | . | −0.60 | 0.20 |
| Ile | 16 | A | . | . | B | . | . | . | −1.94 | . | . | . | −0.60 | 0.19 |
| Leu | 17 | A | . | . | B | . | . | . | −1.83 | . | * | . | −0.60 | 0.16 |
| Met | 18 | A | . | . | B | . | . | . | −2.43 | . | . | . | −0.60 | 0.08 |
| Gly | 19 | A | . | . | B | . | . | . | −2.21 | . | * | . | −0.60 | 0.08 |
| Ile | 20 | A | . | . | B | . | . | . | −2.56 | . | . | . | −0.60 | 0.10 |
| Phe | 21 | A | . | . | B | . | . | . | −1.98 | . | . | . | −0.60 | 0.10 |
| Ile | 22 | A | . | . | B | . | . | . | −1.98 | . | . | . | −0.60 | 0.14 |
| Ala | 23 | A | . | . | B | . | . | . | −1.68 | . | * | . | −0.60 | 0.17 |
| Gly | 24 | A | . | . | B | . | . | . | −2.14 | . | * | . | −0.60 | 0.26 |
| Thr | 25 | . | . | . | B | T | . | . | −1.26 | . | * | . | −0.20 | 0.30 |
| Leu | 26 | . | . | . | B | . | . | C | −1.22 | . | * | . | −0.10 | 0.50 |
| Ser | 27 | . | . | . | B | . | . | C | −0.33 | . | * | . | −0.10 | 0.27 |
| Leu | 28 | A | . | . | . | . | . | . | −0.56 | . | * | . | 0.10 | 0.30 |
| Asp | 29 | A | . | . | . | . | T | . | −1.02 | . | * | . | −0.20 | 0.30 |
| Cys | 30 | A | . | . | . | . | T | . | −0.71 | . | * | . | −0.20 | 0.19 |
| Asn | 31 | A | . | . | . | . | T | . | −0.76 | . | * | . | −0.20 | 0.36 |
| Leu | 32 | A | . | . | . | . | T | . | −0.49 | . | * | . | 0.10 | 0.16 |
| Leu | 33 | A | . | . | B | . | . | . | −0.49 | . | * | . | −0.60 | 0.41 |
| Asn | 34 | A | . | . | B | . | . | . | −0.38 | * | * | . | −0.60 | 0.21 |
| Val | 35 | A | . | . | B | . | . | . | 0.40 | * | . | . | −0.60 | 0.50 |
| His | 36 | A | . | . | B | . | . | . | −0.46 | * | . | . | 0.45 | 1.18 |
| Leu | 37 | . | . | B | B | . | . | . | 0.04 | * | * | . | 0.30 | 0.54 |
| Arg | 38 | . | . | B | B | . | . | . | 0.57 | * | * | . | 0.45 | 1.06 |
| Arg | 39 | A | . | . | B | . | . | . | 0.57 | . | * | . | −0.30 | 0.82 |
| Val | 40 | A | . | . | B | . | . | . | 1.42 | . | . | . | −0.15 | 1.72 |
| Thr | 41 | . | . | . | B | T | . | . | 0.64 | * | . | . | 0.85 | 1.41 |
| Trp | 42 | A | . | . | B | . | . | . | 1.57 | * | . | . | −0.60 | 0.59 |
| Gln | 43 | A | . | . | B | . | . | . | 1.42 | * | . | . | −0.45 | 1.56 |
| Asn | 44 | A | . | . | B | . | . | . | 0.50 | * | * | . | −0.15 | 1.48 |
| Leu | 45 | . | . | . | B | . | . | C | 1.06 | * | . | . | −0.25 | 1.16 |
| Arg | 46 | . | . | . | B | T | . | . | 1.07 | * | . | . | 0.10 | 0.90 |
| His | 47 | . | . | . | . | . | . | C | 0.76 | * | . | . | 0.10 | 0.75 |
| Leu | 48 | . | . | . | . | . | . | C | 0.46 | * | . | . | 0.10 | 0.90 |
| Ser | 49 | . | . | . | . | . | . | C | 0.46 | * | * | . | 0.70 | 0.61 |
| Ser | 50 | . | . | . | . | T | . | . | 0.97 | * | . | F | 0.45 | 0.72 |
| Met | 51 | . | . | . | . | T | T | . | 0.16 | * | . | F | 0.80 | 1.18 |
| Ser | 52 | . | . | . | . | T | T | . | −0.02 | . | . | F | 0.65 | 0.76 |
| Asn | 53 | . | . | . | . | T | T | . | −0.07 | . | * | F | 0.65 | 0.88 |
| Ser | 54 | . | . | . | . | . | T | C | 0.23 | . | * | F | 0.15 | 0.66 |
| Phe | 55 | . | . | . | . | . | . | C | −0.13 | . | . | . | 0.10 | 0.85 |
| Pro | 56 | A | . | . | . | . | . | . | −0.34 | . | . | . | −0.10 | 0.28 |
| Val | 57 | A | A | . | . | . | . | . | 0.07 | . | . | . | −0.60 | 0.17 |
| Glu | 58 | A | A | . | . | . | . | . | 0.07 | . | . | . | −0.30 | 0.39 |
| Cys | 59 | A | A | . | . | . | . | . | 0.37 | . | * | . | 0.60 | 0.44 |
| Leu | 60 | A | A | . | . | . | . | . | 0.18 | . | . | . | 0.60 | 0.96 |
| Arg | 61 | A | A | . | . | . | . | . | −0.20 | . | . | . | 0.60 | 0.39 |
| Glu | 62 | A | A | . | . | . | . | . | −0.04 | . | * | . | 0.30 | 0.73 |
| Asn | 63 | A | A | . | . | . | . | . | −0.04 | . | * | . | −0.30 | 0.77 |
| Ile | 64 | A | A | . | . | . | . | . | −0.19 | . | * | . | 0.60 | 0.68 |
| Ala | 65 | A | A | . | . | . | . | . | 0.41 | . | * | . | −0.30 | 0.32 |
| Phe | 66 | A | A | . | . | . | . | . | 0.30 | . | * | . | −0.60 | 0.31 |
| Glu | 67 | A | A | . | . | . | . | . | 0.30 | * | * | . | −0.60 | 0.77 |
| Leu | 68 | A | A | . | . | . | . | . | −0.40 | * | * | F | 0.60 | 1.31 |
| Pro | 69 | A | A | . | . | . | . | . | −0.32 | * | * | F | 0.00 | 1.31 |
| Gln | 70 | A | A | . | . | . | . | . | 0.27 | * | . | F | 0.45 | 0.63 |
| Glu | 71 | A | A | . | . | . | . | . | 0.72 | * | . | F | 0.00 | 1.31 |
| Phe | 72 | A | A | . | B | . | . | . | 0.41 | * | . | . | −0.45 | 1.33 |
| Leu | 73 | A | A | . | B | . | . | . | 1.22 | * | . | . | −0.45 | 1.11 |
| Gln | 74 | A | A | . | B | . | . | . | 1.22 | * | . | . | −0.45 | 1.11 |
| Tyr | 75 | A | A | . | B | . | . | . | 0.62 | * | . | . | −0.45 | 1.98 |
| Thr | 76 | A | . | . | B | . | . | . | 0.67 | * | . | F | −0.30 | 2.38 |
| Gln | 77 | A | A | . | B | . | . | . | 1.48 | * | . | F | 0.00 | 2.75 |

TABLE I-continued

| Res | Position | I | II | III | IV | V | VI | VII | VIII | IX | X | XI | XII | XIII |
|---|---|---|---|---|---|---|---|---|---|---|---|---|---|---|
| Pro | 78 | A | A | . | B | . | . | . | 2.29 | * | . | F | 0.60 | 3.43 |
| Met | 79 | A | A | . | . | . | . | . | 1.40 | * | . | F | 0.90 | 3.97 |
| Lys | 80 | A | A | . | . | . | . | . | 1.69 | * | . | F | 0.90 | 1.61 |
| Arg | 81 | A | A | . | . | . | . | . | 2.04 | * | . | F | 0.90 | 2.08 |
| Asp | 82 | A | A | . | . | . | . | . | 1.46 | * | . | F | 0.90 | 4.20 |
| Ile | 83 | A | A | . | . | . | . | . | 0.97 | * | . | F | 0.90 | 2.12 |
| Lys | 84 | A | A | . | . | . | . | . | 1.32 | * | . | F | 0.75 | 0.94 |
| Lys | 85 | A | A | . | . | . | . | . | 1.28 | * | . | F | 0.45 | 0.88 |
| Ala | 86 | A | A | . | . | . | . | . | 0.57 | * | . | . | 0.45 | 2.18 |
| Phe | 87 | A | A | . | . | . | . | . | 0.27 | * | * | . | 0.45 | 1.08 |
| Tyr | 88 | A | A | . | . | . | . | . | 0.34 | * | * | . | −0.30 | 0.72 |
| Glu | 89 | A | A | . | . | . | . | . | 0.30 | . | * | . | −0.60 | 0.59 |
| Met | 90 | A | A | . | . | . | . | . | −0.33 | * | * | . | −0.45 | 1.18 |
| Ser | 91 | A | A | . | . | . | . | . | −0.44 | . | . | . | −0.30 | 0.76 |
| Leu | 92 | A | A | . | . | . | . | . | 0.26 | . | . | . | −0.30 | 0.38 |
| Gln | 93 | A | A | . | . | . | . | . | −0.39 | . | . | . | −0.60 | 0.62 |
| Ala | 94 | A | A | . | . | . | . | . | −1.09 | . | . | . | −0.60 | 0.32 |
| Phe | 95 | A | A | . | . | . | . | . | −0.79 | . | . | . | −0.60 | 0.34 |
| Asn | 96 | A | A | . | . | . | . | . | −0.49 | . | . | . | −0.60 | 0.26 |
| Ile | 97 | A | A | . | . | . | . | . | 0.29 | . | . | . | −0.60 | 0.45 |
| Phe | 98 | A | A | . | . | . | . | . | −0.02 | . | . | . | −0.60 | 0.71 |
| Ser | 99 | A | . | . | . | . | T | . | −0.13 | . | * | . | −0.20 | 0.63 |
| Gln | 100 | A | . | . | . | . | T | . | 0.61 | . | * | . | −0.20 | 0.78 |
| His | 101 | . | . | . | . | . | T | C | 0.37 | . | * | . | 0.45 | 1.81 |
| Thr | 102 | . | . | . | . | . | T | C | 0.97 | . | . | . | 0.45 | 2.12 |
| Phe | 103 | . | A | . | . | T | . | . | 1.71 | * | . | . | −0.05 | 1.28 |
| Lys | 104 | A | A | . | . | . | . | . | 2.01 | . | * | . | −0.45 | 1.89 |
| Tyr | 105 | A | A | . | . | . | . | . | 2.12 | . | . | . | 0.45 | 2.27 |
| Trp | 106 | A | A | . | . | . | . | . | 2.12 | . | . | . | 0.75 | 5.12 |
| Lys | 107 | A | A | . | . | . | . | . | 1.62 | . | . | F | 0.90 | 3.49 |
| Glu | 108 | A | A | . | . | . | . | . | 2.37 | . | . | F | 0.60 | 1.83 |
| Arg | 109 | A | A | . | . | . | . | . | 2.32 | . | . | F | 0.90 | 3.49 |
| His | 110 | A | A | . | . | . | . | . | 1.68 | * | * | F | 0.90 | 3.02 |
| Leu | 111 | A | . | . | B | . | . | . | 1.97 | . | * | F | 0.90 | 1.22 |
| Lys | 112 | A | . | . | B | . | . | . | 1.03 | . | * | F | 0.60 | 1.08 |
| Gln | 113 | A | . | . | B | . | . | . | 0.69 | * | * | F | −0.15 | 0.56 |
| Ile | 114 | A | . | . | B | . | . | . | −0.23 | * | * | . | −0.30 | 0.67 |
| Gln | 115 | . | . | B | B | . | . | . | −0.20 | * | * | . | −0.30 | 0.28 |
| Ile | 116 | . | . | B | B | . | . | . | 0.61 | * | * | . | −0.30 | 0.27 |
| Gly | 117 | . | A | . | . | . | . | C | 0.57 | . | * | . | −0.10 | 0.66 |
| Leu | 118 | . | A | . | . | . | . | C | −0.02 | . | * | F | 0.05 | 0.66 |
| Asp | 119 | . | A | . | . | . | . | C | 0.87 | . | * | F | 0.05 | 0.95 |
| Gln | 120 | . | A | . | . | . | . | C | 0.62 | . | * | F | 1.10 | 1.66 |
| Gln | 121 | A | A | . | . | . | . | . | 0.70 | . | * | F | 0.60 | 3.15 |
| Ala | 122 | A | A | . | . | . | . | . | 1.04 | * | . | F | 0.60 | 1.55 |
| Glu | 123 | A | A | . | . | . | . | . | 1.86 | * | . | . | −0.15 | 1.44 |
| Tyr | 124 | A | A | . | . | . | . | . | 1.19 | * | . | . | −0.15 | 1.44 |
| Leu | 125 | A | A | . | . | . | . | . | 0.38 | * | . | . | −0.30 | 0.77 |
| Asn | 126 | A | . | . | . | . | T | . | 0.38 | * | . | . | −0.20 | 0.36 |
| Gln | 127 | A | . | . | . | . | T | . | 0.97 | * | . | . | −0.20 | 0.40 |
| Cys | 128 | A | . | . | . | . | T | . | 0.97 | . | . | . | 0.70 | 0.85 |
| Leu | 129 | A | . | . | . | . | T | . | 1.21 | . | . | . | 1.00 | 0.88 |
| Glu | 130 | A | A | . | . | . | . | . | 2.02 | . | . | F | 0.75 | 0.88 |
| Glu | 131 | A | A | . | . | . | . | . | 2.02 | . | . | F | 0.90 | 2.64 |
| Asp | 132 | A | A | . | . | . | . | . | 2.02 | . | . | F | 0.90 | 5.54 |
| Glu | 133 | A | A | . | . | . | . | . | 2.69 | . | . | F | 0.90 | 5.14 |
| Asn | 134 | A | . | . | . | . | T | . | 3.50 | . | . | F | 1.30 | 5.14 |
| Glu | 135 | A | . | . | . | . | T | . | 2.90 | . | . | F | 1.30 | 5.14 |
| Asn | 136 | A | . | . | . | . | T | . | 2.94 | . | . | F | 1.30 | 2.94 |
| Glu | 137 | A | . | . | . | . | T | . | 2.94 | . | . | F | 1.30 | 3.65 |
| Asp | 138 | A | A | . | . | . | . | . | 2.34 | . | . | F | 0.90 | 3.65 |
| Met | 139 | A | A | . | . | . | . | . | 2.39 | . | . | F | 0.90 | 2.25 |
| Lys | 140 | A | A | . | . | . | . | . | 2.39 | . | . | F | 0.90 | 2.60 |
| Glu | 141 | A | A | . | . | . | . | . | 2.39 | . | . | F | 0.90 | 2.69 |
| Met | 142 | A | A | . | . | . | . | . | 2.39 | . | . | F | 0.90 | 4.38 |
| Lys | 143 | A | A | . | . | . | . | . | 1.79 | . | . | F | 0.90 | 3.79 |
| Glu | 144 | A | A | . | . | . | . | . | 2.43 | . | . | F | 0.90 | 2.17 |
| Asn | 145 | A | A | . | . | . | . | . | 2.18 | . | . | F | 0.90 | 4.38 |
| Glu | 146 | A | A | . | . | . | . | . | 1.88 | . | . | F | 0.90 | 3.38 |
| Met | 147 | A | A | . | . | . | . | . | 2.48 | . | . | F | 0.90 | 2.62 |
| Lys | 148 | A | . | . | . | . | T | . | 1.84 | . | . | F | 1.30 | 2.82 |
| Pro | 149 | A | . | . | . | . | T | . | 1.96 | . | * | F | 1.30 | 1.64 |
| Ser | 150 | A | . | . | . | . | T | . | 1.10 | . | * | F | 1.30 | 3.26 |
| Glu | 151 | A | . | . | . | . | T | . | 0.89 | . | * | F | 1.30 | 1.21 |
| Ala | 152 | A | . | . | . | . | . | . | 1.49 | . | . | F | 1.10 | 1.21 |
| Arg | 153 | A | . | . | . | . | . | . | 0.63 | . | * | F | 1.10 | 1.56 |
| Val | 154 | A | . | . | . | . | . | . | 0.54 | . | * | F | 0.65 | 0.74 |

TABLE I-continued

| Res | Position | I | II | III | IV | V | VI | VII | VIII | IX | X | XI | XII | XIII |
|---|---|---|---|---|---|---|---|---|---|---|---|---|---|---|
| Pro | 155 | A | . | . | . | . | . | . | 0.54 | . | * | F | 0.05 | 0.99 |
| Gln | 156 | A | . | . | . | . | . | . | −0.27 | . | * | F | 0.65 | 0.67 |
| Leu | 157 | A | A | . | . | . | . | . | 0.32 | . | * | F | −0.45 | 0.75 |
| Ser | 158 | A | A | . | . | . | . | . | −0.60 | * | * | F | 0.45 | 0.84 |
| Scr | 159 | A | A | . | . | . | . | . | 0.37 | * | . | F | −0.15 | 0.40 |
| ieeu | 160 | A | A | . | . | . | . | . | 0.69 | . | . | . | 0.30 | 0.95 |
| Glu | 161 | A | A | . | . | . | . | . | 0.44 | . | * | . | 0.75 | 1.39 |
| Leu | 162 | A | . | . | B | . | . | . | 0.56 | . | * | . | 0.45 | 1.62 |
| Arg | 163 | A | . | . | B | . | . | . | 0.82 | * | * | . | 0.45 | 1.70 |
| Arg | 164 | A | . | . | B | . | . | . | 1.23 | * | * | . | 0.45 | 1.34 |
| Tyr | 165 | A | . | . | B | . | . | . | 1.16 | * | * | . | 0.45 | 3.18 |
| Phe | 166 | A | . | . | B | . | . | . | 1.16 | * | * | . | 0.45 | 1.14 |
| His | 167 | A | . | . | B | . | . | . | 1.97 | * | . | . | 0.30 | 0.97 |
| Arg | 168 | A | . | . | B | . | . | . | 1.16 | * | . | . | −0.30 | 1.00 |
| Ilc | 169 | A | . | . | B | . | . | . | 0.23 | * | * | . | −0.30 | 1.00 |
| Asp | 170 | A | A | . | B | . | . | . | 0.52 | * | * | . | −0.30 | 0.60 |
| Asn | 171 | A | A | . | . | . | . | . | 1.22 | * | . | . | 0.30 | 0.62 |
| Phe | 172 | A | A | . | . | . | . | . | 1.30 | * | * | . | 0.45 | 1.52 |
| Leu | 173 | A | A | . | . | . | . | . | 1.23 | . | * | F | 0.90 | 1.82 |
| Lys | 174 | A | A | . | . | . | . | . | 1.88 | * | . | F | 0.90 | 2.27 |
| Glu | 175 | A | A | . | . | . | . | . | 1.58 | . | . | F | 0.90 | 4.10 |
| Lys | 176 | A | A | . | . | . | . | . | 1.58 | . | . | F | 0.90 | 6.67 |
| Lys | 177 | A | A | . | . | . | . | . | 1.61 | . | . | F | 0.90 | 5.57 |
| Tyr | 178 | A | . | . | . | . | . | . | 1.83 | . | . | F | 1.30 | 1.72 |
| Ser | 179 | A | . | . | . | . | T | . | 1.50 | . | . | F | 1.15 | 0.87 |
| Asp | 180 | A | . | . | . | . | T | . | 1.50 | * | . | . | 0.10 | 0.46 |
| Cys | 181 | A | . | . | . | . | T | . | 0.57 | * | . | . | 0.10 | 0.51 |
| Ala | 182 | A | . | . | B | . | T | . | −0.33 | * | . | . | −0.30 | 0.26 |
| Trp | 183 | A | . | . | B | . | . | . | 0.02 | * | . | . | −0.30 | 0.12 |
| Glu | 184 | A | . | . | B | . | . | . | −0.53 | * | * | . | −0.30 | 0.43 |
| Ile | 185 | A | . | . | B | . | . | . | −0.53 | * | * | . | −0.30 | 0.32 |
| Val | 186 | A | . | . | B | . | . | . | −0.76 | * | * | . | 0.30 | 0.52 |
| Arg | 187 | A | . | . | B | . | . | . | −0.06 | * | * | . | 0.30 | 0.21 |
| Val | 188 | A | . | . | B | . | . | . | −0.34 | * | . | . | 0.30 | 0.59 |
| Glu | 189 | A | . | . | B | . | . | . | −0.32 | * | * | . | 0.75 | 1.55 |
| Ile | 190 | A | . | . | B | . | . | . | −0.24 | * | * | . | 0.60 | 0.42 |
| Arg | 191 | A | . | . | B | . | . | . | 0.37 | * | * | . | 0.30 | 0.47 |
| Arg | 192 | A | . | . | B | . | . | . | 0.01 | * | * | . | 0.30 | 0.43 |
| Cys | 193 | . | . | . | B | T | . | . | 0.17 | * | * | . | −0.20 | 0.95 |
| Leu | 194 | . | . | . | B | T | . | . | −0.08 | * | . | . | −0.20 | 0.42 |
| Tyr | 195 | . | . | . | B | T | . | . | 0.86 | * | . | . | −0.20 | 0.34 |
| Tyr | 196 | . | . | . | B | T | . | . | 0.04 | * | . | . | −0.05 | 1.26 |
| Phe | 197 | . | . | . | B | T | . | . | −0.38 | * | * | . | −0.05 | 1.32 |
| Tyr | 198 | . | . | . | B | T | . | . | −0.30 | . | . | . | −0.05 | 1.22 |
| Lys | 199 | A | . | . | B | . | . | . | −0.30 | . | * | . | −0.60 | 0.79 |
| Phe | 200 | A | . | . | B | . | . | . | −0.76 | * | * | . | −0.60 | 0.75 |
| Thr | 201 | A | . | . | B | . | . | . | −0.40 | * | * | . | −0.60 | 0.41 |
| Ala | 202 | A | . | . | B | . | . | . | 0.41 | * | * | . | −0.30 | 0.40 |
| Leu | 203 | A | . | . | B | . | . | . | 0.70 | * | * | . | −0.30 | 0.92 |
| Phe | 204 | A | . | . | B | . | . | . | 0.27 | * | * | . | 0.75 | 1.27 |
| Arg | 205 | A | . | . | B | . | . | . | 0.58 | * | * | . | 0.75 | 1.61 |
| Arg | 206 | A | . | . | B | . | . | . | 0.50 | . | . | . | 0.75 | 2.49 |
| Lys | 207 | A | . | . | B | . | . | . | 0.70 | . | . | . | 0.75 | 3.67 |

Among highly preferred fragments in this regard are those that comprise regions of KDI that combine several structural features, such as several of the features set out above.

Other preferred polypeptide fragments are biologically active KDI fragments. Biologically active fragments are those exhibiting activity similar, but not necessarily identical, to an activity of the KDI polypeptide. The biological activity of the fragments may include an improved desired activity, or a decreased undesirable activity. For example, it is desired to decrease interferon toxicity and side effects. Common side effects associated with patients receiving alpha interferon treatment for Hepatitis include: fatigue, muscle aches, headaches, nausea and vomiting, skin irritation at the injection site, low-trade fever, weight loss, irritability, depression and mild bone marrow suppression and hair loss. Polynucleotides encoding these polypeptide fragments are also encompassed by the invention.

However, many polynucleotide sequences, such as EST sequences, are publicly available and accessible through sequence databases. Some of these sequences are related to SEQ ID NO:1and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1156 of SEQ ID NO:1, b is an integer of 15 to 1170, where both a and b correspond to the positions of nucleotide residues shown in SEQ ID NO:1.

Epitopes and Antibodies

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC Deposit No:

203500 or encoded by a polynucleotide that hybridizes to the complement of the sequence of SEQ ID NO:1 or contained in ATCC Deposit No: 203500 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least at least 12, at least 13, at least 14, at least 15, at least 20, at least 25, at least 30, at least 40 at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting). Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Preferred epitopes of the invention include: a polypeptide comprising amino acid residues from about Ser 49 to about Ser 54 in SEQ ID NO:2; a polypeptide comprising amino acid residues from about Cys 59 to about Ala 65 in SEQ ID NO:2; a polypeptide comprising amino acid residues from about Pro 78 to about Tyr 88 in SEQ ID NO:2; a polypeptide comprising amino acid residues from about His 101 to about Gln 113 in SEQ ID NO:2; a polypeptide comprising amino acid residues Gln 120 to about Glu 123 in SEQ ID NO:2; a polypeptide comprising amino acid residues Cys 128 to about Pro 155 in SEQ ID NO:2, a polypeptide comprising amino acid residues from about Leu 160 to about Arg 168 in SEQ ID NO:2; a polypeptide comprising amino acid residues from about Asn 171 to about Asp 180 in SEQ ID NO:2; a polypeptide comprising amino acid residues from about Val 186 to about Cys 193 in SEQ ID NO:2; and a polypeptide comprising amino acid residues Phe 204 to about Lys 207 in SEQ ID NO:2. These polypeptide fragments have been determined to bear antigenic epitopes of the KDI protein by the analysis of the Jameson-Wolf antigenic index, as shown in FIG. 3, above. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^2$ M, $5 \times 10^3$ M, $10^3$ M, $5 \times 10^{-4}$ M, $10^{-4}$ M, $5 \times 10^5$ M, $10^{-5}$ M, $5 \times 10^{-6}$ M, $10^{-6}$M, $5 \times 10^{-7}$ M, $10^7$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 > 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et Cancer Res. 58(15):3209–3214 (1998); Yoon et al., J. Immunol. 160(7):3170–3179 (1998Prat et al., J. Cell. Sci. 111(Pt2):237–247 (1998); Pitard et al., J. Immunol. Methods 205(2):177–190 (1997); Liautard et al.. Cytokine 9(4):233–241 (1997); Carlson et al Biol. Chem. 272(17):11295–11301 (1997); Taryman et al., Neuron 14(4):755–762 (1995) Muller et al., Structure 6(9):1153–1167 (1998); Bartunek et al., Cytokine 8(1):14–20 (1996(which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen.

Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Pat. No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerraet al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cos mid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5) :155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N.Y. (1993); Kriegler, Gene Transfer and Expression, A Laboratory Manual, Stockton Press, N.Y. (1990); and in Chapters 12 and 13, Dracopoli et al. (eds), Current Protocols in Human Genetics, John Wiley & Sons, N.Y. (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111 In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times ^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $5 \times 10^{10-11}$ M, $10^{-11}$ M, $5 \times 10^{-12}$ M, $10^{-12}$ M, $5 \times 10^{-13}$ M, $10^{--}$M, $5 \times 10^{-14}$ M, $10^{-14}$ M, $5 \times 10^{-}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp.1 15–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox—like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($125I$, $121I$), carbon ($14C$), sulfur ($35S$), tritium ($3H$), indium ($112In$), and technetium ($99Tc$); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any KDI polypeptide can be used to generate fusion proteins. For example, the KDI polypeptide, when fused to a second protein, can be used as an antigenic tag. Antibodies raised against the KDI polypeptide can be used to indirectly detect the second protein by binding to the KDI. Moreover, because secreted proteins target cellular locations based on trafficking signals, the KDI polypeptides can be used as targeting molecules once fused to other proteins.

Examples of domains that can be fused to KDI polypeptides include not only heterologous signal sequences, but also other heterologous functional regions. The fusion does not necessarily need to be direct, but may occur through linker sequences.

In certain preferred embodiments, KDI proteins of the invention comprise fusion proteins wherein the KDI polypeptides are those described above as m-n. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Moreover, fusion proteins may also be engineered to improve characteristics of the KDI polypeptide. For instance, a region of additional amino acids, particularly charged amino acids, may be added to the N-terminus of the KDI polypeptide to improve stability and persistence during purification from the host cell or subsequent handling and storage. Also, peptide moieties may be added to the KDI polypeptide to facilitate purification. Such regions may be removed prior to final preparation of the KDI polypeptide. The addition of peptide moieties to facilitate handling of polypeptides are familiar and routine techniques in the art.

As one of skill in the art will appreciate, KDI polypeptides of the present invention and the epitope-bearing fragments thereof described above, heterologous polypeptide sequences. For example, the polypeptides of the present invention may be fused with heterologous polypeptide sequences, for example, the polypeptides of the present invention may be fused parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric KDI protein or protein fragment alone (Fountoulakis et al., *J. Biochem.* 270:3958–3964 (1995)).

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the KDI polypeptides can be fused to marker sequences, such as a peptide which facilitates purification of KDI. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the KDI polynucleotides or the polypeptides.

Vectors and Host Cells

The present invention also relates to vectors which include the isolated DNA molecules of the present invention, host cells which are genetically engineered with the recombinant vectors, and the production of KDI polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The KDI polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The KDI DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293 and Bowes melanoma cells; and plant cells.

Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, pBluescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986). It is specifically contemplated that KDI polypeptides may in fact be expressed by a host cell lacking a recombinant vector.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

The KDI protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. For example, see Lin et al., "Purification of Recombinant Human Interferon Beta expressed in *E. coli* " Methods in Enzymology 119: 183–192 (1986), which is hereby incorporated by reference in its entirety. Most preferably, high performance liquid chromatography ("HPLC") is employed for purification.

Clones containing the desired KDI constructs are grown overnight ("O/N") in liquid culture in LB media supplemented with kanamycin (25 $\mu$g/ml). The O/N culture is used to inoculate larger cultures at a dilution of approximately 1:25 to 1:250. The cells are grown to an optical density at 600 nm ("OD600") of between 0.4 and 0.6. Isopropyl-$\beta$-D-thiogalactopyranoside ("IPTG") is then added to a final concentration of 3 mM and the cells are incubated an additional 3 to 4 hours. The cells are harvested by centrifugation.

KDI expressed by this procedure is insoluble. Extraction into a soluble form was investigated using a variety of techniques, including extraction in chaotrophic agents (e.g. Urea and Guanidine) or ionic (e.g. SDS and Deoxycholic acid) or non-ionic (e.g. TX-100 and CHAPS) detergents. A consequence of using these methods is that proteins are often denatured during extraction. Denatured recombinant proteins can be renatured by dialyzing them against phosphate-buffered saline (PBS) or 50 mM Na-acetate, pH 6 buffer plus 200 mM NaCl. Alternatively, proteins have been successfully refolded while immobilized during chromatographic separations.

The following alternative method is used to purify KDI expressed in *E. coli* when it is present in the form of insoluble inclusion bodies. Unless otherwise specified, all of the following steps are conducted at 4–10° C. Upon completion of the production phase of the *E. coli* growth, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 0.15M NaCl, 0.1M sodium phosphate (PBS), pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is clarified by centrifugation at 10,000×g for 10 min to remove the majority of soluble contaminating host cell proteins. The resultant pellet is washed again using 0. 15M NaCl, 0.1M sodium phosphate (PBS), pH 7.4. The resulting washed inclusion bodies are then solubilized in a solution of 0.15M NaCl, 0.1M sodium phosphate (PBS), pH 7.4 containing 2% SDS and 10 mM DTT.

The next step is an organic extraction with 2-butanol. An equal volume of 2-butanol is added to the re-suspended inclusion body homogenate and vortexed prior to centrifugation. Phase separation is accomplished by centrifugation at 10,000 g for 15 minutes. KDI, like other interferons, partitions to the upper organic phase and is easily recovered after centrifugation. KDI is then recovered from the organic phase by acid precipitation. First, four volumes of 0.1M sodium phosphate, 0. 1% SDS are added slowly to the organic phase. Then, the mixture is slowly adjusted to pH 5.0 with glacial acetic acid and stirred for 10 minutes. KDI is recovered in the pellet fraction following centrifugation at 10,000×g for 10 min at 25° C. The pellet, which is highly enriched for KDI, is re-suspended in 0.1M sodium phosphate (PBS), pH 7.4 containing 10% SDS and 10 mM DTT and 0.5 mM EDTA.

Proteins purified by similar methods have been renatured and purified by conventional techniques, such as by quickly diluting the denaturant prior to further purification steps (e.g., ion-exchange, hydrophobic and size exclusion chromatography).

Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

In one embodiment, the yeast *Pichki pastoris* is used to express KDI protein in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzymen alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in

*Pichia pastoris*. See, Ellis, S. B., et al., Mol. Cell. Biol. 5:1111–21 (1985); Koutz, P. J, et al., *Yeast* 5:167–77 (1989); Tschopp, J. F., et al., *Nucl. Acids Res.* 15:3859–76 (1987). Thus, a heterologous coding sequence, such as, for example, a KDI polynucleotide of the present invention, under the transcriptional regulation of all or part of the AOX1 regulatory sequence may be expressed at exceptionally high levels in Pichia yeast grown in the presence of methanol.

In one example, the plasmid vector pPIC9K is used to express DNA encoding a KDI polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector is used to express and secrete a KDI protein of the invention by virtue of the strong AOX1 promoter linked to the yeast alpha factor prepro peptide signal sequence (i.e., leader) located upstream of a multiple cloning site.

Many other yeast vectors could be used in place of pPIC9K, such as, pYES2, pYD1, pTEF1/Zeo, pYES2/GS, pPICZ, PGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a KDI polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., KDI coding sequence), and/or to include genetic material (e.g., heterologous polynucleotide sequences) that is operably associated with KDI polynucleotides of the invention, and which activates, alters, and/or amplifies endogenous KDI polynucleotides. For example, techniques known in the art may be used to operably associate heterologous control regions (e.g., promoter and/or enhancer) and endogenous KDI polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., Nature, 310:105–111 (1984)). For example, a polypeptide corresponding to a fragment of a KDI polypeptide can be synthesized by use of a peptide synthesizer. Furthermore, if desired, nonclassical amino acids or chemical amino acid analogs can be introduced as a substitution or addition into the KDI polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses KDI polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The KDI polypeptides of the invention may be in monomers or multimers (i.e., dimers, trimers, tetramers and higher multimers). As discussed above, the potentially unpaired Cysteine at C193 may be involved with dimerization, along with the other Cysteines (i.e., C30, C59, C128, C181) or with Cysteines on other KDI molecules. Accordingly, the present invention relates to monomers and multimers of the KDI polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in the deposited clone (including fragments, variants, splice variants, and fusion proteins, corresponding to these as described herein). These homomers may contain KDI polypeptides having identical or different amino acid sequences. In a specific embodiment, a homomer of the invention is a multimer containing only KDI polypeptides having an identical amino acid sequence. In another specific embodiment, a homomer of the invention is a multimer containing KDI polypeptides having different amino acid sequences. In specific embodiments, the multimer of the invention is a homodimer (e.g., containing KDI polypeptides having identical or different amino acid sequences) or a homotrimer (e.g., containing KDI polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the KDI polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the KDI polypeptides of the invention. Such covalent associations may involve one or more amino acid residues contained in the polypeptide sequence (e.g., that recited in SEQ ID NO:2, or contained in the polypeptide encoded by the clone HTECD31). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a KDI fusion protein. In one example, covalent associations are between the heterologous sequence contained in a fusion protein of the invention (see, e.g., U.S. Pat. No. 5,478,925). In a specific example, the covalent associations are between the heterologous sequence contained in a KDI-Fc fusion protein of the invention (as described herein). In another specific example, covalent associations of fusion proteins of the invention are between heterologous polypeptide sequence from another protein that is capable of forming covalently associated multimers, such as for example, osetcoprotegerin (sec, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,47 8,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478, 925, which is herein incorporated by reference in its entirety).

Uses of the KDI Polynucleotides

The KDI polynucleotides identified herein can be used in numerous ways as reagents. The following description should be considered exemplary and utilizes known techniques.

There exists an ongoing need to identify new chromosome markers, since few chromosome marking reagents, based on actual sequence data (repeat polymorphisms), are presently available. Clone HKAPI15 was mapped to chromosome 9. Thus, KDI polynucleotides can be used in linkage analysis as a marker for chromosome 9. As discussed below in Example 9, PCR analysis across the panel of somatic cell hybrids reveals that KDI maps to chromosome 9 and does not contain an intron within the open reading frame. This is consistent with all known type I Interferons. Radiation Hybrid Analysis confirmed that KDI maps to chromosome 9 and appears to cluster with the other type I Interferons on the small arm of chromosome 9 (9q22).

Briefly, sequences can be mapped to chromosomes by preparing PCR primers (preferably 15–25 bp) from the sequences shown in SEQ ID NO:1. Primers can be selected using computer analysis so that primers do not span the one predicted exon in the genomic DNA. These primers are then used for PCR screening of somatic cell hybrids containing individual human chromosomes. Only those hybrids containing the human KDI gene corresponding to the SEQ ID NO:1 will yield an amplified fragment.

Genomic fragments utilizing primers designed against the KDI cDNA sequence have been PCR amplified and are subcloned. An amplicon of 1.5 kB was obtained using (ORF) suggesting the presence of an intron. This was confirmed upon sequencing. An intron appears to exist in the 3' untranslated region. The sequence of the predicted ORF matches exactly the sequence of the cDNA of SEQ ID NO:1. The deduced sequence of the HKAPI 15 cDNA fragment, therefore, corresponds with the genomic sequence.

Similarly, somatic hybrids provide a rapid method of PCR mapping the polynucleotides to particular chromosomes. Three or more clones can be assigned per day using a single thermal cycler. Moreover, sublocalization of the KDI polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the KDI polynucleotides can also be achieved using fluorescence in situ hybridization (FISH) of a metaphase chromosomal spread. This technique uses polynuclcotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the KDI polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the KDI polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the KDI polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using KDI polynucleotides. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31' mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The U.S. Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNAIDNA 15-mer lowers the melting point (T.sub.m) by 8°–20° C., vs.

4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyclocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication No. WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication No. WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a KDI polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression,CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

KDI polynucleotides are also useful in gene therapy. One goal of gene therapy is to insert a normal gene into an organism having a defective gene, in an effort to correct the genetic defect. KDI offers a means of targeting such genetic defects in a highly accurate manner. Another goal is to insert a new gene that was not present in the host genome, thereby producing a new trait in the host cell.

The KDI polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The KDI polynucleotides can be used as additional DNA markers for RFLP.

The KDI polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, KDI polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from KDI sequences. Panels of such reagents can identify tissue by species and/or by organ type. In a similar fashion, these reagents can be used to screen tissue cultures for contamination.

Since KDI is expressed mainly in keratinocytes, dentritic cells, monocytes and tonsil, KDI polynucleotides are useful as hybridization probes for differential identification of the tissue(s) or cell type(s) present in a biological sample. Similarly, polypeptides and antibodies directed to KDI polypeptides are useful to provide immunological probes for differential identification of the tissue(s) or cell type(s). In addition, for a number of diseases, disorders, and/or conditions of the above tissues or cells, particularly of the immune system, significantly higher or lower levels of KDI gene expression may be detected in certain tissues (e.g., cancerous and wounded tissues) or bodily fluids (e.g., serum, plasma, urine, synovial fluid or spinal fluid) taken from an individual having such a disorder, relative to a "standard" KDI gene expression level, i.e., the KDI expression level in healthy tissue from an individual not having the immune system disorder.

Thus, the invention provides a diagnostic method of a disorder, which involves: (a) assaying KDI gene expression level in cells or body fluid of an individual; (b) comparing the KDI gene expression level with a standard KDI gene expression level, whereby an increase or decrease in the assayed KDI gene expression level compared to the standard expression level is indicative of disorder in the immune system.

In the very least, the KDI polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of KDI Polypeptides

KDI polypeptides can be used in numerous ways. The following description should be considered exemplary and utilizes known techniques.

KDI polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99 mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99 mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of KDI polypeptide in cells or body fluid of an individual; (b) comparing the level of gene expression with a standard gene expression level, whereby an increase or decrease in the assayed KDI polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, KDI polypeptides can be used to treat, prevent, and/or diagnose disease. For example, patients can be administered KDI polypeptides in an effort to replace absent or decreased levels of the KDI polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to KDI polypeptides can also be used to treat, prevent, and/or diagnose disease. For example, administration of an antibody directed to a KDI polypeptide can bind and reduce overproduction of the polypeptide. Similarly, administration of an antibody can activate the polypeptide, such as by binding to a polypeptide bound to a membrane (receptor).

At the very least, the KDI polypeptides can be used as molecular weight markers on SDS-PAGE gels or on molecular sieve gel filtration columns using methods well known to those of skill in the art. KDI polypeptides can also be used to raise antibodies, which in turn are used to measure protein expression from a recombinant cell, as a way of assessing transformation of the host cell. Moreover, KDI polypeptides can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of the KDI polypeptide of the present invention. This method requires a polynucleotide which codes for a KDI polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a KDI polynucleotide ex vivo, with the engineered cells then being provided to a patient to be treated with the polypeptide. Such methods are well-known in the art. For example, see Belidegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the KDI polynucleotide constructs can be delivered by any method that delivers injectable materials to the cells of an animal, such as, injection into the interstitial space of tissues (heart, muscle, skin, lung, liver, and the like).

The KDI polynucleotide constructs may be delivered in a pharmaceutically acceptable liquid or aqueous carrier.

In one embodiment, the KDI polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the KDI polynucleotides can also be delivered in liposome formulations and lipofectin formulations and the like can be prepared by methods well known to those skilled in the art. Such methods are described, for example, in U.S. Pat. Nos. 5,593,972, 5,589, 466, and 5,580,859, which are herein incorporated by reference.

The KDI polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of KDI polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for KDI.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The KDI polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked KDI DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the KDI polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Feigner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{+2}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding KDI. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloprolifcrative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding KDI. Such retroviral vector particles then may be employed, to transduce eukaryotic cells, either in vitro or in vivo. The transduced eukaryotic cells will express KDI.

In certain other embodiments, cells are engineered, ex vivo or in vivo, with KDI polynucleotide contained in an adenovirus vector. Adenovirus can be manipulated such that it encodes and expresses KDI, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis. 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The KDI polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the KDI polynucleotide construct. These viral particles are then used to transduce eukaryotic cells, either ex vivo or in vivo. The transduced cells will contain the KDI polynucleotide construct integrated into its genome, and will express KDI.

Another method of gene therapy involves operably associating heterologous control regions and endogenous polynucleotide sequences (e.g. encoding KDI) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the KDI desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous KDI sequence is placed under the control of the promoter. The promoter then drives the expression of the endogenous KDI sequence.

The polynucleotides encoding KDI may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding KDI contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Administration of a KDI encoding polynucleotide may be used in gene therapy to suppress wild-type virus infection when a viral vector is employed and to down-regulate the genes that control new blood vessel formation, such as in angiosarcomas, malignant angioendothelioma and in tumors. Interferon-alpha is undergoing clinical trials. See Protze et al., Proc. Natl. Acad. Sci. USA 96:10818 and 10823; and Valentis and PolyMASC websites (www.valentis.com; www.polymase.com, respectively) describing clinial trial with its Interferon-alpha gene for treating malignant angioendothelioma.

Biological Activities of KDI

KDI polynucleotides or polypeptides, or agonists or antagonists of KDI, can be used in assays to test for one or more biological activities. If KDI polynucleotides or polypeptides, or agonists or antagonists of KDI, do exhibit activity in a particular assay, it is likely that KDI may be involved in the diseases associated with the biological activity. Therefore, KDI could be used to treat, prevent, and/or diagnose the associated disease.

Immune System-Related Disorders Treatment

It will also be appreciated by one of ordinary skill that, since the KDI protein of the invention is a member of the interferon family, when KDI is added to cells, tissues or the body of an individual, the protein will exert its physiological activities on its target cells of that individual. Therefore, it will be appreciated that conditions caused by a decrease in the standard or normal level of interferon activity in an individual, particularly disorders of the immune system, can be treated by administration of the KDI polypeptide. Thus, the invention also provides a method of treatment of an individual in need of an increased level of interferon activity comprising administering to such an individual a pharmaceutical composition comprising an amount of an isolated KDI polypeptide of the invention, effective to increase the interferon activity level in such an individual.

Further, the KDI polynucleotides, ,polypeptides, or agonists or antagonists of KDI may also be useful in treating diseases, disorders, and/or conditions of the immune system. Therefore, it will be appreciated that conditions caused by a decrease in the standard or normal level of interferon activity in an individual, particularly disorders of the immune system, can be treated by administration of KDI polynucleotides, polypeptides, or agonists or antagonists of KDI. Thus, the invention also provides a method of treatment of an individual in need of an increased level of interferon activity comprising administering to such an individual a pharmaceutical composition comprising a therapeutic amount of KDI polynucleotides, polypeptides, or agonists or antagonists of KDI, effective to increase the interferon activity level in such an individual.

The human class I IFN receptor complex which mediates the biological activity of IFN-alpha and IFN-beta also binds IFN-omega and is expected to bind KDI. Accordingly, KDI can be used clinically for anti-viral therapy, for example, in the treatment of AIDS, viral hepatitis including chronic hepatitis B, hepatitis C, papilloma viruses, viral encephalitis, and in the prophylaxis of rhinitis and respiratory infections.

KDI polynucleotides, polypeptides, or agonists or antagonists of KDI are also useful in the treatment of numerous cancers (e.g., hairy cell leukemia, acute myeloid leukemia, osteosarcoma, basal cell carcinoma, glioma, renal cell carcinoma, multiple myeloma, melanoma, and Hodgkin's disease).

KDI is believed to stimulate natural killer cell activity. Accordingly, KDI polynucleotides, polypeptides, or agonists or antagonists of KDI may be used to treat parasitic and bacterial infection for example, for treating Cryptosporidium parvuminfection and multidrug-resistant pulmonary tuberculosis.

KDI is also believed to be useful as an immunotherapeutic agent, more specifically as an immunosuppressive agent. For example, KDI is believed to inhibit proliferation of lymphocytes stimulated with mitogens or allogeneic cells, myeloid progenitor cells and other bone marrow cells. Accordingly, KDI polynucleotides, polypeptides, or agonists or antagonists of KDI are useful as a protective agent when administered prior to chemotherapy and in addition can be used to treat hyperproliferation of lymphocytes, myeloid progenitors and bone marrow stem cells, e.g., in the treatment of chronic myelogenous leukemia. KDI polynucleotides, polypeptides, or agonists or antagonists of KDI can also be used in the prevention of graft vs. host rejection, or to curtail the progresion of autoimmune diseases, such as arthritis, multiple sclerosis, systemic lupus or diabetes. KDI polynucleotides, polypeptides, or agonists or antagonists of KDI are also useful in the treatment of allergies in mammals, e.g., by inhibiting the humoral response.

KDI polynucleotides, polypeptides, or agonists or antagonists of KDI may be used as an adjuvant or coadjuvant to enhance or simulate the immune response in cases of prophylactic or therapeutic vaccination.

Further, there is provided a method of treating infection in a patient comprising administering an effective amount of KDI polynucleotides, polypeptides, or agonists or antagonists of KDI to a patient in need of anti-infective therapy. In a preferred embodiment the infection is of viral, bacterial, or parasitic etiology. In a particularly preferred embodiment, the infection is a viral infection.

Further, there is provided a method of treating cancer in a patient comprising administering an effective amount of KDI polynucleotides, polypeptides, or agonists or antagonists of KDI to a patient in need of anti-cancer therapy.

Further, there is provided a method of immunotherapy in a patient comprising administering an effective amount of KDI polynucleotides, polypeptides, or agonists or antagonists of KDI to a patient in need of immunotherapy.

KDI polynucleotides or polypeptides, or agonists or antagonists of KDI, may be useful in treating diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, KDI polynucleotides or polypeptides, or agonists or antagonists of KDI, can be used as a marker or detector of a particular immune system disease or disorder.

KDI polynucleotides or polypeptides, or agonists or antagonists of KDI, may be useful in treating, preventing, and/or diagnosing diseases, disorders, and/or conditions of hematopoietic cells. KDI polynucleotides or polypeptides, or agonists or antagonists of KDI, could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, KDI polynucleotides or polypeptides, or agonists or antagonists of KDI, can also be used to modulate hemostatic (the stopping of bleeding) or thrombolytic activity (clot formation). For example, by increasing hemostatic or thrombolytic activity, KDI polynucleotides or polypeptides, or agonists or antagonists of KDI, could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, KDI polynucleotides or polypeptides, or agonists or antagonists of KDI, that can decrease hemostatic or thrombolytic activity could be used to inhibit or dissolve clotting. These molecules could be important in the treatment or prevention of heart attacks (infarction), strokes, or scarring.

KDI polynucleotides or polypeptides, or agonists or antagonists of KDI, may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of KDI polynucleotides or polypeptides, or agonists or antagonists of KDI, that can inhibit an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by KDI include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by KDI polynucleotides or polypeptides, or agonists or antagonists of KDI. Moreover, these molecules can be used to treat anaphylaxis, hypersensitivity to an antigenic molecule, or blood group incompatibility.

KDI polynucleotides or polypeptides, or agonists or antagonists of KDI, may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of KDI polynucleotides or polypeptides, or agonists or antagonists of KDI, that inhibits an immune response, particularly the proliferation, differentiation, or chemotaxis of T-cells, may be an effective therapy in preventing organ rejection or GVHD.

Similarly, KDI polynucleotides or polypeptides, or agonists or antagonists of KDI, may also be used to modulate inflammation. For example, KDI polynucleotides or polypeptides, or agonists or antagonists of KDI, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

KDI polynucleotides or polypeptides, or agonists or antagonists of KDI, can be used to treat, prevent, and/or diagnose hyperproliferative diseases, disorders, and/or conditions, including neoplasms. KDI polynucleotides or polypeptides, or agonists or antagonists of KDI, may inhibit the proliferation of the disorder through direct or indirect interactions. Alternatively, KDI polynucleotides or polypeptides, or agonists or antagonists of KDI, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by KDI polynucleotides or polypeptides, or agonists or antagonists of KDI, include, but are not limited to neoplasms located in the:colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by KDI polynucleotides or polypeptides, or agonists or antagonists of KDI. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative diseases, disorders, and/or conditions by inserting into an abnormally proliferating cell a polynucleotide of the present invention, wherein said polynucleotide represses said expression.

Another embodiment of the present invention provides a method of treating cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferrably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. USA. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}M$, $10^{-6}M$, $5\times10^{-7}M$, $10^{-7}M$, $5\times10^{-8}M$, $10^{-8}M$, $5\times10^{-9}M$, $10^{-9}M$, $5\times10^{10}M$, $10^{10}M$, $5\times10^{-11}M$, $10^{-11}M$, $5\times10^{-12}M$, $10^{-12}M$, $5\times10^{-13}M$, $10^{-13}M$, $5\times10^{-14}M$, $10^{-14}M$, $5\times10^{15}M$, and $10^{-15}M$.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph IB, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et.al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses.50(5):423–33 (1998) Biol Interact. Apr 24;111–112:23–34 (1998), J Mol Med.76(6):402–12 (1998), Int J Tissue React;20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

KDI polynucleotides or polypeptides, or agonists or antagonists of KDI, encoding KDI may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangitis obliterans, hypersensitivity vasculitis, Schoenlein-Henoch purpura, allergic cutaneous vasculitis, and Wegener's granulomatosis.

KDI polynucleotides or polypeptides, or agonists or antagonists of KDI, are especially effective for the treatment of critical limb ischemia and coronary disease. KDI polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. KDI polypeptides may be administered as part of a Therapeutic, described in more detail below. Methods of delivering KDI polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630–634 (1991); Folkman et al., *N. Engl. J. Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat, prevent, and/or diagnose superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, comeal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a mucoadhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions. Moreover, diseases, disorders, and/or conditions and/or states, which can be treated with be treated with the the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by KDI polynucleotides or polypeptides, as well as antagonists or agonists of KDI, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, KDI polynucleotides, polypeptides, and/or antagonists of the invention are used to inhibit growth, progression, and/or metasis of cancers, in particular those listed above.

Additional diseases or conditions associated with increased cell survival that could be treated, prevented, and/or diagnosed by KDI polynucleotides or polypeptides, or agonists or antagonists of KDI, include, but are not limited to, progression, and/or metastases of malignancies and related diseases, disorders, and/or conditions such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by KDI polynucleotides or polypeptides, as well as agonists or antagonists of KDI, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immnune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing KDI polynucleotides or polypeptides, as well as agonists or antagonists of KDI, for therapeutic purposes, for example, to stimulate epithelial cell proliferation and basal keratinocytes for the purpose of wound healing, and to stimulate hair follicle production and healing of dermal wounds. KDI polynucleotides or polypeptides, as well as agonists or antagonists of KDI, may be clinically useful in stimulating wound healing including surgical wounds, excisional wounds, deep wounds involving damage of the dermis and epidermis, eye tissue wounds, dental tissue wounds, oral cavity wounds, diabetic, ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associed with systemic treatment with steroids, radiation therapy and antineoplastic drugs and antimetabolites. KDI polynucleotides or polypeptides, as well as agonists or antagonists of KDI, could be used to promote dermal reestablishment subsequent to dermal loss KDI polynucleotides or polypeptides, as well as agonists or antagonists of KDI, could be used to increase the adherence of skin grafts to a wound bed and to stimulate re-epithelialization from the wound bed. The following are types of grafts that KDI polynucleotides or polypeptides, agonists or antagonists of KDI, could be used to increase adherence to a wound bed: autografts, artificial skin, allografts, autodenric graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. KDI polynucleotides or polypeptides, as well as agonists or antagonists of KDI, can be used to promote skin strength and to improve the appearance of aged skin.

It is believed that KDI polynucleotides or polypeptides, as well as agonists or antagonists of KDI, will also produce changes in hepatocyte proliferation, and epithelial cell proliferation in the lung, breast, pancreas, stomach, small intesting, and large intestine. KDI polynucleotides or polypeptides, as well as agonists or antagonists of KDI, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. KDI polynucleotides or polypeptides, agonists or antagonists of KDI, may promote proliferation of endothelial cells, keratinocytes, and basal keratinocytes.

KDI polynucleotides or polypeptides, as well as agonists or antagonists of KDI, could also be used to reduce the side effects of gut toxicity that result from radiation, chemotherapy treatments or viral infections. KDI polynucleotides or polypeptides, as well as agonists or antagonists of KDI, may have a cytoprotective effect on the small intestine mucosa. KDI polynucleotides or polypeptides, as well as agonists or antagonists of KDI, may also stimulate healing of mucositis (mouth ulcers) that result from chemotherapy and viral infections.

KDI polynucleotides or polypeptides, as well as agonists or antagonists of KDI, could further be used in full regeneration of skin in full and partial thickness skin defects, including burns, (i.e., repopulation of hair follicles, sweat glands, and sebaceous glands), treatment of other skin defects such as psoriasis. KDI polynucleotides or polypeptides, as well as agonists or antagonists of KDI, could be used to treat, prevent, and/or diagnose epidermolysis bullosa, a defect in adherence of the epidermis to the underlying dermis which results in frequent, open and painful blisters by accelerating reepithelialization of these lesions. KDI polynucleotides or polypeptides, as well as agonists or antagonists of KDI, could also be used to treat, prevent, and/or diagnose gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, KDI polynucleotides or polypeptides, as well as agonists or antagonists of KDI, could be used to promote the resurfacing of the mucosal surface to aid more rapid healing and to prevent progression of inflammatory bowel disease. Treatment with KDI polynucleotides or polypeptides, agonists or antagonists of KDI, is expected to have a significant effect on the production of mucus throughout the gastrointestinal tract and could be used to protect the intestinal mucosa from injurious substances that are ingested or following surgery. KDI polynucleotides or polypeptides, as well as agonists or antagonists of KDI, could be used to treat, prevent, and/or diagnose diseases associate with the under expression of KDI.

Moreover, KDI polynucleotides or polypeptides, as well as agonists or antagonists of KDI, could be used to prevent and heal damage to the lungs due to various pathological states. A growth factor such as KDI polynucleotides or polypeptides, as well as agonists or antagonists of KDI, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using KDI polynucleotides or polypeptides, agonists or antagonists of KDI. Also, KDI polynucleotides or polypeptides, as well as agonists or antagonists of KDI, could be used to stimulate the proliferation of and differentiation of type II pneumocytes, which may help treat, prevent, and/or diagnose disease such as hyaline membrane diseases, such as infant respiratory distress syndrome and bronchopulmonary displasia, in premature infants.

KDI polynucleotides or polypeptides, as well as agonists or antagonists of KDI, could stimulate the proliferation and differentiation of hepatocytes and, thus, could be used to alleviate or treat, prevent, and/or diagnose liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, KDI polynucleotides or polypeptides, as well as agonists or antagonists of KDI, could be used treat, prevent, and/or diagnose the onset of diabetes mellitus. In patients with newly diagnosed Types I and II diabetes, where some islet cell function remains, KDI polynucleotides or polypeptides, as well as agonists or antagonists of KDI, could be used to maintain the islet function so as to alleviate, delay or prevent permanent manifestation of the disease. Also, KDI polynucleotides or polypeptides, as well as agonists or antagonists of KDI, could be used as an auxiliary in islet cell transplantation to improve or promote islet cell function.

Neurological Diseases

Nervous system diseases, disorders, and/or conditions, which can be treated with the KDI compositions of the invention (e.g., KDI polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the KDI polypeptides, polynucleotides, or agonists or antagonists of the invention are used to protect neural cells from the damaging effects of cerebral hypoxia. According to this embodiment, the KDI compositions of the invention are used to treat, prevent, and/or diagnose neural cell injury associated with cerebral hypoxia. In one aspect of this embodiment, the KDI polypeptides, polynucleotides, or agonists or antagonists of the invention are used to treat, prevent, and/or diagnose neural cell injury associated with cerebral ischemia. In another aspect of this embodiment, the KDI polypeptides, polynucleotides, or agonists or antagonists of the invention are used to treat, prevent, and/or diagnose neural cell injury associated with cerebral infarction. In another aspect of this embodiment, the KDI polypeptides, polynucleotides, or agonists or antagonists of the invention are used to treat, prevent, and/or diagnose neural cell injury associated with a stroke. In a further aspect of this embodiment, the KDI polypeptides, polynucleotides, or agonists or antagonists of the invention are used to treat, prevent, and/or diagnose neural cell injury associated with a heart attack.

The compositions of the invention which are useful for treating, preventing, and/or diagnosing a nervous system disorder may be selected by testing for biological activity in promoting the survival or differentiation of neurons. For example, and not by way of limitation, KDI compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Additional examples of neurologic diseases which can be treated, prevented, and/or diagnosed with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia. Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis, cerebrovascular diseases, disorders, and/or conditions (such as carotid artery diseases which include carotid artery thrombosis, carotid stenosis and Moyamoya Disease, cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache, migraine, dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, posttraumatic epilepsy, status epilepticus such as Epilepsia Partialis Continua, Hallervorden-Spatz Syndrome, hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, cerebral malaria, meningitis such as arachnoiditis, aseptic meningtitis such as viral meningtitis which includes lymphocytic choriomeningitis. Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uveomeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie) cerebral toxoplasmosis, central nervous system neoplasms such as brain neoplasms that include cerebellear neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta, hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative diseases, disorders, and/or conditions such as hearing diseases, disorders, and/or conditions that includes deafness, partial hearing loss, loudness recruitment and tinnitus, language diseases, disorders, and/or conditions such as aphasia which include agraphia, anomia, broca aphasia, and Wernicke Aphasia, Dyslexia such as Acquired Dyslexia, language development diseases, disorders, and/or conditions, speech diseases, disorders, and/or conditions such as aphasia which includes anomia, broca aphasia and Wernicke Aphasia, articulation diseases, disorders, and/or conditions, communicative diseases, disorders, and/or conditions such as speech disorders which include dysarthria, echolalia, mutism and stuttering, voice diseases, disorders, and/or conditions such as phonia and hoarseness, decerebrate state, delirium, fasciculation, hallucinations, meningism, movement diseases, disorders, and/or conditions such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste diseases, disorders, and/or conditions such as ageusia and dysgeusia, vision diseases, disorders, and/or conditions such as amblyopia, blindness, color vision defects, diplopia, hemianopsia, scotoma and subnormal vision, sleep diseases, disorders, and/or conditions such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia,Melkersson-Rosenthal Syndrome, ocular motility diseases, disorders, and/or conditions which includes amblyopia, nystagmus, oculomotor nerve paralysis, ophthalmoplegia such as Duane's Syndrome, Horner's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, Diabetic neuropathies such as diabetic foot, nerve compression syndromes such as carpal tunnel syndrome, tarsal tunnel syndrome, thoracic outlet syndrome such as cervical rib syndrome, ulnar nerve compression syndrome, neuralgia such as causalgia, cervicobrachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Infectious Disease

KDI polynucleotides or polypeptides, or agonists or antagonists of KDI, can be used to treat; prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, KDI polynucleotides or polypeptides, or agonists or antagonists of KDI, may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), Cryptococcus neoformans, Aspergillosis, Bacillaceae (e.g., Anthrax, Clostridium), Bacteroidaceae, Blastomycosis, Bordetella, Borrelia (e.g., *Borrelia burgdorferi*), Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi*, and *Salmonella paratyphi*), Serratia, Yersinia), Erysipelothrix, Helicobacter, Legionellosis, Leptospirosis, Listeria, Mycoplasmatales, *Mycobacterium leprae*, *Vibrio cholerae*, Neisseriaceae (e.g., Acinetobacter, Gonorrhea, Menigococcal), *Meisseria meningitidis*, Pasteurellacea Infections (e.g., Actinobacillus, Heamophilus (e.g., *Heamophilus influenza* type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

KDI polynucleotides or polypeptides, or agonists or antagonists of KDI, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, KDI polynucleotides or polypeptides, or agonists or antagonists of KDI, may increase regeneration of tissues difficult to heal. For example, increased tendon/ligament regeneration would quicken recovery time after damage. KDI polynucleotides or polypeptides, or agonists or antagonists of KDI, of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using KDI polynucleotides or polypeptides, or agonists or antagonists of KDI, to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the KDI polynucleotides or polypeptides, or agonists or antagonists of KDI.

Chemotaxis

KDI polynucleotides or polypeptides, or agonists or antagonists of KDI, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

KDI polynucleotides or polypeptides, or agonists or antagonists of KDI, may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that KDI polynucleotides or polypeptides, or agonists or antagonists of KDI, may inhibit chemotactic activity. These molecules could also be used to treat, prevent, and/or diagnose diseases, disorders, and/or conditions. Thus, KDI polynucleotides or polypeptides, or agonists or antagonists of KDI, could be used as an inhibitor of chemotaxis.

Binding Activity

KDI polypeptides may be used to screen for molecules that bind to KDI or for molecules to which KDI binds. The binding of KDI and the molecule may activate (agonist), increase, inhibit (antagonist), or decrease activity of the KDI or the molecule bound. Examples of such molecules include antibodies, oligonucleotides, proteins (e.g., receptors),or small molecules.

Preferably, the molecule is closely related to the natural ligand of KDI, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which KDI binds, or at least, a fragment of the receptor capable of being bound by KDI (e.g., active site). In either case, the molecule can be rationally designed using known techniques.

Preferably, the screening for these molecules involves producing appropriate cells which express KDI, either as a secreted protein or on the cell membrane. Preferred cells include cells from mammals, yeast, Drosophila, or E. coli. Cells expressing KDI(or cell membrane containing the expressed polypeptide) are then preferably contacted with a test compound potentially containing the molecule to observe binding, stimulation, or inhibition of activity of either KDI or the molecule.

The assay may simply test binding of a candidate compound to KDI, wherein binding is detected by a label, or in an assay involving competition with a labeled competitor. Further, the assay may test whether the candidate compound results in a signal generated by binding to KDI.

Alternatively, the assay can be carried out using cell-free preparations, polypeptide/molecule affixed to a solid support, chemical libraries, or natural product is mixtures. The assay may also simply comprise the steps of mixing a candidate compound with a solution containing KDI, measuring KDI/molecule activity or binding, and comparing the KDI/molecule activity or binding to a standard.

Preferably, an ELISA assay can measure KDI level or activity in a sample (e.g., biological sample) using a monoclonal or polyclonal antibody. The antibody can measure KDI level or activity by either binding, directly or indirectly, to KDI or by competing with KDI for a substrate.

Additionally, the receptor to which KDI binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors. Moreover, the techniques of gene-shuffling, motif-shuffling, exon-shuffling, and/or codon-shuffling (collectively referred to as "DNA shuffling") may be employed to modulate the activities of KDI thereby effectively generating agonists and antagonists of KDI. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al., *J. Mol. Biol.* 287:265–76 (1999); and Lorenzo, M. M. and Blasco, R. *Biotechniques* 24(2):308–13 (1998) (each of these patents and publications are hereby incorporated by reference). In one embodiment, alteration of KDI polynucleotides and corresponding polypeptides may be achieved by DNA shuffling. DNA shuffling involves the assembly of two or more DNA segments into a desired KDI molecule by homologous, or site-specific, recombination. In another embodiment, KDI polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of KDI may be recombined with one or more components, motifs, sections, parts, domains, fragments, etc. of one or more heterologous molecules. In preferred embodiments, the heterologous molecules are Transforming Growth Factor family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active KDI fragments. Biologically active fragments are those exhibiting activity similar, but not necessarily identical, to an activity of the KDI polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be. measured. Alternatively, the response of a known second messenger system following interaction of a compound to be screened and the KDI receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to KDI comprising the steps of: (a) incubating a candidate binding compound with KDI; and (b) determining if binding has occurred. Moreover, the invention includes a method of identifying agonists/antagonists comprising the steps of: (a) incubating a candidate compound with KDI, (b) assaying a biological activity, and (b) determining if a biological activity of KDI has been altered.

Also, one could identify molecules bind KDI experimentally by using the beta-pleated sheet regions disclosed in FIG. 3 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1. Additional embodiments of the invention are directed to polynucleotides encoding KDI polypeptides which comprise, or alternatively consist of, any combination or all of the beta pleated sheet regions disclosed in FIG. 3/Table 1. Additional preferred embodiments of the invention are directed to polypeptides which comprise, or alternatively consist of, the KDI amino acid sequence of each of the beta pleated sheet regions disclosed in FIG. 3/Table 1. Additional embodiments of the invention are directed to KDI polypeptides which comprise, or alternatively consist of, any combination or all of the beta pleated sheet regions disclosed in FIG. 3/Table 1.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Agonists and Antagonists—Assays and Molecules

The invention also provides a method of screening compounds to identify those which enhance or block the action of KDI on cells, such as its interaction with KDI-binding molecules such as receptor molecules. An agonist is a compound which increases the natural biological functions of KDI or which functions in a manner similar to KDI, while antagonists decrease or eliminate such functions.

In another aspect of this embodiment the invention provides a method for identifying a receptor protein or other ligand-binding protein which binds specifically to a KDI polypeptide. For example, a cellular compartment, such as a membrane or a preparation thereof, may be prepared from a cell that expresses a molecule that binds KDI. The preparation is incubated with labeled KDI. KDI and complexes of KDI bound to the receptor or other binding protein are isolated and characterized according to routine methods known in the art. Alternatively, the KDI polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds KDI, such as a molecule of a signaling or regulatory pathway modulated by KDI. The preparation is incubated with labeled KDI in the absence or the presence of a candidate molecule which may be a KDI agonist or antagonist. The ability of the candidate molecule to bind the binding molecule is reflected in decreased binding of the labeled ligand. Molecules which bind gratuitously, i.e., without inducing the effects of KDI on binding the KDI binding molecule, are most likely to be good antagonists. Molecules that bind well and elicit effects that are the same as or closely related to KDI are agonists.

KDI-like effects of potential agonists and antagonists may by measured, for instance, by determining activity of a second messenger system following interaction of the candidate molecule with a cell or appropriate cell preparation, and comparing the effect with that of KDI or molecules that elicit the same effects as KDI. Second messenger systems that may be useful in this regard include but are not limited to AMP guanylate cyclase, ion channel or phosphoinositide hydrolysis second messenger systems.

Another example of an assay for KDI antagonists is a competitive assay that combines KDI and a potential antagonist with membrane-bound KDI receptor molecules or recombinant KDI receptor molecules under appropriate conditions for a competitive inhibition assay. KDI can be labeled, such as by radioactivity, such that the number of KDI molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing KDI-induced activities, thereby preventing the action of KDI by excluding KDI from binding.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression." CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of KDI. The antisense RNA oligonucleotide hybridizes to the mRNA in vivo and blocks translation of the mRNA molecule into KDI polypeptide. The oligonucleotides described above can also be delivered to cells such that the antisense RNA or DNA may be expressed in vivo to inhibit production of KDI protein.

In specific embodiments, antagonists according to the present invention are nucleic acids corresponding to the sequences contained in SEQ ID NO: 1, or the complementary strand thereof, and/or to nucleotide sequences contained in the deposited clone 203500. In one embodiment, antisense sequence is generated internally, by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2×ligation buffer (20 mM TRIS HCl pH 7.5, 10 mM MgCl2, 10 mM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby lo preventing transcription and the production of the receptor. The antisense RNA oligonucleotide hybridizes to the mRNA in vivo and blocks translation of the mRNA molecule into receptor polypeptide.

In one embodiment, the KDI antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the KDI antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding KDI, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a KDI gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded KDI antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a KDI RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of KDI shown in FIGS. 1A–B could be used in an antisense approach to inhibit translation of endogenous KDI mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of KDI mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage. agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the KDI coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy KDI mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of KDI (FIGS. 1A–B). Preferably, the ribozyme is engineered so that the cleavage recognition site is located near the 5' end of the KDI mRNA, i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express KDI in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous KDI messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

The agonists and antagonists may be employed in a composition with a pharmaceutically acceptable carrier, e.g., as described above.

The antagonists may be employed for instance to inhibit interferon activity, for example, following chemotherapy to stimulate proliferation of bone marrow and haematopoietic progenitor cells. Any of the above antagonists may be employed in a composition with a pharmaceutically acceptable carrier, e.g., as hereinafter described.

Formulations

The KDI polypeptide composition will be formulated and dosed in a fashion consistent with good medical practice, taking into account the clinical condition of the individual patient (especially the side effects of treatment with KDI polypeptide alone), the site of delivery of the KDI polypeptide composition, the method of administration, the scheduling of administration, and other factors known to practitioners. The "effective amount" of KDI polypeptide for purposes herein is thus determined by such considerations.

As a general proposition, the total pharmaceutically effective amount of KDI polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the KDI polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the KDI of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The KDI polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release KDI polypeptide compositions also include liposomally entrapped KDI polypeptide. Liposomes containing KDI polypeptide are prepared by methods known per se: U.S. Pat. No. DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544.545; and EP 102,324. Ordinarily, the liposomes are of the small (about 200–800 Angstroms) unilamellar type in which the lipid content is greater than about 30 mol. percent cholesterol, the selected proportion being adjusted for the optimal KDI polypeptide therapy.

A liposomally entrapped KDI polypeptide of the present invention can be produced for clinically effective formulations. Modified interferons, such as PEG-Intron (Schering-Plough INTRON®) are clinically effective and can be used in therapies with other agents, such as Robavirin.

The KDI polypeptide may be administered in combination with other known anti-viral, immunomodulatory and anti-proliferative therapies, such as IL-2, alpha interferon, Ribavirin and temozolomide.

For parenteral administration, in one embodiment, the KDI polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the KDI polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The KDI polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of KDI polypeptide salts.

KDI polypeptide to be used for therapeutic administration must be sterile. Sterility is readily accomplished by filtration through sterile filtration membranes (e.g., 0.2 micron membranes). Therapeutic KDI polypeptide compositions generally are placed into a container having a sterile access port, for example, an intravenous solution bag or vial having a stopper pierceable by a hypodermic injection needle.

KDI polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous KDI polypeptide solution, and the resulting mixture is lyophilized. The infusion solution is prepared by reconstituting the lyophilized KDI polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating, preventing, and/or diagnosing wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal diseases, disorders, and/or conditions or neuro-degenerative conditions such as Alzheimer's disease, Parkinson's disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

A polypeptide, polynucleotide, agonist, or antagonist of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

EXAMPLES

Example 1

Cloning and Expression of KDI in *E. coli*

The novel pHE4 series of bacterial expression vectors, in particular, the pHE4a vector is used for bacterial expression in this example. (QIAGEN, Inc., 9259 Eton Avenue, Chatsworth, Calif., 91311). pHE4-5/KDI vector plasmid DNA contains the KDI coding polynucleotide shown in FIG. 1 inserted between unique restriction enzyme sites NdeI and Asp718. The construct was deposited with the ATCC on Feb. 25, 1998 and given Accession No. 209645, as a convenience to those of skill in the art.

The pHE4a bacterial expression vector includes a neomycin phosphotransferase gene for selection, an E. coli origin of replication, a T5 phage promoter sequence, two lac operator sequences, a Shine-Delgarno sequence, and the lactose operon repressor gene (lacIq). In one version of the pHE4 vector, pHE[HIS], these elements are arranged such that an inserted DNA fragment encoding a polypeptide expresses that polypeptide with the six His residues (i.e., a "6xHis tag") covalently linked to the amino terminus of that polypeptide.

The DNA sequence encoding the mature KDI protein is amplified using PCR oligonucleotide primers which anneal to the amino terminal sequences of the desired portion of the KDI protein and to sequences in the deposited construct 3' to the cDNA coding sequence. Additional nucleotides containing restriction sites to facilitate cloning in the pHE4a vector are added to-the 5' and 3' primer sequences, respectively.

For cloning the KDI protein from amino acid residue L28 into the non HIS-tagged vector, the 5' primer has the sequence 5' GGCCGCATATGCTGGACTGTAACTTACTG3' (SEQ ID NO:16) containing the underlined NdeI restriction site, or the NotI site for cloning into the HIS tag version of pHE4, pHE[HIS]. As discussed above, one of ordinary skill in the art would appreciatet hat the point in the protein coding sequence where the 5' primer begins may be varied to amplify a DNA segment encoding any desired portion of the complete KDI protein. Also appreciated by the skilled artisan is the genetic code and species-specific codon preferences, which are well known in the art. Thus, it would be routine for one skilled in the art to generate the degenerate variants described above, for instance, to optimize codon expression for a particular host (e.g., change codons in the human mRNA to those preferred by a bacterial host such as E. coli). The 3' primer has the sequence of either 5' GGCCGCGGTACCTTATTTCCTCCTGAATAGAGC3' (SEQ ID NO:17) or 5' CGCGCGGTACCTTATTATTTCCTCCTGAATAGA3' (SEQ ID NO: 24) containing the underlined Asp718 restriction site.

The amplified KDI DNA fragment is digested with NdeI and Asp718 and it and the linearized plasmid are then ligated together. Insertion of the KDI DNA into the restricted pHE4a vector places the KDI protein coding region downstream from the IPTG-inducible promoter and in pHE[HIS], in-frame with an initiating AUG and the six histidine codons.

The ligation mixture is transformed into competent E. coli cells using standard procedures such as those described by Sambrook and colleagues (Molecular Cloning: a Laboratory Manual, 2nd Ed.; Cold Spring Harbor Laboratory Press, Cold Spring Harbor, N.Y. (1989)). E. coli is used in carrying out the illustrative example described herein. Many strains are suitable for expressing KDI protein. Transformants are identified by their ability to grow on LB plates in the presence of kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with kanamycin (25 µg/ml). The O/N culture is used to inoculate a large culture, at a dilution ranging from 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCL, pH 8 to solubilize KDI. The cell debris is removed by centrifugation, and the supernatant containing the KDI polypeptide is loaded onto a nickel-nitrilo-tri-acetic acid ("Ni-NTA") affinity resin column (QIAGEN, Inc., supra). Proteins with a 6xHis tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the KDI is eluted with 6 M guanidine-HC, pH 5.

Denatured recombinant proteins are often renatured by dialyzing them against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify KDI expressed in E coli when it is present in the form of insoluble inclusion bodies. Unless otherwise specified, all of the following steps are conducted at 4–10° C.

Upon completion of the production phase of the E. coli fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells were then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation Tris, 50 mM EDTA, pH 7.4. The resulting washed inclusion bodies are solubilized in a 1.5 M guanidine hydrochloride (GuHCl) solution for 2–4 hours. After 7000xg centrifugation for 15 min., the pellet is discarded and the KDI polypeptide-containing supernatant is incubated at 4° C. overnight to allow further GuHCL extraction.

Following high speed centrifugation (30,000xg) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded KDI polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perspetive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the KDI polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the KDI polypeptide (determined, for instance, by 16% SDS-PAGE) are then pooled.

The resultant KDI polypeptide exhibits greater than 95% purity after the above refolding and purification steps. The KDI polypeptide is the major band observed on a Commassie blue stained 16% SDS-PAGE gel when 5 µg of purified protein is loaded. When a fermenter is used for the production of KDI in *E. coli*, Elongation Factur T Unstable (EFTU) may be induced and co-purified with KDI. This protein is not present in non-transformed and uninduced cells. The purified protein is also tested for endotoxin/LPS contamination, and typically the LPS content is less than 0.1 ng/ml according to LAL assays.

The following alternative method may be used to purify KDI expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the KDI polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded KDI polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the KDI polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the KDI polypeptide (determined, for instance, by 16% SDS-PAGE) are then pooled.

The resultant KDI polypeptide exhibits greater than 95% purity after the above refolding and purification steps. No major contaminant bands are observed on a Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Multiple KDI expression constructs have been generated to facilitate the production of KDI polypeptides of several sizes and in several systems. Codon optimized constructs are designated as being synthetic (sKDI). The *E. coli* based constructs are as follows: (1) pQE9:KDI.S27-K207 (expresses amino acids 27–207 of SEQ ID NO:2); (2) pHE4:KDI.S27-K207 (expresses amino acids 27–207 of SEQ ID NO:2); (3) pHE4:KDI.A23-K207 (expresses amino acids 23–207 of SEQ ID NO:2); (4) pHE4.KDI.G24-K207 (expresses amino acids 24–207 of SEQ ID NO:2); (5) pHE4.KDI.C30-K207 (expresses amino acids 30–207 of SEQ ID NO:2); (6) pHE.sKDI.L28-K207 (expresses amino acids 28–207 of SEQ ID NO:2); (7) pHE.pelB.sKDI.L28-K207 (expresses amino acids 28–207 of SEQ ID NO:2, using a heterologous leader sequence from the gene for pectate lyase (peIB) that expresses proteins in the periplasm of *E. coli*); (8) pHE:KDI.sL28-K207.C193S (expresses amino acids 28–193 of SEQ ID NO:2 in which C193 is altered to S193); (9) pHE:KDI.C30-A182 (expresses amino acids 30–182 of SEQ ID NO:2); (10) pHE:KDI.C30-R192 (expresses amino acids 30–192 of SEQ ID NO:2); (11) pHE:sKDI.C30-K207 (expresses amino acids 30–207 of SEQ ID NO:2); (12) pHE:KDI.C30-R192K (expresses amino acids 30–192 of SEQ ID NO:2 in which R192 is altered to K192);,(13) pHE:KDI.C30-C193S (expresses amino acids 30–193 of SEQ ID NO:2); (14) pHE:KDI.C30-K199 (expresses amino acids 30–199 of SEQ ID NO:2); (15) pHE:KDI.C30-K199 (R192K) (expresses amino acids 30–199 of SEQ ID NO:2 in which R192 is altered to K192); (16) pHE:KDI.C30-K207 (R192K) (expresses amino acids 30–207 of SEQ ID NO:2 in which R192 is altered to K192); (17) pHE:KDI.C30-I190 (expresses amino acids C30–190 of SEQ ID NO:2); (18) pHE[HIS]:KDI.A23-K207 (expresses amino acids 23–207 of SEQ ID NO:2 with a HIS tag); (19) pHE[HIS]:KDI.S27-K207 (expresses amino acids 27–207 of SEQ ID NO:2 with a HIS tag); (20) pHE[HIS]:KDI.G24-K207 (expresses amino acids 24–207 of SEQ ID NO:2 with a HIS tag); (21) pHE[HIS ]:KDI.C30-K207

(expresses amino acids 30–207 of SEQ ID NO:2 with a HIS tag); (22) pHE[HIS]:sKDI.C30-K207 (expresses amino acids 30–207 of SEQ ID NO:2 with a HIS tag); (23) pHE[pelB.HIS]sKDI.C30-K207 (expresses amino acids 30–207 of SEQ ID NO:2 with a HIS tag using the pelB leader); (24) pHE[HIS]:sKDI.L28-K207 (expresses amino acids 28–207 of SEQ ID NO:2 with a HIS tag); (25) pHE[pelB]:KDI.C30-R192K (expresses amino acids 30–192 of SEQ ID NO:2 in which R192 is altered to K192 using the pelB leader); (26) pQE13:KDI.S27-K207 (expresses amino acids 27–207 of SEQ ID NO:2).

The pelB sequence, which directs expression of proteins in *E.coli* to the periplasmic space, is be fused to KDI. To generate a pelB-KDI fusion to direct expression of KDI to the periplasm, the mature form of synthetic KDI is PCR amplified using a 5' primer containing the pelB leader sequence directly fused to the mature form of KDI (L28-K207) and subcloned into pHE4. The pelB sequence which directs expression of proteins in *E.coli* to the periplasmic space is he fused to KDI to determine if KDI can be tolerated/expressed in *E.coli* in that cell compartment. Localization of the protein to the periplasmic space may result in a more soluble KDI protein.

A pelB-KDI fusion may be generated to direct expression of KDI to the periplasm, easing purification of soluble KDI. The mature form of synthetic KDI is PCR amplified using a 5' primer containing the pelB leader sequence directly fused to the mature form of KDI (L28-K207) and subcloned into pHE4. The pelB sequence added is: KYLLPTAAAGLLL-LAAQPAMA. To aid in expression the synthetic KDI (*E.coli* optimized) open reading frame is used as this directs expression in *E.coli*.

Example 2
Cloning and Expression of KDI protein in a Baculovirus Expression System In this illustrative example, the plasmid shuttle vector pA2 GP is used to insert the cloned DNA encoding KDI, into a baculovirus to express the KDI protein, using a baculovirus leader and standard methods as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the Autographa californica nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (19989).

The cDNA sequence encoding the full length KDI protein containing the AUG initiation codon and the naturally associated leader sequence shown in SEQ ID NO:2, is amplified using PCR oligonucleotide primers corresponding to the 5' and 3' sequences of the gene. The 5' primer has the sequence 5' GGCCGGGATCCGCCATCATGAGCAC-CAAACCTGATATG 3' (SEQ ID NO:18) containing the underlined BamHI restriction enzyme site. The cDNA sequence encoding the mature KDI protein, lacking the AUG initiation codon and the naturally associated leader sequence shown in SEQ ID NO:2, is amplified using PCR oligonucleotide primers corresponding to the 5' and 3' sequences of the gene. The 5' primer has the sequence 5' GGCCTGGGATCCCCTGGACTGTAACTTACTG 3' (SEQ ID NO:23) containing the underlined BamHI restriction enzyme site. The 3' primer has the sequence 5' GGC-CGCGGTACCTTATTTCCTCCTGAATAGAGC 3' (SEQ ID NO:19) containing the underlined Asp718 restriction site.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel.

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

Fragment and the dephosphorylated plasmid are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human KDI gene by digesting DNA from individual colonies using BamHI and Asp718 and then analyzing the digestion product by gel electrophoresis. The sequence of the cloned fragment is confirmed by DNA sequencing. This plasmid is designated herein pA2gp.KDI.L28-K207.

Five µg of the plasmid pA2GPKDI is co-transfected with 1.0 µg of a commercially available linearized baculovirus DNA ("BaculoGold™ M baculovirus DNA", Pharmingen, San Diego, Calif.), using the lipofection method described by Felgner et al., Proc. Natl. Acad. Sci. USA 84: 7413–7417 (1987). One µg of BaculoGold™ virus DNA and 5 µg of the plasmid pA2GPKDI are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-KDI.

To verify the expression of the KDI gene Sf9 cells are grown in Grace's medium supplemented with 10% heat-inactivated FBS. The cells are infected with the recombinant baculovirus V-KDI at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the of the KDI protein. Other baculovirus expression constructs were constructed as follows: (1) pA2:KDI (which expresses residues 1–207 of SEQ ID NO:2); (2) pA2.KDI.M7-K207 (which expresses residues 7–207 of SEQ ID NO:2); (3) pA2gp.KDI.L28-K207 (which expresses residues 28–207 of SEQ ID NO:2); (4) pA2gp.KDI.C30-K207 (which expresses residues 30–207 of SEQ ID NO:2); and (5) pA2.KDI.M1-R192 (which expresses residues 1 to 192 of SEQ ID NO:2).

Example 3
Cloning and Expression of KDI in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Fechnology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Vectors also may employ polynucleotides encoding a KDI polypeptide having a heterologous signal fused to a KDI polypeptide at residues 28 or 30. An example of such a heterologous leader sequence is the signal sequence of myeloid progenitor inhibitory factor-1 (MPIF-1) disclosed in U.S. Pat. No. 6,001,606. Particularly preferred vectors employ polynucleotides encoding the MPIF-1 signal sequence upstream of the polynucleotide sequence encoding a KDI polypeptide that starts at either amino acid residue 28 or 30 in FIG. 1 (SEQ ID NO:2).

Cloning and Expression in CHO Cells

The vector pC4-Sig is used for the expression of KDI polypeptide. Plasmid pC4-Sig is a derivative of the plasmid pSV2-dhfr (ATCC Accession No. 37146). It contains coding region for the secretory leader sequence from chemokine beta-8 (see U.S. Ser. No. 95/09508) upstream from the multiple cloning site and is designed to be inframe with inserted heterologous DNA. The plasmid contains the mouse DHFR gene under control of the SV40 early promoter. Chinese hamster ovary—or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochein. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the KDI polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BainHi and Asp718 and then dephosphorylated using calf intestinal phosphates by procedures known in the art. The vector is then isolated from a 1% agarose gel.

The DNA sequence encoding the KDI polypeptide is amplified using PCR oligonucleotide primers corresponding to the 5' and 3' sequences of the desired portion of the gene. The 5' primer containing the underlined BamnHI site, a Kozak sequence, and an AUG start codon, has the following sequence: 5' GGCCGGGATCCGCCATCATGAGCAC-CAAACCTGATATG 3' (SEQ ID NO: 18). The 3' primer, containing the underlined Asp718 restriction site has the following sequence: 5' GGCCGCGGTACCTTATTTCCTC-CTGAATAGAGC 3' (SEQ ID NO: 19).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five $\mu$g of the expression plasmid pC4 is cotransfected with 0.5 $\mu$g of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones are obtained which grow at a concentration of 100 –200 $\mu$M. Expression of the desired gene product is analyzed, for instance, by SDS-PAGE and Western blot or by reversed phase HPLC analysis.

Other mammalian expression vectors constructed are as follows: (1) pC4:KDI (which expresses residues 1–207 of SEQ ID NO:2); (2) pC4sp:KDI.C30-K207 (which expresses a heterologous signal peptide (the chemokine beta-8 (MPIF-1) signal peptide) followed by amino acid residues 30–207 of KDI; and (3) pC4sp:KDI.L28-K207 (which expresses a heterologous signal peptide (the MPIF-1 signal peptide) followed by amino acid residues 28–207 of KDI Example 4

Tissue Distribution of KDI Polypeptides

Tissue distribution of mRNA expression of KDI and how it compares to other type I Interferons, is determined by Northern blot analysis and real time PCR. With regards to Northern Analysis, a panel of multiple tissue Northern Blots available commercially is screened using protocols for Northern blot analysis, described by, among others, Sambrook et al. For example, a KDI probe produced by the method described in Example 1 is labeled with $P^{32}$ using the rediprime m DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at –70 degree C. overnight, and the films developed according to standard procedures.

Expression of KDI in keratinocytes is examined by Northern analysis. Also, the expression of KDI in cells treated with dsRNA (a mimic of viral challenge) can be examined as the expression of known interferons is known to be induced by viruses.

To determine the levels of KDI, Taqman analysis can be utilized. As the expression of other type I IFNs has been shown to be enhanced upon induction by viral challenge, to the expression level of the KDI mRNA in response to dsRNA (a mimic of viral challenge) can be determined. Thus, keratinocytes are treated with varying concentrations of dIdC (dsRNA) for varying time periods (e.g., 1, 5, 15 hours). Total RNA is extracted and subjected to Northern Analysis with a KDI probe.

When Northern analysis is not sensitive enough to detect KDI expression, Taqman analysis is employed. Utilizing a KDI specific probe, RNA from keratinocytes, PBMC (+/−activation) and keratinocytes (+/−dIdC) is subjected to quantitative Taqman analysis. KDI expression is apparent in keratinocytes, dendritic cells, monocytes stimulated with interferon gamma, tonsil and resting PBMC. KDI mRNA expression may be down regulated in activated PBMC. KDI may also be regulated by viral challenge, as evidenced by enhanced expression upon exposure to dIdC.

Example 5

TAQMAN

Quantitative PCR (QPCR). Total RNA from cells in culture are extracted by Trizol separation as recommended by the supplier (LifeTechnologies). (Total RNA is treated with DNase I (Life Technologies) to remove any contaminating genomic DNA before reverse transcription.) Total RNA (50 ng) is used in a one-step, 50 ul, RT-QPCR, consisting of Taqman Buffer A (Perkin-Elmer; 50 mM KCl/10 mM Tris, pH 8.3), 5.5 mM $MgCl_2$, 240 $\mu$M each dNTP, 0.4 units RNase inhibitor(Promega), 8% glycerol, 0.012% Tween-20, 0.05% gelatin, 0.3uM primers, 0.1 uM probe, 0.025 units Amplitaq Gold (Perkin-Elmer) and 2.5 units Superscript II reverse transcriptase (Life Technologies). As a control for genomic contamination, parallel reactions are setup without reverse transcriptase. The relative abundance of (unknown) and 18S RNAs are assessed by using the Applied Biosystems Prism 7700

Sequence Detection System (Livak, K. J., Flood, S. J., Marmaro, J., Giusti, W. & Deetz, K. (1995) PCR Methods Appl. 4, 357–362). Reactions are carried out at 48° C. for 30 min, 95° C. for 10 min, followed by 40 cycles of 95° C. for 15 s, 60° C. for 1 min. Reactions are performed in triplicate.

Primers (f & r) and FRET probes sets are designed using Primer Express Software (Perkin-Elmer). Probes are labeled at the 5'-end with the reporter dye 6-FAM and on the 3'-end with the quencher dye TAMRA (Biosource International, Camarillo, Calif. or Perkin-Elmer).

To determine which signaling pathways KDI activates preliminary, Taqman analyses are performed. In the first analysis, fibroblasts, keratinocytes and Daudi cells are treated with supernatants from a CHO line stably transformed with pC4 or with pC4:KDI.L28-Flag and with exogenous IFN alpha. Cells are collected at 0.1, 6 and 18 hrs and RNA isolated. RNA from the fibroblasts and keratinocytes treated after 6 hrs are tested for expression levels of STAT-1, IRF-1, Cylin D3, EGR, ERK-3, and c-myc.

Because KDI prepared in *E.coli* is active in the ISRE and anti-viral assays, *E. coli* prepared KDI.L28, IFNb and the

| Gene | | | |
|---|---|---|---|
| KDI | probe | CAACCTATGAAGAGGGACATCAAGAAGGCC | (SEQ ID NO: 34) |
| | f-primer | GCCCCAAGAGTTTCTGCAATAC | (SEQ ID NO: 35) |
| | r-primer | GGCCTGTAGGGACATTTCATAGA | (SEQ ID NO: 36) |
| 18s | probe | TGCTGGCACCAGACTTGCCCTC | (SEQ ID NO: 37) |
| | f-primer | CGGCTACCACATCCAAGGAA | (SEQ 1D NO: 38) |
| | r-primer | GCTGGAATTACCGCGGCT | (SEQ ID NO: 39) |
| STAT 1 | probe | AAGCTTCTTGGTCCTAACGCCAGCCC | (SEQ ID NO: 40) |
| | f-primer | TCAATGTGGACCAGCTGAACAT | (SEQ ID NO: 41) |
| | r-primer | CGTCCACGGAATGAGACCAT | (SEQ ID NO: 42) |
| MXA5 | probe | CCACGGTTCCCTGCCTGGCAG | (SEQ ID NO: 43) |
| | f-primer | GGATCTGCTGGAGGAAGGAAA | (SEQ ID NO: 44) |
| | r-primer | GATGAGCTCGCTGGTAAGTTTT | (SEQ ID NO: 45) |
| 2-5A E | probe | TGGCAGCTATAAACCTAACCCCCAAATCTATGTC | (SEQ ID NO: 46) |
| | f-primer | CTTTGATGCCCTGGGTCAGT | (SEQ ID NO: 47) |
| | r-primer | TCGGTGCACTCCTCGATGA | (SEQ ID NO: 48) |
| IFNa2 | probe | TGGCCCTCCTGGTGCTCAGCTG | (SEQ ID NO: 49) |
| | f-primer | TGGCCTTGACCTTTGCTTTACT | (SEQ ID NO: 50) |
| | r-primer | AGCCCACAGAGCAGCTTGA | (SEQ ID NO: 51) |
| IFNb | probe | CAGTTCCAGAAGGAGGACGCCGC | (SEQ ID NO: 52) |
| | f-primer | GACATCCCTGAGGAGATTAAGCA | (SEQ ID NO: 53) |
| | r-primer | CTGGAGCATCTCATAGATGGTCAA | (SEQ ID NO: 54) |

Taqman analysis may be used to assess the time-course and magnitude of induction of genes potentially involved in KDI-mediated action. For example, cells can be treated for various time periods with KDI as well as other interferons, such as IFN alpha and IFN beta. Extracted RNA is then subjected to Taqman analysis using primer/probe sets designed to measure the relative induction of specific IFN-stimulated genes (e.g., MxA, 2–5A synthetase, STAT1), other immunoregulatory genes, anti-viral genes and anti-proliferative genes. The time-course and magnitude of induction from KDI, indicates the various mechanism(s) by which KDI elicits its function, particularly as compared to other type I interferons. Probes that are useful in assessing the mechanism by which KDI mediates an anti-viral response include, for example, MxA, dsRNA-Dependent Protein Kinase, and 2–5 A synthetases. Probes that are useful in assessing KDI's ability to mediate anti-proliferative responses include, for example, c-myc, cyclin D3, and cdc25a. Probes that are useful in assessing KDI's immuno-modulatory effect include, for example, IgG switching. The involvement of KDI in angiogenesis and apoptosis may also be assessed with specific probes in this manner. These methods and probes are further described in Stark, G. R. et al. (1998) Ann. Rev. Biochem 67:227–64, which is hereby incorporated by reference in its entirety. DNA array screening may be used to assess which genes are upregulated or downregulated in response to KDI treatment, as compared to IFN alpha or beta treatment. See Example 64, below.

Example 6
Taqman Signaling Analysis

The expression of KDI in cells treated with dsRNA (a mimic of viral challenge) is examined as the expression of known interferons is induced by viruses. To determine more sensitively the levels of KDI, Taqman analysis is utilized.

host cell extract alone are tested on Daudi cells which are reportedly highly sensitive to IFNs. Cells are harvested after 6 hrs and RNA prepared. Controls include RNA analyzed for the level of two mRNAs: MxA and OASE. Both of these genes are known to be upregulated by type I IFNs. Both Mx-A and OASE are upregulated by IFNa, but also by KDI.L28 and IFNb generated from *E.coli* but not by W3110 cell extract alone. Activation for both genes is similar for both IFNb and for KDI.L28. The signals transduced by KDI compared to the known IFNs can be assessed.

*E.coli* prepared KDI can activate the anti-viral MxA and 2–5' OAS mRNAs in Daudi cells as measured by Taqman. Fresh Daudi cells are retreated with preparations of IFNb, KDI.L28; His-KDI.C30; W3110 cell extract; Buffer alone, cells harvested after 6 and 24 hrs, and RNA prepared. Taqman analysis can show that the levels of MxA and 2–5 OAS increase in response to IFNb. KDI samples can also show an increase compared to buffer and cell extract treated cells for both the MxA and 2–5 OAS treated cells. NK cells and dendritic cells can be treated with KDI proteins. RNA is isolated and an initial screen of the levels of MxA, 2–5 OAS and STAT1 are determined. In addition keratinocytes and fibroblasts are assayed.

Example 7
KDI mRNA Levels in Resting and Activated Keratinocytes

KDI mRNA expression in keratinocytes can be demonstrated by taqman analysis. The level of KDI mRNA in keratinocytes can be tested after treatment with polydIdc (a mimic of dsRNA), IFN gamma or TNF alpha. RNA is isolated from resting keratinocytes. Keratinocytes are treated with polydldC for either 5 or 15 hrs, with IFN gamma for 5 hrs, or with TNF alpha for 15 hrs. RNA is isolated for keratinocytes using RNAzol and the RNA is subjected to either Taqman analysis or Northern analysis and probed for the KDI mRNA.

Taqman Analysis may be used to show that polyIC treatment increased the level of KDI keratinocytes in a time dependent manner. IFN gamma may enhance the KDI expression level. TNF alpha may have a minimal effect. Both Northern analysis and the pattern of expression determined by Taqman analysis can show that the transcript size of KDI is approximately 1 kb.

KDI mRNA expression may be upregulated by challenge with dsRNA like other interferons. Its expression may also upregulated by IFN gamma but poorly by TNF alpha. KDI may be encoded by a single 1 kb mRNA species.

Example 8
Chromosomal Mapping of KDI

An oligonucleotide primer set is designed according to the sequence at the 5' end of SEQ ID NO: 1. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

PCR analysis across the panel of somatic cell hybrids revealed that KDI maps to chromosome 9 and does not contain an intron within the open reading frame. This is consistent with all known type I Interferons. A panel of somatic cell hybrids available from Quantum Biotechnology is screened with KDI gene specific primers to determine the chromosome to which KDI maps. Radiation Hybrid Analysis confirmed that KDI maps to chromosome 9 and appears to cluster with the other type I Interferons on the small arm of chromosome 9 (9q22).

Example 9
Construction of N-Terminal and/or C-Terminal Deletion Mutants

The following general approach may be used to clone a N-terminal or C-terminal deletion KDI deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired KDI polynucleotide fragment. An initiation and stop codon are added to the 5' and 3' primers respectively, if necessary, to express the KDI polypeptide fragment encoded by the polynucleotide fragment. Preferred KDI polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the KDI polynucleotide fragment in a desired vector may also be added to the 5' and 3' primer sequences. The KDI polynucleotide fragment is amplified from genomic DNA or from the deposited cDNA clone using the appropriate PCR oligonucleotide primers and conditions discussed herein or known in the art. The KDI polypeptide fragments encoded by the KDI polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the KDI polypeptide fragment L-28 to K-207 is amplified and cloned as follows: A 5' primer is generated comprising a restriction enzyme site followed by an initiation codon in frame with the polynucleotide sequence encoding the N-terminal portion of the polypeptide fragment beginning with L-28. A complementary 3' primer is generated comprising a restriction enzyme site followed by a stop codon in frame with the polynucleotide sequence encoding C-terminal portion of the KDI polypeptide fragment ending with K-207.

The amplified polynucleotide fragment and the expression vector are digested with restriction enzymes which recognize the sites in the primers. The digested polynucleotides are then ligated together. The KDI polynucleotide fragment is inserted into the restricted expression vector, preferably in a manner which places the KDI polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 10
Protein Fusions of KDI

KDI polypeptides are preferably fused to other proteins. These fusion proteins can be used for a variety of applications. For example, fusion of KDI polypeptides to His-tag, HA-tag, protein A, IgG domains, and maltose binding protein facilitates purification. (See Example 1; see also EP A 394,827; Traunecker, et al., Nature 331:84–86 (1988).) Similarly, fusion to IgG-1, IgG-3, and albumin increases the halflife time in vivo. Nuclear localization signals fused to KDI polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 1.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and KDI polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

GGGATCCGGAGCCCAAATCTTCTGA-
CAAAACTCACACATGCCCACCGTGC

CCAGCACCTGAATTCGAGGGTGCACCGT-
CAGTCTTCCTCTTCCCCCCAAAACCCA

AGGACACCCTCATGATCTCCCGGACTC-
CTGAGGTCACATGCGTGGTGGTGGACG

TAAGCCACGAAGACCCTGAGGTCAAGT-
TCAACTGGTACGTGGACGGCGTGGAG

GTGCATAATGCCAAGACAAAGCCGCGG-
GAGGAGCAGTACAACAGCACGTACCG

TGTGGTCAGCGTCCTCACCGTCCTGCAC-
CAGGACTGGCTGAATGGCAAGGAGTA

CAAGTGCAAGGTCTCCAACAAAGCCCTC-
CCAACCCCCATCGAGAAAACCATCYC

CAAAGCCAAAGGGCAGCCCCGAGAACCA-
CAGGTGTACACCCTGCCCCCATCCC

GGGATGAGCTGACCAAGAACCAGGT-
CAGCCTGACCTGCCTGGTCAAAGGCTTCT

ATCCAAGCGACATCGCCGTGGAGTGG-
GAGAGCAATGGGCAGCCGGAGAACAAC

TACAAGACCACGCCTCCCGTGCTG-
GACTCCGACGGCTCCTTCTTCCTCTACAGCA

AGCTCACCGTGGACAAGAGCAGGTG-
GCAGCAGGGGAACGTCTTCTCATGCTCC

GTGATGCATGAGGCTCTGCACAACCAC-
TACACGCAGAAGAGCCTCTCCCTGTCT

CCGGGTAAATGAGTGCGACGGCCGCGACT-
CTAGAGGAT (SEQ ID NO:4)

Example 11
Production of an Antibody
a) Hybridoma Technology

The antibodies of the present invention can be prepared by a variety of methods. (See, Current Protocols, Chapter 2.) As one example of such methods, cells expressing KDI are administered to an animal to induce the production of sera containing polyclonal antibodies. In a preferred method, a preparation of KDI protein is prepared and purified to render it substantially free of natural contaminants. Such a preparation is then introduced into an animal in order to produce polyclonal antisera of greater specific activity.

Monoclonal antibodies specific for KDI protein are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with KDI polypeptide or, more preferably, with a secreted KDI polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the KDI polypeptide.

Alternatively, additional antibodies capable of binding to KDI polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the KDI protein-specific antibody can be blocked by KDI. Such antibodies comprise anti-idiotypic antibodies to the KDI protein-specific antibody and are used to immunize an animal to induce formation of further KDI protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against KDI from a Library of scFvs

Naturally occurring V-genes isolated from human PBLs are constructed into a library of antibody fragments which contain reactivities against KDI to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µ/ml ampicillin and 50 µg/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUCI9 derivative supplying the wild type gene III protein during phage morphogenesis. The culture is incubated for I hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 7° C. Phage particles are purified and concentrated from the culture medium by two PEG-recipitations (Sambrook et al., 1990), resuspended in 2 ml PBS and passed through a 0.45 μm filter (Minisart NML; Sartorius) to give a final concentration of approximately 1013 ransducing units/ml (ampicillin-resistant clones).

Panning of the Library

Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCL, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacteria library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 12
Production of KDI Protein for High-Throughput Screening Assays

The following protocol produces a supernatant containing KDI polypeptide to be tested. This supernatant can then be used in the Screening Assays described in Examples 14–21.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5ml Optimem 1 (31985070 Gibco/BRL)/96-well plate. With a small volume multi-channel pipetter, aliquot approximately 2 ug of an expression vector containing a polynucleotide insert, produced by the methods described in Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a12-channel pipetter with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1%BSA in DMEM with 1×penstrep, or HGS CHO-5 media (116.6 mg/L of CaCl2 (anhyd); 0.00130 mg/L CuSO4— 5H2O; 0.050 mg/L of Fe(NO3)3—9H2O; 0.417 mg/L of FeSO4—7H2O; 311.80 mg/L of Kcl; 28.64 mg/L of MgCl2; 48.84 mg/L of MgSO4; 6995.50 mg/L of NaCl; 2400.0 mg/L of NaHCO3; 62.50 mg/L of NaH2PO4—H2O; 71.02 mg/L of Na2HPO4; 0.4320 mg/L of ZnSO4—7H2O; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-H2O; 6.65 mg/ml of L-Aspartic Acid; 29.56 mg/ml of L-Cystine-2HCL-H2O; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-H2O; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H2O;and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin B12; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1×penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 14–21.

It is specifically understood that when activity is obtained in any of the assays described below using a supernatant, the activity originates from either the KDI polypeptide directly (e.g., as a secreted protein) or by KDI inducing expression of other proteins, which are then secreted into the supernatant. Thus, the invention further provides a method of identifying the protein in the supernatant characterized by an activity in a particular assay.

Example 13
Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." (See, e.g., Ihle, J. N. (1996) Cell 84: 331–334.) There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

These STATs can form homo- and heterodimers and bind to very similar yet different symmetrical dyad sequences. Id. When cells are stimulated with IFN-a or IFN-b, a DNA-binding complex is formed that consists of STAT1, STAT2, and another protein known as p48. This complex binds to the enhancer element, IFN-stimulated response element (ISRE).

The expression of a group of human genes, the interferon-stimulated genes (ISGs), is induced by IFN-a and IFN-b, the type I interferons. Lamer, A. C., et al. (1984) Proc. Natl. Acad. Sci. USA 81: 6733–6737; Lamer, A. C., et al. (1986) J. Biol. Chem. 261: 453–459. One of these genes, termed ISG54, because it encodes a 54-kDa protein, contains an ISRE in its promoter. For example, see Levy, D. E., et al. (1998) Genes Devel. 2: 383–393. This ISRE is responsible for the inducible expression of the ISG54. Id. To create the pISRE-SEAP plasmid, five direct repeats of this ISRE are placed upstream of the basic promoter element (TATA box) and the secreted alkaline phosphatase (SEAP) gene of the pSEAP2-Promoter plasmid backbone (Clontech).

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

|  | JAKs | | | | | |
| --- | --- | --- | --- | --- | --- | --- |
| Ligand | tyk2 | Jak1 | Jak2 | Jak3 | STATS | GAS (elements) or ISRE |
| IFN family | | | | | | |
| IFN-a/B | + | + | − | − | 1,2,3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotrohic) | + | + | + | ? | 1,3 | GAS (IRF1 > Lys6 > IFP) |
| Il-11 (Pleiotrohic) | ? | + | ? | ? | 1,3 | |
| OnM (Pleiotrohic) | ? | + | + | ? | 1,3 | |
| LIF (Pleiotrohic) | ? | + | + | ? | 1,3 | |
| CNTF (Pleiotrohic) | −/+ | + | + | ? | 1,3 | |
| G-CSF (Pleiotrohic) | ? | + | ? | ? | 1,3 | |

-continued

| Ligand | JAKs | | | | STATS | GAS (elements) or ISRE |
|---|---|---|---|---|---|---|
| | tyk2 | Jak1 | Jak2 | Jak3 | | |
| IL-12 (Pleiotrohic) g-C family | + | – | + | + | 1,3 | |
| IL-2 (lymphocytes) | – | + | – | + | 1,3,5 | GAS |
| IL-4 (lymph/myeloid) | – | + | – | + | 6 | GAS (IRF1 = IFP >> Ly6)(IgH) |
| IL-7 (lymphocytes) | – | + | – | + | 5 | GAS |
| IL-9 (lymphocytes) | – | + | – | + | 5 | GAS |
| IL-13 (lymphocyte) | – | + | ? | ? | 6 | GAS |
| IL-15 gp140 family | ? | + | ? | + | 5 | GAS |
| IL-3 (myeloid) | – | – | + | – | 5 | GAS (IRF1 > IFP >> Ly6) |
| IL-5 (myeloid) | – | – | + | – | 5 | GAS |
| GM-CSF (myeloid) Growth hormone family | – | – | + | – | 5 | GAS |
| GH | ? | – | + | – | 5 | |
| PRL | ? | +/– | + | – | 1,3,5 | |
| EPO Receptor Tyrosine Kinases | ? | – | + | – | 5 | GAS (B-CAS > IRF1 = IFP >> Ly6) |
| EGF | ? | + | + | – | 1,3 | GAS (IRF1) |
| PDGF | ? | + | + | – | 1,3 | |
| CSF-1 | ? | + | + | – | 1,3 | GAS (not IRF1) |

The ISRE/SEAP reporter construct contains the secreted alkaline phosphatase (SEAP) reporter gene driven by the basic promoter element (TATA box) joined to direct repeats of cis-acting ISRE. Xu, L., et al. (1997) Strategies 10: 79–80. When a plasmid expressing a gene of interest is cotransfected into mammalian cells with a cis-reporter plasmid, increased SEAP expression indicates either direct or indirect activation of the transcription factors that bind to the ISRE. The ISRE/SEAP reporter plasmid can be used to evaluate the effect of uncharacterized genes, growth factors, drug candidates, or the effects of extracellular stimuli on these transcriptional elements.

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

5':GCGCCTCGAGATTTCCCCGAAATCTA-
GATTTCCCCGAAATGATTTCCCCGAAA TGATTTC-
CCCGAAATATCTGCCATCTCAATTAG:3' (SEQ ID NO:25)

The downstream primer is complementary to the SV40 promoter and is flanked with a Hind III site: 5':GCG-GCAAGCTTTTTGCAAAGCCTAGGC:3' (SEQ ID NO:26) PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

5':CTCGAGATTTCCCCGAAATCTAGATTTC-
CCCGAAATGATTTCCCCGAAATGATT
TCCCCGAAATATCTGCCATCTCAATT-
AGTCAGCAACCATAGTCCCGCCCCTAACT CCGCCCATC-
CCGCCCCTAACTCCGCCCAGTTCCGC-
CCATTCTCCGCCCCATGGCT
GACTAATTTTTTTTATTTATGCAGAGGC-
CGAGGCCGCCTCGGCCTCTGAGCTATT CCAGAAG-
TAGTGAGGAGGCTTTTTTGGAGGCCTAG-
GCTTTTGCAAAAAGCTT:3' (SEQ ID NO:27).

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be used instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 14–15.

Other constructs can be made using the above description and replacing GAS with a different promoter sequence. For example, construction of reporter molecules containing NFK-B and EGR promoter sequences are described in Examples 16 and 17. However, many other promoters can be substituted using the protocols described in these Examples.

For instance, SRE, IL-2, NFAT, or Osteocalcin promoters can be substituted, alone or in combination (e.g., GAS/NF-KB/EGR, GAS/NF-KB, I1-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 14
High-Throughput Screening Assay for T-cell Activity

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 13. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+Th1 helper cells. In order to generate stable cell lines, approximately 2 million Jurkat cells are transfected with the GAS-SEAP/neo vector using DMRLE-C (Life Technologies)(transfection procedure described below). The transfected celis are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degree C for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing KDI polypeptides or KDI induced polypeptides as produced by the protocol described in Example 12.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degree C. until SEAP assays are performed according to Example 18. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 15
High-Throughput Screening Assay Identifying Myeloid Activity

The following protocol is used to assess myeloid activity of KDI by determining whether KDI proliferates and/or differentiates myeloid cells. Myeloid cell activity is assessed using the GAS/SEAP/Neo construct produced in Example 13. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 13, a DEAE-Dextran method (Kharbanda et. al., 1994, Cell Growth & Differentiation, 5:259–265) is used. First, harvest 2×10e7 U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCL (pH 7.4) buffer containing 0.5 mg/ml DEAE-Dextran, 8 ug GAS-SEAP2 plasmid DNA, 140 mM NaCl, 5 mM KCl, 375 uM Na2HPO4.7H2O, 1 mM MgCl2, and 675 uM CaCl2. Incubate at 37 degrees C. for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wasp with PBS. Suspend the cells in 200 ml above described growth medium, with a final density of $5 \times 10^5$ cells/ml. Plate 200 ul cells per well in the 96-well plate (or $10 \times 10^5$ cells/well).

Add 50 ul of the supernatant prepared by the protocol described in Example 12. Incubate at 37 degee C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 18.

Example 16
High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by KDI.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC=12 cells with a construct containing an EGR promoter linked to SEAP reporter, activation of PC=12 cells by KDI can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

5' GCGCTCGAGGGATGACAGCGATAGAA-
    CCCCGG-3' (SEQ ID NO:28)

5' GCGAAGCTTCGCGACTCCCCGGATCCG-
    CCTC-3' (SEQ ID NO:29)

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type 1 (Upstate Biotech Inc. Cat#08–115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC=12 using the Lipofectamine protocol described in Example 12. EGR-SEAP/PC=12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as 5×10⁵ cells/ml.

Add 200 ul of the cell suspension to each well of 96-well plate (equivalent to 1×10⁵ cells/well). Add 50 ul supernatant produced by Example 12, 37 degree C. for 48 to 72 hr. As a positive control, a growth factor known to activate PC=12 cells through EGR can be used, such as 50 ng/ul of Neuronal Growth Factor (NGF). Over fifty-fold induction of SEAP is typically seen in the positive control wells. SEAP assay the supernatant according to Example 18.

Example 17

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 12. Activators or inhibitors of NF-KB would be useful in treating, preventing, and/or diagnosing diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:30), 18 bp of sequence complementary to the 5' end of the SV40 early promoter sequence, and is flanked with an XhoI site:

5' :GCGGCCTCGAGGGGACTTTCCCGGG-
    GACTTTCCGGGGACTTTCCGGGACTTT CCATCCTGC-
    CATCTCAATTAG:3' (SEQ ID NO:31).

The downstream primer is complementary to the 3' end of the SV40 promoter and is flanked with a Hind III site:

5':GCGGCAAGCTTTTTGCAAAGCCTAGGC:3'(SEQ ID NO:26).

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5' :CTCGAGGGGACTTMCCCGGGGACTTTC-
    CGGGGACTTTCCGGGACTTTCCATCT GCCATCTCAATT-
    AGTCAGCAACCATAGTCCCGC-
    CCCTAACTCCGCCCATCCCGCC
    CCTAACTCCGCCCAGTTCCGCCCAT-
    TCTCCGCCCCATGGCTGACTAATTTTTTTTA TTTATGCA-
    GAGGCCGAGGCCGCCTCGGCCTCTGAGC-
    TATTCCAGAAGTAGTGAG
    GAGGCTTTTTTGGAGGCCTAGGCTTTTG-
    CAAAAAGCTT:3' (SEQ ID NO:32).

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 14. Similarly, the method for assaying supernatants with these stable Jurkat T-cells is also described in Example 14. As a positive control, exogenous TNF alpha (0.1, 1, 10 ng) is added to wells H9, H10, and H11, with a 5–10 fold activation typically observed.

Example 18

Assay for SEAP Activity

As a reporter molecule for the assays described in Examples 14–17, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 ul of 2.5×dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Alternatively, the amount of secreted alkaline phosphatase can be determined with the "SEAP Reporter Gene Assay—chemiluminescent" kit (Boehringer Mannheim), using disodium 3(4-methoxyspiro(1,2-dioxetane-3,2'-(5'chloro)tricyclo[3.3.1.1]decan)-4-yl)phenyl phosphate as the luminogenic substrate. Assays are performed in a 96-well microtiter plate following the manufacturer's guidelines, and are counted in a MLX, Microtiter Plate Luminometer (Dynex Technologies, Chantilly, Va.).

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 19

KDI in Vitro—ISRE Activation

The type I Interferons are known to signal through a common receptor complex, activate the Jak/STST signalling pathway, and ultimately activate transcription of interferon inducible genes. Upstream of these type I Interferon Inducible genes is an element known as the ISRE (Interferon Stimulated Response Element). To determine if KDI can also signal and activate the ISRE element, reporter genes containing an ISRE element (e.g., ISRE-SEAP or ISRE-CAT), are reduced transiently into a type I responsive interferon cell line. These transfected cell lines are then treated with KDI (supernatants, recombinant protein, transfected cells or membranes therefrom) and activation of the reporter gene is monitored.

293T cells or HeLa cells are transiently transfected with an ISRE-SEAP reporter construct using lipofectamine according to manafacturers instruction (LTI). Routinely 200,000 cells seeded in a 6 well dish are transfecetd. 24 hrs post-transfection, cells are treated with either conditioned supernatant or purified protein. 48 hrs post treatment, supernatants are harvesed and SEQP assays performed.

293T cells transfected with the ISRE-SEAP plasmid cells are challenged with supernatants or polypeptides from 293T cells transfected with various variants of KDI, in addition to a range of concentrations of IFN-alpha and IFN-beta known stimulators of the ISRE element as positive controls.

This shows whether KDI can activate the ISRE-SEAP reporter when cotransfected into 293T cells. For example, 293T cells are transfected with the ISRE-SEAP reporter construct along with the following plasmids: sKDI.L28-K207.FLAG; IFNa; KDI.L28-K207.

Compared to co-transfection with pC4, strong transcriptional activation can be observed with plasmids expessing IFN alpha, IFN beta and KDI. Construct comprised of KDI L28-K207.FLAG+KDI L28K207 may be able to activate ISRE even more strongly than IFN beta.

Example 20
KDI Cotransfection Activates the ISRE Signal Transduction Pathway Specifically To determine if KDI activates the ISRE pathway specifically, 293T cells are transfected with both the ISRE-SEAP reporter and the NFAT-SEAP reporter, that later of which contains multiple copies of the NFAT responsive element. KDI, IFN alpha and IFN beta were then cotransfected with each reporter plasmid and SEAP activity measured 48 hrs later. KDI, IFNa, and IFNb can activate the ISRE element 2–6000 fold. In contrast none of the molecules are capable of activating the NFAT responsive element, suggesting that like IFNa and IFNb, KDI activates the ISRE specifically. KDI with its own signal peptide may be quite potent.

Example 21
KDI Variants May Differ in Their Ability to Activate the ISRE Element Variants of KDI (e.g., KDI.L28 with the MPIF signal peptide; KDI.L28 with a C-terminal FLAG tag; and KDI with its natural signal peptide) are cotransfected with the ISRE-SEAP reporter and the level of activation determined 48 hrs post-transfection as compared to controls. KDI with its own signal peptide can be a potent activator of ISRE.

KDI.L28 can be used to activate the ISRE element in a dose responsive manner while the host strain control extract mediates no ISRE activation. SEAP activation is determined after 48 hrs. Full length KDI can be a potent activator of the ISRE reporter construct inducing activation greater than vector alone. Both the A182 deletion (which deletes terminal 25 aa) and the R192 deletion (which deletes the terminal 15 aa) are tested. C-terminal deletions of KDI may result in loss of activity.

Expression of KDI.M7 can be used to activate of the ISRE element in addition to KDI.M1. The translation of KDI could be from M1 or from M7. Translation from M1 or M7 in an optimal Kozak context directs expression of proteins that are potent activators of the ISRE. Therefore, KDI can be expressed either from M1 or from M7. The absence of a signal peptide on KDI can result in no ISRE activation, which shows that it may be required for KDI to be directed to the secretory pathway in order for it to be able to activate the ISRE element.

Example 22
High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to $2–5\times10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4 The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either KDI or a molecule induced by KDI, which has resulted in an increase in the intracellular Ca++ concentration.

Example 23
High-Throughput Screening Assay Identifying Tyrosine Kinase Activity The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether KDI or a molecule induced by KDI is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 12, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 40° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg2+ (5nM ATP/50 mM MgCl2), then 10 ul of 5×Assay Buffer (40 mM imidazole hydrochloride, pH7.3, 40 mM beta-glycerophosphate, 1 mM EGTA, 100 mM MgCl2, 5 mM MnCl2, 0.5 mg/ml BSA), then 5 ul of Sodium Vanadate(1 mM), and then 5 ul of water. Mix the components gently and preincubate the reaction mix at 30 degree C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 24

High-Throughput Screening Assay Identifying Phosphorylation Activity

As a potential alternative and/or compliment to the assay of protein tyrosine kinase activity described in Example 23, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-land Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by KDI or a molecule induced by KDI.

Example 25

Method of Determining Alterations in the KDI Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of KDI is also determined and genomic PCR products analyzed to confirm the results. PCR products harboring suspected mutations in KDI is then cloned and sequenced to validate the results of the direct sequencing.

PCR products of KDI are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in KDI not present in unaffected individuals.

Genomic rearrangements are also observed as a method of determining alterations in a gene corresponding to KDI. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the KDI genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Az.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomnic region of KDI (hybridized by the probe) are identified as insertions, deletions, and translocations. These KDI alterations are used as a diagnostic marker for an associated disease.

Example 26
Method of Detecting Abnormal Levels of KDI in a Biological Sample

KDI polypeptides can be detected in a biological sample, and if an increased or decreased level of KDI is detected, this polypeptide is a marker for a particular phenotype. Methods of detection are numerous, and thus, it is understood that one skilled in the art can modify the following assay to fit their particular needs.

For example, antibody-sandwich ELISAs are used to detect KDI in a sample, preferably a biological sample. Wells of a microtiter plate are coated with specific antibodies to KDI, at a final concentration of 0.2 to 10 ug/ml. The antibodies are either monoclonal or polyclonal and are produced by the method described in Example 11. The wells are blocked so that non-specific binding of KDI to the well is reduced.

The coated wells are then incubated for>2 hours at RT with a sample containing KDI. Preferably, serial dilutions of the sample should be used to validate results. The plates are then washed three times with deionized or distilled water to remove unbounded KDI.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot KDI polypeptide concentration on the X-axis (log scale) and fluorescence or absorbance of the Y-axis (linear scale). Interpolate the concentration of the KDI in the sample using the standard curve.

Example 27
Formulation

The invention also provides methods of treatment and/or prevention of diseases, disorders, and/or conditions (such as, for example, any one or more of the diseases, disorders, and/or conditions disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also he employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(–)-3-hydroxybutyric acid (EP 133,988).

Sustained-release Therapeutics also include liposomally entrapped Therapeutics of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; apanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engi. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA;

sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, 5 sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be admninistered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be admninistered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETMBUTOL™, RIFABUTIN™, CLARITHROMYCIN™, AZITHROMYCIN™, GANCICLOVIR™, FOSCARNET™, CIDOFOVFR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation. In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAW™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory a-gent. Anti-inflanunatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamiwdes, e-acetaniidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeu tic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chiorotrianisene, and testolactone); nitrogen mustard derivatives (e.g., mephalen, chorambucil, mechiorethamine (nitroen mustard) and thiotepa); steroids and combinations (e.g., bethamnethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PIGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 28
Method of Treating Decreased Levels of KDI

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of KDI in an individual can be treated by administering KDI, preferably in the secreted form. Thus, the invention also provides a method of treatment of an individual in need of an increased level of KDI polypeptide comprising administering to such an individual a Therapeutic comprising an amount of KDI to increase the activity level of KDI in such an individual.

For example, a patient with decreased levels of KDI polypeptide receives a daily dose 0.1–100 ug/kg of the polypeptide for six consecutive days. Preferably, the polypeptide is in the secreted form. The exact details of the dosing scheme, based on administration and formulation, are provided in Example 27.

Example 29
Method of Treating Increased Levels of KDI

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of KDI. This technology is one example of a method of decreasing levels of KDI polypeptide, preferably a secreted form, due to a variety of etiologies, such as cancer.

For example, a patient diagnosed with abnormally increased levels of KDI is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 27.

Example 30
Method of Treatment Using Gene Therapy—Ex Vivo

One method of gene therapy transplants fibroblasts, which are capable of expressing KDI polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding KDI can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted KDI.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the KDI gene is then added to the media and the packaging cells transduced with the vector. The packaging cells now produce infectious viral particles containing the KDI gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether KDI protein is produced.

The engineered fibroblasts are then transplanted onto the host, either alone or after having been grown to confluence on cytodex 3 microcarrier beads.

Example 31
Gene Therapy using Endogenous KDI Gene

Another method of gene therapy according to the present invention involves operably associating the endogenous KDI sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous KDI, flanking the promoter. The targeting sequence will be sufficiently near the 5' end of KDI so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous KDI sequence. This results in the expression of KDI in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the KDI locus, plasmid pUC18 (MBI Fermentas, Amherst, N.Y.) is digested with HindIII. The CMV promoter is amplified by PCR with an XbaI site on the 5' end and a BamHI site on the 3'end. Two KDI non-coding sequences are amplified via PCR: one KDI non-coding sequence (KDI fragment 1) is amplified with a HindIII site at the 5' end and an Xba site at the 3'end; the other KDI non-coding sequence (KDI fragment 2) is amplified with a BamHI site at the 5'end and a HindIII site at the 3'end. The CMV promoter and KDI fragments (1 and 2) are digested with the appropriate enzymes (CMV promoter—XbaI and BamHI; KDI fragment 1—XbaI; KDI fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 32
Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) KDI sequences into an animal to increase or decrease the expression of the KDI polypeptide. The KDI polynucleotide may be operatively linked to a promoter or any other genetic elements necessary for the expression of the KDI polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The KDI polynucleotide constructs may be delivered by any method that delivers injectable materials to the cells of an animal, such as, injection into the interstitial space of tissues (heart, muscle, skin, lung, liver, intestine and the like). The KDI polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the KDI polynucleotides may also be delivered in liposome formulations (such as those taught in Feigner P. L. et al. (1995) Ann. NY Acad. Sci. 772:126–139 and Abdallah B. et al. (1995) Biol. Cell 85(1):1–7) which can be prepared by methods well known to those skilled in the art.

The KDI polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The KDI polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked KDI polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked KDI polynucleotide constructs can be delivered to arteries during angioplasty by the catheter used in the procedure.

The dose response effects of injected KDI polynucleotide in muscle in vivo is determined as follows. Suitable KDI template DNA for production of mRNA coding for KDI polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The KDI template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for KDI protein expression. A time course for KDI protein expression may be done in a similar fashion except that quadriceps from different mice are harvested at different times. Persistence of KDI DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using KDI naked DNA.

Example 33

KDI Transgenic Animals

The KDI polypeptides can also be expressed in transgenic animals. Animals of any species, including, but not limited to, mice, rats, rabbits, hamsters, guinea pigs, pigs, micropigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Any of the KDI polypeptides disclose throughout this application can be used to generate transgenic animals. For example, DNA encoding amino acids C30-K207 of SEQ ID NO:2 can be inserted into a vector containing a promoter, such as the actin promoter, which will ubiquitously express the inserted fragment. Primers that can be used to generate such fragments include a 5' primer containing a BamHI restriction site shown in bold:

GGCCG GGATCC GCCATCATGAGCACCAAA-
   CCRGATATG                          (SEQ ID NO:18)

and a 3' primer, containing a Asp718 restriction site shown in bold:

GCGCGC GGTACC TTATCTTCTGATTTCCA-
   CTCGGA                             (SEQ ID NO:33).

This construct will express the predicted extracellular domain of KDI under the control of the actin promoter for ubiquitous expression. The region of KDI included in this construct extends from C30-K207 of SEQ ID NO:2.

Similarly, the DNA encoding the full length KDI protein can also be inserted into a vector using the following primers: A 5' primer containing a BamHI restriction site shown in bold:

GGCCG GGATCC GCCATCATGAGCACCAAA-
   CCTGATATG                          (SEQ ID NO:18)

and a 3' primer, containing an Asp718 restriction site shown in bold:

GGCCGC GGTACC TTATTTCCTCCTGAATA-
   GAGC                               (SEQ ID NO: 17).

Besides these two examples, other fragments of KDI can also be inserted into a vector to create transgenics having ubiquitous expression.

Alternatively, polynucleotides of the invention can be inserted in a vector which controls tissue specific expression through a tissue specific promoter. For example, a construct having a transferrin promoter would express the KDI polypeptide in the liver of transgenic animals. Therefore, DNA encoding amino acids C30-K207 of SEQ ID NO:2 can be amplified using a 5' primer, having a BamHI restriction site shown in bold:

GGCCG GGATCC GCCATCATGAGCACCAAA-
   CCTGATATG                          (SEQ ID NO:18), and a 3' primer, containing a Asp718 restriction site shown in bold:

GCGCGC GGTACC TTATCTTCTGATTTCCA-
   CTCGGA                             (SEQ ID NO:23).

Similarly, the DNA encoding the full length KDI protein can also be inserted into a vector for tissue specific expression using the following primers: A 5' primer containing a BamHI restriction site shown in bold:

GGCCG GGATCC GCCATCATGAGCACCAAA-
   CCTGATATG                          (SEQ ID NO:18)

and a 3' primer, containing an Asp718 restriction site shown in bold:

GGCCGC GGTACC TTATTTCCTCCTGAATAG-
   AGC                                (SEQ ID NO:17).

In addition to expressing the polypeptide of the present invention in a ubiquitous or tissue specific manner in transgenic animals, it would also be routine for one skilled in the art to generate constructs which regulate expression of the polypeptide by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of KDI polypeptides, studying diseases, disorders, and/or conditions associated with aberrant KDI expression, and in screening for compounds effective in ameliorating such diseases, disorders, and/or conditions.

Example 34
KDI Knock-Out Animals

Endogenous KDI gene expression can also be reduced by inactivating or "knocking out" the KDI gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the KDI polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of KDI polypeptides, studying diseases, disorders, and/or conditions associated with aberrant KDI expression, and in screening for compounds effective in ameliorating such diseases, disorders, and/or conditions.

Example 35
Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay

Purified KDI protein, or truncated forms thereof, is assessed for its ability to induce activation, proliferation, differentiation or inhibition and/or death in B-cell populations and their precursors. The activity of KDI protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay

BALB/c mice are injected (i.p.) twice per day with buffer only, or 2 mg/Kg of KDI protein, or truncated forms thereof. Mice receive this treatment for 4 consecutive days, at which time they are sacrificed and various tissues and serum collected for analyses. Comparison of H&E sections from normal and KDI protein-treated spleens identify the results of the activity of KDI protein on spleen cells, such as the diffusion of peri-arterial lymphatic sheaths, and/or significant increases in the nucleated cellularity of the red pulp regions, which may indicate the activation of the differentiation and proliferation of B-cell populations. Inmmunohistochemical studies using a B cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from KDI protein-treated mice is used to indicate whether KDI protein specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and KDI protein-treated mice.

The studies described in this example tested activity in KDI protein. However, one skilled in the art could easily modify the exemplified studies to test the activity of KDI polynucleotides (e.g., gene therapy), agonists, and/or antagonists of KDI.

Example 36
T Cell Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells (5×10$^4$/well) of mAb coated plates in RPMI containing 10% FCS and P/S in the presence of varying concentrations of KDI protein (total volume 200 μl). Relevant protein buffer and medium alone are controls. After 48 hr. culture at 37° C., plates are spun for 2 min. at 1000 rpm and 100 μl of supernatant is removed and stored −20° C. for measurement of IL-2 (or other cytokines) if effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of KDI proteins.

The studies described in this example tested activity in KDI protein. However, one skilled in the art could easily modify the exemplified studies to test the activity of KDI polynucleotides (e.g., gene therapy), agonists, and/or antagonists of KDI.

Example 37
Effect of KDI on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of KDI or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of ThI helper T-cell immune response, and induces cytotoxic T and NK cell function. An ELISA is used to measure the IL-12 release as follows. Dendritic cells (10$^6$/ml) are treated with increasing concentrations of KDI for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of KDI or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. KDI, agonists, or antagonists of KDI can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×10$^6$/ml in PBS containing PI at a final concentration of 5 μg/ml, and then incubaed at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×105 cells/ml with increasing concentrations of KDI and under the same conditions, but in the absence of KDI. For IL-12 production, the cells are primed overnight with IFN (100 U/ml) in presence of KDI. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst. Purified monocytes are plated in 96-w plate at $2-1\times10^5$ cell/well. Increasing concentrations of KDI are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in KDI protein. However, one skilled in the art could easily modify the exemplified studies to test the activity of KDI polynucleotides (e.g., gene therapy), agonists, and/or antagonists of KDI.

Example 38
KDI Biological Effects Astrocyte and Neuronal Assays

Recombinant KDI, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate KDI's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of KDI to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or KDI with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or KDI with or without IL-1α for 24 hours. The supernatants are collected and assayed for IL-6 by ELISA kit (Endogen, Cambridge, Mass.).

Human lung fibroblasts are cultured with FGF-2 or KDI for 3 days in basal medium before the addition of Alamar Blue to assess effects on growth of the fibroblasts. FGF-2 should show a stimulation at 10–2500 ng/ml which can be used to compare stimulation with KDI.

Parkinson Models

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, KDI can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of KDI is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if KDI acts to prolong the survival of dopaminergic neurons, it would suggest that KDI may be involved in Parkinson's Disease.

The studies described in this example tested activity in KDI protein. However, one skilled in the art could easily modify the exemplified studies to test the activity of KDI polynucleotides (e.g., gene therapy), agonists, and/or antagonists of KDI.

Example 39
The Effect of KDI on the Growth of Vascular Endothelial Cells

On day 1, human umbilical vein endothelial cells (HUVEC) are seeded at $2-5\times10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. KDI protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that KDI may proliferate vascular endothelial cells.

The studies described in this example tested activity in KDI protein. However, one skilled in the art could easily modify the exemplified studies to test the activity of KDI polynucleotides (e.g., gene therapy), agonists, and/or antagonists of KDI.

Example 40
Stimulatory Effect of KDI on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or KDI in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity in KDI protein. However, one skilled in the art could easily modify the exemplified studies to test the activity of KDI polynucleotides (e.g., gene therapy), agonists, and/or antagonists of KDI.

Example 41
Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on 4-chamber slides are pulsed with 10% calf serum as a positive control, or dilutions of the polypeptide of the present invention, and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. See, Ellwart and Dormer, Cytometry, 6:513–20 (1985), herein incorporated by reference in its entirety.

The studies described in this example tested activity in KDI protein. However, one skilled in the art could easily modify the exemplified studies to test the activity of KDI polynucleotides (e.g., gene therapy), agonists, and/or antagonists of KDI.

Example 42
Stimulation of Endothelial Migration

This example will be used to explore the possibility that KDI may stimulate lymphatic endothelial cell migration.

Endothelial cell migration assays are performed using a 48 well microchemotaxis chamber (Neuroprobe Inc., Cabin John, MD; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5\times10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity in KDI protein. However, one skilled in the art could easily modify the exemplified studies to test the activity of KDI polynucleotides (e.g., gene therapy), agonists, and/or antagonists of KDI.

Example 43
Stimulation of Nitric Oxide Production by Endothelial Cells

Nitric oxide released by the vascular endothelium is believed to be a mediator of vascular endothelium relaxation. Thus, KDI activity can be assayed by determining nitric oxide production by endothelial cells in response to KDI.

Nitric oxide is measured in 96-well plates of confluent microvascular endothelial cells after 24 hours starvation and a subsequent 4 hr exposure to various levels of a positive control (such as VEGF-1) and KDI. Nitric oxide in the medium is determined by use of the Griess reagent to measure total nitrite after reduction of nitric oxide-derived nitrate by nitrate reductase. The effect of KDI on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$$2KNO_2 + 2KI + 2H_2SO_4 \rightarrow 2NO + I_2 + 2H_2O + 2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217:96–105 (1995).

The studies described in this example tested activity in KDI protein. However, one skilled in the art could easily modify the exemplified studies to test the activity of KDI polynucleotides (e.g., gene therapy), agonists, and/or antagonists of KDI.

Example 44
Effect of KDI on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or KDI (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity in KDI protein. However, one skilled in the art could easily modify the exemplified studies to test the activity of KDI polynucleotides (e.g., gene therapy), agonists, and/or antagonists of KDI.

Example 45
Angiogenic Effect on Chick Chorioallantoic Membrane

Chick chorioallantoic membrane (CAM) is a well-established system to examine angiogenesis. Blood vessel formation on CAM is easily visible and quantifiable. The ability of KDI to stimulate angiogenesis in CAM can be examined.

Fertilized eggs of the White Leghorn chick (Gallus gallus) and the Japanese qual (Coturnix cotumnix) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity in KDI protein. However, one skilled in the art could easily modify the exemplified studies to test the activity of KDI polynucleotides (e.g., gene therapy), agonists, and/or antagonists of KDI.

Example 46
Angiogenesis Assay Using a Matrigel Implant in Mouse

In vivo angiogenesis assay of KDI measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with KDI at 150 ng/ml at 4 degree C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity in KDI protein. However, one skilled in the art could easily modify the exemplified studies to test the activity of KDI polynucleotides (e.g., gene therapy), agonists, and/or antagonists of KDI.

Example 47
Rescue of Ischemia in Rabbit Lower Limb Model

To study the in vivo effects of KDI on ischemia, a rabbit hindlimb ischemia model is created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked KDI expression plasmid by arterial gene transfer technology using a hydrogel-coated balloon catheter as described (Riessen, R. et al. *Hum Gene Ther.* 4:749–758 (1993); Leclerc, G. et al. *J. Clin. Invest.* 90:936–944 (1992)). When KDI is used in the treatment, a single bolus of 500 mg KDI protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity in KDI protein. However, one skilled in the art could easily modify the exemplified studies to test the activity of KDI polynucleotides (e.g., gene therapy), agonists, and/or antagonists of KDI.

Example 48
Effect of KDI on Vasodilation

Since dilation of vascular endothelium is important in reducing blood pressure, the ability of KDI to affect the blood pressure in spontaneously hypertensive rats (SHR) is examined. Increasing doses (0, 10, 30, 100, 300, and 900 mg/kg) of the KDI are administered to 13–14 week old spontaneously hypertensive rats (SHR). Data are expressed as the mean +/- SEM. Statistical analysis are performed with a paired t-test and statistical significance is defined as p<0.05 vs. the response to buffer alone.

The studies described in this example tested activity in KDI protein. However, one skilled in the art could easily modify the exemplified studies to test the activity of KDI polynucleotides (e.g., gene therapy), agonists, and/or antagonists of KDI.

Example 49
Rat Ischemic Skin Flap Model

The evaluation parameters include skin blood flow, skin temperature, and factor VIII immunohistochemistry or endothelial alkaline phosphatase reaction. KDI expression, during the skin ischemia, is studied using in situ hybridization.

The study in this model is divided into three parts as follows:
a) Ischemic skin
b) Ischemic skin wounds
c) Normal wounds
The experimental protocol includes:
a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with KDI of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

The studies described in this example tested activity in KDI protein. However, one skilled in the art could easily modify the exemplified studies to test the activity of KDI polynucleotides (e.g., gene therapy), agonists, and/or antagonists of KDI.

Example 50
Peripheral Arterial Disease Model

Angiogenic therapy using KDI is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.

b) KDI protein, in a dosage range of 20 mg–500 mg, is delivered intravenously and/or intramuscularly 3 times (perhaps more) per week for 2–3 weeks.

c) The ischemic muscle tissue is collected after ligation of the femoral artery at 1, 2, and 3 weeks for the analysis of KDI expression and histology. Biopsy is also performed on the other side of normal muscle of the contralateral hindlimb.

The studies described in this example tested activity in KDI protein. However, one skilled in the art could easily modify the exemplified studies to test the activity of KDI polynucleotides (e.g., gene therapy), agonists, and/or antagonists of KDI.

Example 51
Ischemic Myocardial Disease Model

KDI is evaluated as a potent mitogen capable of stimulating the development of collateral vessels, and restructuring new vessels after coronary artery occlusion. Alteration of KDI expression is investigated in situ. The experimental protocol includes:

a) The heart is exposed through a left-side thoracotomy in the rat. Iummediately, the left coronary artery is occluded with a thin suture (6–0) and the thorax is closed.

b) KDI protein, in a dosage range of 20 mg–500 mg, is delivered intravenously and/or intramuscularly 3 times (perhaps more) per week for 2–4 weeks.

c) Thirty days after the surgery, the heart is removed and cross-sectioned for morphometric and in situ analyzes.

The studies described in this example tested activity in KDI protein. However, one skilled in the art could easily modify the exemplified studies to test the activity of KDI polynucleotides (e.g., gene therapy), agonists, and/or antagonists of KDI.

Example 52
Rat Corneal Wound Healing Model

This animal model shows the effect of KDI on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of KDI, within the pocket.

e) KDI treatment can also be applied topically to the corneal wounds in a dosage range of 20 mg–500 mg (daily treatment for five days).

The studies described in this example tested activity in KDI protein. However, one skilled in the art could easily modify the exemplified studies to test the activity of KDI polynucleotides (e.g., gene therapy), agonists, and/or antagonists of KDI.

Example 53

Diabetic Mouse and Glucocorticoid-Impaired Wound Healing Models

A. Diabetic db+/db+ Mouse Model

To demonstrate that KDI accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (*Suppl*): 1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

KDI is administered using at a range different doses of KDI, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated; and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm$^2$, the corresponding size of the dermal punch. Calculations are made using the following formula:

$$[\text{Open area on day 8}]-[\text{Open area on day 1}]/[\text{Open area on day 1}]$$

Specimens are fixed in 10% buffered formalin and paraffin embedded blocks are sectioned perpendicular to the wound surface (5mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with KDI. This assessment included verification of the presence of cell accumulation, inflammatory cells, capillaries, fibroblasts, re-epithelialization and epidermal maturity (Greenhalgh, D. C. et al, *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that KDI can accelerate the healing process, the effects of multiple topical applications of KDI on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

KDI is administered using at a range different doses of KDI, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) KDI treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with KDI. A calibrated lens micrometer is used by a blinded observer to determine the distance of the wound gap.

Experimental data are analyzed using an unpaired t test. A p value of <0.05 is considered significant.

The studies described in this example tested activity in KDI protein. However, one skilled in the art could easily modify the exemplified studies to test the activity of KDI polynucleotides (e.g., gene therapy), agonists, and/or antagonists of KDI.

Example 54

Lymphadema Animal Model

The purpose of this experimental approach is to create an appropriate and consistent lymphedema model for testing the therapeutic effects of KDI in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements

Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements

On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma Protein Measurements

Blood is drawn, spun, and serum separated prior to surgery and then at conclusion for total protein and Ca2+ comparison.

Limb Weight Comparison

After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations

The transverse muscle located behind the knee (popliteal) area is dissected and arranged in a metal mold, filled with freezeGel, dipped into cold methylbutane, placed into labeled sample bags at −80° C. until sectioning. Upon sectioning, the muscle is observed under fluorescent microscopy for lymphatics.

The studies described in this example tested activity in KDI protein. However, one skilled in the art could easily modify the exemplified studies to test the activity of KDI polynucleotides (e.g., gene therapy), agonists, and/or antagonists of KDI.

Example 55

Suppression of TNF Alpha-induced Adhesion Molecule Expression by KDI

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of KDI to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 $\mu$l of 0.1% paraformaldehyde-PBS(with Ca++ and Mg++) is added to each well. Plates are held at 4° C. for 30 min.

Fixative is then removed from the wells and wells are washed 1×0 with PBS(+Ca,Mg)+0.5% BSA and drained. Do not allow the wells to dry. Add 10 $\mu$l of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 µl of diluted ExtrAvidin-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$ 0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng, 1.74 ng; 0.55 ng; 0.18 ng]. Results are indicated as amount of bound AP-conjugate in each sample.

The studies described in this example tested activity in KDI protein. However, one skilled in the art could easily modify the exemplified studies to test the activity of KDI polynucleotides (e.g., gene therapy), agonists, and/or antagonists of KDI.

Example 56
Anti-viral Activity of KDI

Normal human dermal fibroblasts are treated with supernatants or KDI polypeptide expressed from the various constructs described herein. After 24 hours, cells are infected with encephalomyocarditis virus. Following an additional 24 hours incubation, surviving cells are stained with crystal violet. The optical density of the wells containing the treated cells is read at 580 nm. Antiviral activity is expressed in units/ml. One unit is defined as the amount of protein which protects 50% of the cells from the cytopathic effects caused by the virus. The positive control employed is recombinant IFN-beta.

In several experiments, preparations of recombinant KDI containing 2% SDS were found to have protective activity. The positive control employed was a similar preparation of IFN-β containing 2% SDS.

Example 57
Anti-proliferation Activity of KDI

Supernatants from transient transfections or purified KDI protein is utilized to determine the anti-prolifative effect of KDI on a range of cell lines including hematopoietic and non-hematopoeitic cell types. Type I Interferons are known to mediate antigrowth responses. As lymphoblastoid Daudi cells are very sensitive to the antiproliferative effects of IFNa, these cells are tested with or without conditioned supernatants generated from stable cell lines expressing various KDI variants or purified KDI protein.

Daudi cells were incubated with KDI containing supernatants. The number of viable cells was then determined up to 7 days. Similarly, 293T cells were seeded into a 96 well plate at a range of cell densities (2000, 5000, 10000) per well; allowed to settle onto the plate and then treated with conditioned supernatant from CHO cells stably transfected pC4, IL2; full length KDI (which is cleaved at L28) and KDI.L28 (with heterologous signal peptide). A 0.5× concentartion of the supernatant was tested. In addition, supernatant from 293T cells transiently transfected with IFNa and IFNb were also tested. Cells were treated for 48 hrs and then the level of proliferating cells are determined by alamarBlue staining.

Example 58
KDI In Vitro—Effect on Monocyte Activity

IFN-alpha, IFN-beta and especially IFN-gamma play an important role in monocyte/macrophage activation. The potential activity of KDI as a class I interferon is assessed in three functional assays using monocytes: cytokine release, oxidative burst, and the effect on antigen expression.

Cytokine Release from Monocytes

Several studies have indicated that IFN-alpha and IFN-gamma exert differential effect on the production of TNF-alpha and IL-10 by monocytes in response to bacterial stimuli. INF-alpha was reported to antagonize the IFN-gamma synergist effect on TNF-alpha release in LPS treated monocytes. Monocytes are treated for 24 hours with KDI containing supernatants or KDI proteins in absence or presence of LPS and IFN-gamma. Secretion of TNF-alpha and IL-10 in the monocyte conditioned medium is analyzed by ELISA.

Oxidative Burst

IFN-alpha is a known antagonist of IFN-gamma-induced oxidative burst in monocytes. Monocytes are incubated for 3 days with KDI containing supernatants or KDI proteins in absence or presence of IFN-gamma. Hydrogen peroxide release from the cells is measured by the horseradish peroxidase-dependent oxidation of phenol red added to the cell cultures in the last 3 hours of incubation.

Effect on Expression of Surface Antigens

Monocytes are incubated for 3 days with KDI along with the positive controls of IFN-beta or alpha. The level of expression of molecules important for antigen presentation, or indicative of an activation state (such as MHC class II and the class I antigens, CD80, CD40, CD54, and Fc receptors) is evaluated by fluorescent activated cell sorting (FACS) of the treated cells.

Example 59
KDI In Vitro—Effect on NK Cell Function

NK cells can be activated without previous sensitization. They are therefore in the first line of defense against infectious agents and tumor cells. NK cell activity is enhanced by IFN-alpha, and to a lesser extent by INF-gamma. The ability of KDI to modulate NK cell activity is examined initially with KDI containing culture supernatants and then with recombinant KDI protein.

The effect of KDI on NK cell function is evaluated using two assays: (1) IFN-gamma release and (2) NK cytotoxic activity. For INF-gamma release, peripheral blood lymphocytes (PBLs) are obtained from the non-adherent fraction of peripheral blood mononuclear cells. Cells are incubated (1 million/ml) for 1 day in presence of KDI supernatants or proteins of the present invention. Supernatatns are collected and the IFN-gamma content in the culture conditioned media is assayed by ELISA. The positive control is IFN-alpha. For the NK cytotoxicity, the effector PBLs are harvested and incubated for 4 hours with $^{51}$Cr-labeled K562 target cells. The amount of radioactivity released from the target cells is a measure of the cytotoxic activity of the KDI-treated effector cells. The positive control is IFN-alpha.

Example 60
KDI In Vitro—Effect on Dendritic Cells

Dendritic cells (DC) are the most efficient antigen-presenting cells. Type I IFN has been reported to induce dentritic cell maturation. Dendritic cells are obtained from human peripheral blood cultured for 7–10 days in the presence of GM-CSF and IL-4. Several assays are used to analyze the effect of KDI on dendritic cell activation and maturation.

Chemotaxis

Cells are labeled with calcein-AM and are added to the upper chamber of a 96-well chemotaxis plate. Different concentrations of KDI are added in the bottom chamber of each well. After incubation for 90 minutes at 37° C., migrated cells are quantitated using a fluorescence plate reader. The ratio between the number of cells that migrate in presence of KDI and the number of the cells that migrate in presence of buffer control is defined as chemotactic index. MIP-1alpha is used as a positive control.

Endocytosis

Dendritic cells are treated with KDI for 3 days. Dendritic cells ($2\times10^5$ cells/determination) are then incubated for 2 h at 37° C. with 1 mg/ml FITC-dextran. Cells are washed twice and fixed with 1% formaldehyde. The FITC-dextran uptake of 10,000 cells is evaluated by a FACScan. TNF-alpha is used as a positive control.

Analysis of Surface Antigen Expression

Dendritic cells are treated with KDI for 3 days. The level of expression of molecules important for antigen presentation, or indicative of an activation state (such as MHC class II antigens, CD86, CD40, and CD54) and the maturation antigen CD83 are evaluated by fluorescent activated cell sorting (FACS) of the treated cells.

ELISA for Cytokine and Chemokine Release

Dendritic cells are treated with KDI for 3 days. Culture supernatants are removed and assayed for the presence of MIP-1alpha, TNF-alpha, IL-12 or other cytokines. As a positive control, the cells are stimulated with anti-CD40 antibody or LPS.

Mixed Leukocyte Reaction

Dendritic cells are treated with KDI for 3 days. Cells are then irradiated or mitomycin C-treated to prevent proliferation. T cells, purified from peripheral blood, are seeded in 96-well plates with increasing concentrations of Dendritic cells. T cell proliferation is measured by [$^3$H]thymidine incorporation. TNF-alpha is used as a positive control.

Example 61

KDI In Vitro—Effect on T Cells

The effect of KDI on the proliferation of primary human lymphocytes is evaluated. Cells are treated with PHA overnight. The resultant blasts are then treated with KDI for 3 days. Cell proliferation is measured by [$^3$H]thymidine incorporation or Alamar Blue staining. IFN-alpha is employed as a positive control.

Example 62

KDI In Vitro—Effect on B Cells

Proliferation and Immunoglobulin Secretion

Human tonsillar B cells are treated with KDI and pokeweed mitogen. Cell proliferation is measured by [$^3$H] thymidine incorporation of the treated cells. Culture supernatants are collected and analyzed for immunoglobulin content by ELISA. IFN-alpha is employed as a positive control.

Inhibition of Apoptosis

Cells of the BL cell line are incubated with ionomycin to induce apoptosis before being cultured in presence of KDI. Quantitative assessment of the cells undergoing apoptosis is determined by FACs. IFN-alpha is employed as a positive control.

Example 63

KDI In Vitro—Effect on Keratinocytes

Release of Cytokines and sICAM-1

Subconfluent keratinocytes are treated for 1–2 days with KDI in absence or presence of TNF-alpha. Cell-free supernatants are collected. The presence of sICAM-1, cytokines and chemokines (such as IL-1, TNF-alpha, GM-CSF, IL-6 and IL-8) is determined using commercially available ELISA kits. Either IFN-alpha or IFN-gamma is employed as a positive control.

The Effect on the Expression of Surface Antigens

Keratinocytes are incubated for 3 days with KDI or IFN-gamma, which is used as positive control. The level of expression of molecules important for antigen presentation (such as MHC class II) or ICAM-1 is evaluated by FACs of the treated cells.

The Generation of Primary Allogeneic T Cell Response

T cells purified from peripheral blood are incubated with fixed KDI-treated keratinocytes. The proliferation of T cells is assessed after a 6-day culture by pulsing with [$^3$H] thymidine.

Example 64

Identification of Genes Differentially Regulated by KDI using Oligonucleotide Arrays The pleiotropic activities of interferons are mediated primarily through the transcriptional regulation of many downstream effector genes. The mRNA profiles of various cell lines, including keratinocytes, fibroblasts and Daudi cells, after KDI treatment, as compared to IFN-α, -β, or -γ, is determined using oligonucleotide arrays with probe sets corresponding to thousands of human genes. See Der, S. D., et al., Proc. Natl. Acad Sci. USA 95:15623–28 (1998), which is incorporated herein by reference in its entirety. Among the probe sets used are transcripts for known IFN-stimulated genes, as identified in Der, et al. In this way, novel KDI-stimulated genes and KDI-repressed genes may be identified. Also, the differential induction of genes in response to KDI, as compared to other IFNs is assessed. Further, by assaying a variety of cell types, the cell-specificity of KDI's various activities can be evaluated.

Gene expression is monitored by hybridizing labeled RNA populations to high-density arrays of oligonucleotides, synthesized on a glass substrate by the combination of photolithography and oligonucleotide chemistry. Pease, A. C. et al., Proc. Natl. Acad., Sci. USA 91:5022 (1991). Oligonucleotide arrays containing probe sets for several thousand human genes are used to assay for changes in mRNA expression after stimulation of the keratinocyte, fibroblast, Daudi cell or other cell types with KDI or IFN-α, -β, or -γ, controls. The genes that are identified as being differentially expressed include genes whose expression levels changed from nondetectable in untreated cells to detectable in KDI-treated cells. Cutoff criteria depend on the level of signal obtained. For example, mRNA levels for certain genes that change more than 3-fold after a six hour exposure can be used to identify the up-regulated genes. The differential responsiveness to KDI in a cell type-specific manner is assessed in a similar fashion.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

What is claimed is:

1. An isolated protein comprising a polypeptide having an amino acid sequence selected from the group consisting of:
    (a) amino acids 1 to 207 of SEQ ID NO:2;
    (b) amino acids 7 to 207 of SEQ ID NO:2;
    (c) amino acids 2 to 207 of SEQ ID NO:2; and
    (d) amino acids 28 to 207 of SEQ ID NO:2.

2. The isolated protein of claim 1, wherein said amino acid sequence is (a).

3. The isolated protein of claim 1, wherein said amino acid sequence is (b).

4. The isolated protein of claim 1, wherein said amino acid sequence is (c).

5. The isolated protein of claim 1, wherein said amino acid sequence is (d).

6. The isolated protein of claim 1, wherein the polypeptide further comprises a heterologous polypeptide sequence.

7. The isolated protein of claim 6, wherein the heterologous polypeptide sequence is the Fc domain of an immunoglobulin.

8. The protein of claim 1, wherein said protein is glycosylated.

9. The protein of claim 1, wherein said protein is pegylated.

10. A composition comprising the protein of claim 1 and a acceptable carrier.

11. The composition of claim 10, wherein the composition further comprises a liposome.

12. A protein produced by a method comprising:
    (a) expressing the protein of claim 1 by a cell; and
    (b) recovering the protein.

13. An isolated protein comprising a polypeptide having an amino acid sequence selected from the group consisting of:
    (a) the amino acid sequence of the full-length polypeptide encoded by the cDNA contained in ATCC Deposit No. 203500; and
    (b) the amino acid sequence of the full-length polypeptide encoded by the cDNA contained in ATCC Deposit No. 203500 excluding the N-terminal methionine residue.

14. The isolated protein of claim 13, wherein said amino acid sequence is (a).

15. The isolated protein of claim 13, wherein said amino acid sequence is (b).

16. The isolated protein of claim 13, wherein the polypeptide further comprises a heterologous polypeptide sequence.

17. The isolated protein of claim 16, wherein the heterologous polypeptide sequence is the Fc domain of an immunoglobulin.

18. The protein of claim 13, wherein said protein is glycosylated.

19. The protein of claim 13, wherein said protein is pegylated.

20. A composition comprising the protein of claim 13 and a acceptable carrier.

21. The composition of claim 20, wherein the composition further comprises a liposome.

22. A protein produced by a method comprising:
(a) expressing the protein of claim 13 by a cell; and
(b) recovering the protein.

23. An isolated protein possessing anti-viral activity, comprising a polypeptide having an amino acid sequence at least 90% or more identical to an amino acid sequence selected from the group consisting of:
(a) amino acids 1 to 207 of SEQ ID NO:2;
(b) amino acids 7 to 207 of SEQ ID NO:2;
(c) amino acids 2 to 207 of SEQ ID NO:2; and
(d) amino acids 28 to 207 of SEQ ID NO:2.

24. The isolated protein of claim 23, which comprises a polypeptide having an amino acid sequence at least 90% or more identical to amino acid sequence (a).

25. The isolated protein of 23, which comprises a polypeptide having an amino acid sequence at least 95% or more identical to amino acid sequence (a).

26. The isolated protein of claim 23, which comprises a polypeptide having an amino acid sequence at least 90% or more identical to amino acid sequence (b).

27. The isolated protein of claim 23, which comprises a polypeptide having an amino acid sequence at least 95% or more identical to amino acid sequence (b).

28. The isolated protein of claim 23, which comprises a polypeptide having an amino acid sequence at least 90% or more identical to amino acid sequence (c).

29. The isolated protein of claim 23, which comprises a polypeptide having an amino acid sequence at least 95% or more identical to amino acid sequence (c).

30. The isolated protein of claim 23, which comprises a polypeptide having an amino acid sequence at least 90% or more identical to amino acid sequence (d).

31. The isolated protein of claim 23, which comprises a polypeptide having an amino acid sequence at least 95% or more identical to amino acid sequence (d).

32. The isolated protein of claim 23, wherein the polypeptide further comprises a heterologous polypeptide sequence.

33. The isolated protein of claim 32, wherein the heterologous polypeptide sequence is the Fc domain of an immunoglobulin.

34. The protein of claim 23, wherein said protein is glycosylated.

35. The protein of claim 23, wherein said protein is pegylated.

36. A composition comprising the protein of claim 23 and a acceptable carrier.

37. The composition of claim 36, wherein the composition further comprises a liposome.

38. A protein produced by a method comprising:
(a) expressing the protein of claim 23 by a cell; and
(b) recovering the protein.

39. An isolated protein possessing anti-viral activity, comprising a polypeptide having an amino acid sequence at least 90% or more identical to an amino acid sequence selected from the group consisting of:
(a) the amino acid sequence of the full-length polypeptide encoded by the cDNA contained in ATCC Deposit No. 203500; and
(b) the amino acid sequence of the full-length polypeptide encoded by the cDNA contained in ATCC Deposit No. 203500 excluding the N-terminal methionine residue.

40. The isolated protein of claim 39, which comprises a polypeptide having an amino acid sequence at least 90% or more identical to the amino acid sequence of the full-length polypeptide encoded by the cDNA contained in ATCC Deposit No. 203500.

41. The isolated protein of claim 39, which comprises a polypeptide having an amino acid sequence at least 95% or more identical to the amino acid sequence of the full-length polypeptide encoded by the cDNA contained in ATCC Deposit No. 203500.

42. The isolated protein of claim 39, which comprises a polypeptide having an amino acid sequence at least 90% or more identical to the amino acid sequence of the full-length polypeptide encoded by the cDNA contained in ATCC Deposit No. 203500 excluding the N-terminal methionine residue.

43. The isolated protein of claim 39, which comprises a polypeptide having an amino acid sequence at least 95% or more identical to the amino acid sequence of the full-length polypeptide encoded by the cDNA contained in ATCC Deposit No. 203500 excluding the N-terminal methionine residue.

44. The isolated protein of claim 39, wherein the polypeptide further comprises a heterologous polypeptide sequence.

45. The isolated protein of claim 44, wherein the heterologous polypeptide sequence is the Fc domain of an immunoglobulin.

46. The protein of claim 39, wherein said protein is glycosylated.

47. The protein of claim 39, wherein said protein is pegylated.

48. A composition comprising the protein of claim 39 and a acceptable carrier.

49. The composition of claim 48, wherein the composition further comprises a liposome.

50. A protein produced by a method comprising:
(a) expressing the protein of claim 39 by a cell; and
(b) recovering the protein.

51. An isolated protein comprising a polypeptide having an amino acid sequence selected from the group consisting of:
(a) the amino acid sequence of a fragment of amino acid residues 1 to 207 of SEQ ID NO:2, wherein the fragment has anti-viral activity;
(b) the amino acid sequence of a fragment of amino acid residues 1 to 207 of SEQ ID NO:2, wherein the fragment inhibits bone marrow proliferation;
(c) the amino acid sequence of a fragment of amino acid residues 1 to 207 of SEQ ID NO:2, wherein the fragment activates the Jak/Stat pathway; and
(d) the amino acid sequence of a fragment of amino acid residues 1 to 207 of SEQ ID NO:2, wherein the fragment binds an antibody that specifically binds a protein having the amino acid sequence of SEQ ID NO:2.

52. The isolated protein of claim 51, wherein said amino acid sequence is (a).

53. The isolated protein of claim 51, wherein said amino acid sequence is (b).

54. The isolated protein of claim 51, wherein said amino acid sequence is (c).

55. The isolated protein of claim 51, wherein said amino acid sequence is (d).

56. The isolated protein of claim 51, wherein the polypeptide further comprises a heterologous polypeptide sequence.

57. The isolated protein of claim 56, wherein the heterologous polypeptide sequence is the Fc domain of an immunoglobulin.

58. The protein of claim 51, wherein said protein is glycosylated.

59. The protein of claim 51, wherein said protein is pegylated.

60. A composition comprising the protein of claim 51 and a acceptable carrier.

61. The composition of claim 60, wherein the composition further comprises a liposome.

62. A protein produced by a method comprising:
(a) expressing the protein of claim 51 by a cell; and
(b) recovering the protein.

63. An isolated protein comprising a polypeptide having an amino acid sequence selected from the group consisting of:
(a) the amino acid sequence of a fragment of the full-length polypeptide encoded by the cDNA contained in ATCC Deposit No. 203500, wherein the fragment has anti-viral activity;
(b) the amino acid sequence of a fragment of the full-length polypeptide encoded by the cDNA contained in ATCC Deposit No. 203500, wherein the fragment inhibits bone marrow proliferation;
(c) the amino acid sequence of a fragment of the full-length polypeptide encoded by the cDNA contained in ATCC Deposit No. 203500, wherein the fragment activates the Jak/Stat pathway; and
(d) the amino acid sequence of a fragment of the full-length polypeptide encoded by the cDNA contained in ATCC Deposit No. 203500, wherein the fragment binds an antibody that specifically binds a protein having the amino acid sequence of SEQ ID NO:2.

64. The isolated protein of claim 63, wherein said amino acid sequence is (a).

65. The isolated protein of claim 63, wherein said amino acid sequence is (b).

66. The isolated protein of claim 63, wherein said amino acid sequence is (c).

67. The isolated protein of claim 63, wherein said amino acid sequence is (d).

68. The isolated protein of claim 63, wherein the protein further comprises a heterologous polypeptide sequence.

69. The isolated protein of claim 68, wherein the heterologous polypeptide sequence is the Fc domain of an immunoglobulin.

70. The protein of claim 63, wherein said protein is glycosylated.

71. The protein of claim 63, wherein said protein is pegylated.

72. A composition comprising the protein of claim 63 and a acceptable carrier.

73. The composition of claim 72, wherein the composition further comprises a liposome.

74. A protein produced by a method comprising:
(a) expressing the protein of claim 63 by a cell; and
(b) recovering the protein.

75. An isolated protein consisting of at least 30 contiguous amino acid residues of SEQ ID NO:2.

76. The isolated protein of claim 75, wherein the isolated protein consists of at least 50 contiguous amino acid residues of SEQ ID NO:2.

77. The isolated protein of claim 75, wherein the polypeptide further comprises a heterologous polypeptide sequence.

78. The isolated protein of claim 77, wherein the heterologous polypeptide sequence is the Fc domain of an immunoglobulin.

79. The protein of claim 75, wherein said protein is glycosylated.

80. The protein of claim 75, wherein said protein is pegylated.

81. A composition comprising the protein of claim 75 and a acceptable carrier.

82. The composition of claim 81, wherein the composition further comprises a liposome.

83. A protein produced by a method comprising:
(a) expressing the protein of claim 75 by a cell; and
(b) recovering the protein.

84. An isolated protein consisting of at least 30 contiguous amino acid residues of the full-length polypeptide encoded by the cDNA contained in ATCC Deposit No. 203500.

85. The isolated protein of claim 84, wherein the isolated protein consists of at least 50 contiguous amino acid residues of the full-length polypeptide encoded by the cDNA contained in ATCC Deposit No. 203500.

86. The isolated protein of claim 84, wherein the polypeptide further comprises a heterologous polypeptide sequence.

87. The isolated protein of claim 86, wherein the heterologous polypeptide sequence is the Fc domain of an immunoglobulin.

88. The protein of claim 84, wherein said protein is glycosylated.

89. The protein of claim 84, wherein said protein is pegylated.

90. A composition comprising the protein of claim 84 and a acceptable carrier.

91. The composition of claim 90, wherein the composition further comprises a liposome.

92. A protein produced by a method comprising:
(a) expressing the protein of claim 84 by a cell; and
(b) recovering the protein.

* * * * *

UNITED STATES PATENT AND TRADEMARK OFFICE
CERTIFICATE OF CORRECTION

PATENT NO. : 6,433,145 B1
DATED : August 13, 2002
INVENTOR(S) : LaFleur et al.

It is certified that error appears in the above-identified patent and that said Letters Patent is hereby corrected as shown below:

Title page,
Item [60], Related U.S. Application Data, insert -- , filed on July 21, 1998. -- after Provisional application No. 60/093,643.

Column 1,
Line 7, replace "IPCT/US99/16424" with -- PCT/US99/16424 --.
Lines 11-12, replace "filed July, 1998" with -- filed July 21, 1998 --.

Signed and Sealed this

Fifteenth Day of July, 2003

JAMES E. ROGAN
*Director of the United States Patent and Trademark Office*

SEQUENCE LISTING

<160> NUMBER OF SEQ ID NOS: 54

<210> SEQ ID NO 1
<211> LENGTH: 1170
<212> TYPE: DNA
<213> ORGANISM: Homo sapiens
<220> FEATURE:
<221> NAME/KEY: CDS
<222> LOCATION: (35)..(655)

<400> SEQUENCE: 1

| | | | | | | |
|---|---|---|---|---|---|---|
| ccacgcgtcc gggatttttt agcttgcaaa aaaa atg agc acc aaa cct gat atg | | | | | | 55 |
| | | Met Ser Thr Lys Pro Asp Met | | | | |
| | | 1 5 | | | | |
| att caa aag tgt ttg tgg ctt gag atc ctt atg ggt ata ttc att gct | | | | | | 103 |
| Ile Gln Lys Cys Leu Trp Leu Glu Ile Leu Met Gly Ile Phe Ile Ala | | | | | | |
| 10 15 20 | | | | | | |
| ggc acc cta tcc ctg gac tgt aac tta ctg aac gtt cac ctg aga aga | | | | | | 151 |
| Gly Thr Leu Ser Leu Asp Cys Asn Leu Leu Asn Val His Leu Arg Arg | | | | | | |
| 25 30 35 | | | | | | |
| gtc acc tgg caa aat ctg aga cat ctg agt agt atg agc aat tca ttt | | | | | | 199 |
| Val Thr Trp Gln Asn Leu Arg His Leu Ser Ser Met Ser Asn Ser Phe | | | | | | |
| 40 45 50 55 | | | | | | |
| cct gta gaa tgt cta cga gaa aac ata gct ttt gag ttg ccc caa gag | | | | | | 247 |
| Pro Val Glu Cys Leu Arg Glu Asn Ile Ala Phe Glu Leu Pro Gln Glu | | | | | | |
| 60 65 70 | | | | | | |
| ttt ctg caa tac acc caa cct atg aag agg gac atc aag aag gcc ttc | | | | | | 295 |
| Phe Leu Gln Tyr Thr Gln Pro Met Lys Arg Asp Ile Lys Lys Ala Phe | | | | | | |
| 75 80 85 | | | | | | |
| tat gaa atg tcc cta cag gcc ttc aac atc ttc agc caa cac acc ttc | | | | | | 343 |
| Tyr Glu Met Ser Leu Gln Ala Phe Asn Ile Phe Ser Gln His Thr Phe | | | | | | |
| 90 95 100 | | | | | | |
| aaa tat tgg aaa gag aga cac ctc aaa caa atc caa ata gga ctt gat | | | | | | 391 |
| Lys Tyr Trp Lys Glu Arg His Leu Lys Gln Ile Gln Ile Gly Leu Asp | | | | | | |
| 105 110 115 | | | | | | |
| cag caa gca gag tac ctg aac caa tgc ttg gag gaa gac gag aat gaa | | | | | | 439 |
| Gln Gln Ala Glu Tyr Leu Asn Gln Cys Leu Glu Glu Asp Glu Asn Glu | | | | | | |
| 120 125 130 135 | | | | | | |
| aat gaa gac atg aaa gaa atg aaa gag aat gag atg aaa ccc tca gaa | | | | | | 487 |
| Asn Glu Asp Met Lys Glu Met Lys Glu Asn Glu Met Lys Pro Ser Glu | | | | | | |
| 140 145 150 | | | | | | |
| gcc agg gtc ccc cag ctg agc agc ctg gaa ctg agg aga tat ttc cac | | | | | | 535 |
| Ala Arg Val Pro Gln Leu Ser Ser Leu Glu Leu Arg Arg Tyr Phe His | | | | | | |
| 155 160 165 | | | | | | |
| agg ata gac aat ttc ctg aaa gaa aag aaa tac agt gac tgt gcc tgg | | | | | | 583 |
| Arg Ile Asp Asn Phe Leu Lys Glu Lys Lys Tyr Ser Asp Cys Ala Trp | | | | | | |
| 170 175 180 | | | | | | |
| gag att gtc cga gtg gaa atc aga aga tgt ttg tat tac ttt tac aaa | | | | | | 631 |
| Glu Ile Val Arg Val Glu Ile Arg Arg Cys Leu Tyr Tyr Phe Tyr Lys | | | | | | |
| 185 190 195 | | | | | | |
| ttt aca gct cta ttc agg agg aaa taagaatcat ctaccttcaa gcaagaatta | | | | | | 685 |
| Phe Thr Ala Leu Phe Arg Arg Lys | | | | | | |
| 200 205 | | | | | | |
| acagagattg tggctacgca aatgcaccaa aaaagggtga aatatatctg aaatgtacct | | | | | | 745 |
| ggttctgccc ttggaagcca cttcctgctc atgccactaa cagcatgctg ccaaactgtt | | | | | | 805 |
| cagattcaag attattccaa gcgcagggcc caaatgttat agccaaagaa agtcttatga | | | | | | 865 |
| taaaagtgag gcaaatttca gccaagaagt tagaagagat gtttaaaaga acaagaacaa | | | | | | 925 |

-continued

```
attgtggatc atggtatatg caggctatca gcagaaggat cagacaataa aatgagttag      985
tgcaaaccat ttagtaaaaa taactatcag cagagttgtt ccagattaaa aatagtacta     1045
caagcttgta aaggagttag gacatgcaag ctactgagca taaaatatat acttgctatt     1105
tttcatgact ttctctaata aagtctttga ctgttctctc taataaaaaa aaaaaaaaaa     1165
aaaaa                                                                 1170
```

<210> SEQ ID NO 2
<211> LENGTH: 207
<212> TYPE: PRT
<213> ORGANISM: Homo sapiens

<400> SEQUENCE: 2

```
Met Ser Thr Lys Pro Asp Met Ile Gln Lys Cys Leu Trp Leu Glu Ile
 1               5                  10                  15

Leu Met Gly Ile Phe Ile Ala Gly Thr Leu Ser Leu Asp Cys Asn Leu
             20                  25                  30

Leu Asn Val His Leu Arg Arg Val Thr Trp Gln Asn Leu Arg His Leu
         35                  40                  45

Ser Ser Met Ser Asn Ser Phe Pro Val Glu Cys Leu Arg Glu Asn Ile
     50                  55                  60

Ala Phe Glu Leu Pro Gln Glu Phe Leu Gln Tyr Thr Gln Pro Met Lys
 65                  70                  75                  80

Arg Asp Ile Lys Lys Ala Phe Tyr Glu Met Ser Leu Gln Ala Phe Asn
                 85                  90                  95

Ile Phe Ser Gln His Thr Phe Lys Tyr Trp Lys Glu Arg His Leu Lys
            100                 105                 110

Gln Ile Gln Ile Gly Leu Asp Gln Gln Ala Glu Tyr Leu Asn Gln Cys
        115                 120                 125

Leu Glu Glu Asp Glu Asn Glu Asn Glu Asp Met Lys Glu Met Lys Glu
    130                 135                 140

Asn Glu Met Lys Pro Ser Glu Ala Arg Val Pro Gln Leu Ser Ser Leu
145                 150                 155                 160

Glu Leu Arg Arg Tyr Phe His Arg Ile Asp Asn Phe Leu Lys Glu Lys
                165                 170                 175

Lys Tyr Ser Asp Cys Ala Trp Glu Ile Val Arg Val Glu Ile Arg Arg
            180                 185                 190

Cys Leu Tyr Tyr Phe Tyr Lys Phe Thr Ala Leu Phe Arg Arg Lys
        195                 200                 205
```

<210> SEQ ID NO 3
<211> LENGTH: 238
<212> TYPE: PRT
<213> ORGANISM: Homo sapiens

<400> SEQUENCE: 3

```
Met Ala Leu Leu Phe Pro Leu Leu Ala Ala Leu Val Met Thr Ser Tyr
 1               5                  10                  15

Ser Pro Val Gly Ser Leu Gly Cys Asp Leu Pro Gln Asn His Gly Leu
             20                  25                  30

Leu Ser Arg Asn Thr Leu Val Leu Leu His Gln Met Arg Arg Ile Ser
         35                  40                  45

Pro Phe Leu Cys Leu Lys Asp Arg Arg Asp Phe Arg Phe Pro Gln Glu
     50                  55                  60

Met Val Lys Gly Ser Gln Leu Gln Lys Ala His Val Met Ser Val Leu
 65                  70                  75                  80
```

```
His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Glu Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Val Pro Gln Leu Ser Ser
    130                 135                 140

Leu Glu Leu Arg Arg Tyr Phe His Arg Ile Asp Asn Phe Leu Lys Glu
145                 150                 155                 160

Lys Lys Tyr Ser Asp Cys Ala Trp Glu Ile Val Arg Val Glu Ile Arg
                165                 170                 175

Arg Cys Leu Tyr Tyr Phe Tyr Lys Phe Thr Ala Leu Pro Ala Leu Thr
            180                 185                 190

Leu Arg Arg Tyr Phe Gln Gly Ile Arg Val Tyr Leu Lys Glu Lys Lys
        195                 200                 205

Tyr Ser Asp Cys Ala Trp Glu Val Val Arg Met Glu Ile Met Lys Ser
    210                 215                 220

Leu Phe Leu Ser Thr Asn Met Gln Glu Arg Leu Arg Ser Lys
225                 230                 235

<210> SEQ ID NO 4
<211> LENGTH: 187
<212> TYPE: PRT
<213> ORGANISM: Homo sapiens

<400> SEQUENCE: 4

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 5
<211> LENGTH: 194
<212> TYPE: PRT
```

-continued

```
<213> ORGANISM: Homo sapiens

<400> SEQUENCE: 5

Met Ala Phe Val Leu Ser Leu Leu Met Ala Leu Val Leu Val Ser Tyr
  1               5                  10                  15

Gly Pro Phe Gly Ser Leu Gly Cys Asp Leu Ser Gln Asn His Val Leu
             20                  25                  30

Val Gly Arg Lys Asn Leu Arg Leu Leu Asp Glu Met Arg Arg Leu Ser
         35                  40                  45

Pro His Phe Cys Leu Gln Asp Arg Lys Asp Phe Ala Leu Pro Gln Glu
     50                  55                  60

Met Val Glu Gly Gly Gln Leu Gln Glu Ala Gln Ala Ile Ser Val Leu
 65                  70                  75                  80

His Glu Met Leu Gln Gln Ser Phe Asn Leu Phe His Thr Glu His Ser
                 85                  90                  95

Ser Ala Ala Trp Asp Thr Thr Leu Leu Glu Pro Cys Arg Thr Gly Leu
            100                 105                 110

His Gln Gln Leu Asp Asn Leu Asp Ala Cys Leu Gly Gln Val Met Gly
        115                 120                 125

Glu Glu Asp Ser Ala Leu Gly Arg Thr Gly Pro Leu Ala Leu Lys Arg
    130                 135                 140

Tyr Phe Gln Gly Ile His Val Tyr Leu Lys Glu Lys Gly Tyr Ser Asp
145                 150                 155                 160

Cys Ala Trp Glu Thr Val Arg Leu Glu Ile Met Arg Ser Phe Ser Ser
                165                 170                 175

Leu Ile Ser Leu Gln Glu Arg Leu Arg Met Met Asp Gly Asp Leu Ser
            180                 185                 190

Ser Pro

<210> SEQ ID NO 6
<211> LENGTH: 245
<212> TYPE: PRT
<213> ORGANISM: Homo sapiens

<400> SEQUENCE: 6

Met Ala Leu Leu Phe Pro Leu Leu Ala Ala Leu Val Met Thr Ser Tyr
  1               5                  10                  15

Ser Pro Val Gly Ser Leu Gly Cys Asp Leu Pro Gln Asn His Gly Leu
             20                  25                  30

Leu Ser Arg Asn Thr Leu Val Leu Leu His Gln Met Arg Arg Ile Ser
         35                  40                  45

Pro Phe Leu Cys Leu Lys Asp Arg Arg Asp Phe Arg Phe Pro Gln Glu
     50                  55                  60

Met Val Lys Gly Ser Gln Leu Gln Lys Ala His Val Met Ser Val Leu
 65                  70                  75                  80

His Glu Met Leu Gln Gln Ile Phe Ser Leu Phe His Thr Glu Arg Ser
                 85                  90                  95

Ser Ala Ala Trp Asn Met Thr Leu Leu Asp Gln Leu His Thr Glu Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Val Pro Gln Leu Ser Ser
    130                 135                 140

Leu Glu Leu Arg Arg Tyr Phe His Arg Ile Asp Asn Phe Leu Lys Glu
145                 150                 155                 160
```

```
Lys Lys Tyr Ser Asp Cys Ala Trp Glu Ile Val Arg Val Glu Ile Arg
                165                 170                 175

Arg Cys Leu Tyr Tyr Phe Tyr Lys Phe Thr Ala Leu Pro Ala Leu Thr
            180                 185                 190

Leu Arg Arg Tyr Phe Gln Gly Ile Arg Val Tyr Leu Lys Glu Lys Lys
        195                 200                 205

Tyr Ser Asp Cys Ala Trp Glu Val Val Arg Met Glu Ile Met Lys Ser
    210                 215                 220

Leu Phe Leu Ser Thr Asn Met Gln Glu Arg Leu Arg Ser Lys Asp Arg
225                 230                 235                 240

Asp Leu Gly Ser Ser
                245

<210> SEQ ID NO 7
<211> LENGTH: 189
<212> TYPE: PRT
<213> ORGANISM: Homo sapiens

<400> SEQUENCE: 7

Met Ala Leu Ser Phe Ser Leu Leu Met Ala Val Leu Val Leu Ser Tyr
  1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Gly Gln Met Gly Arg Ile Ser
         35                  40                  45

Pro Phe Ser Cys Leu Lys Asp Arg His Asp Phe Arg Ile Pro Gln Glu
     50                  55                  60

Glu Phe Asp Gly Asn Gln Phe Gln Asp Ala Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 8
<211> LENGTH: 189
<212> TYPE: PRT
<213> ORGANISM: Homo sapiens

<400> SEQUENCE: 8

Met Ala Leu Ser Phe Ser Leu Leu Met Ala Val Leu Val Leu Ser Tyr
  1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Ala Gln Met Gly Arg Ile Ser
         35                  40                  45
```

```
Pro Phe Ser Cys Leu Lys Asp Arg His Asp Phe Gly Phe Pro Gln Glu
        50                  55                  60

Glu Phe Asp Gly Asn Gln Phe Gln Lys Ala His Val Met Ser Val Leu
 65                  70                  75                  80

His Glu Met Leu Gln Gln Ile Phe Ser Leu Phe His Thr Glu Arg Ser
                 85                  90                  95

Ser Ala Ala Trp Glu Gln Ser Leu Leu Glu Lys Phe Ser Thr Glu Leu
            100                 105                 110

Asn Gln Gln Leu Asn Asp Leu Glu Ala Cys Val Ile Gln Glu Val Gly
        115                 120                 125

Val Glu Glu Thr Pro Leu Met Asn Val Asp Ser Ile Leu Ala Val Lys
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Lys Ile Phe Gln Glu Arg Leu Arg Arg Lys Glu
            180                 185

<210> SEQ ID NO 9
<211> LENGTH: 195
<212> TYPE: PRT
<213> ORGANISM: Homo sapiens

<400> SEQUENCE: 9

Met Ala Leu Leu Phe Pro Leu Leu Ala Ala Leu Val Met Thr Ser Tyr
 1               5                  10                  15

Ser Pro Val Gly Ser Leu Gly Cys Asp Leu Pro Gln Asn His Gly Leu
                 20                  25                  30

Leu Ser Arg Asn Thr Leu Val Leu Leu His Gln Met Arg Arg Ile Ser
            35                  40                  45

Pro Phe Leu Cys Leu Lys Asp Arg Arg Asp Phe Arg Phe Pro Gln Glu
        50                  55                  60

Met Val Lys Gly Ser Gln Leu Gln Lys Ala His Val Met Ser Val Leu
 65                  70                  75                  80

His Glu Met Leu Gln Gln Ile Phe Ser Leu Phe His Thr Glu Arg Ser
                 85                  90                  95

Ser Ala Ala Trp Asn Met Thr Leu Leu Asp Gln Leu His Thr Glu Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
            180                 185                 190

Gly Ser Ser
        195

<210> SEQ ID NO 10
<211> LENGTH: 189
<212> TYPE: PRT
```

-continued

<213> ORGANISM: Homo sapiens

<400> SEQUENCE: 10

Met Pro Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Trp Ile Leu Leu Ala Gln Met Gly Arg Ile Ser
        35                  40                  45

His Phe Ser Cys Leu Lys Asp Arg Tyr Asp Phe Gly Phe Pro Gln Glu
    50                  55                  60

Val Phe Asp Gly Asn Gln Phe Gln Lys Ala Gln Ala Ile Ser Ala Phe
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Thr Gln Glu Val Gly
        115                 120                 125

Val Glu Glu Ile Ala Leu Met Asn Glu Asp Ser Ile Leu Ala Val Arg
130                 135                 140

Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
            180                 185

<210> SEQ ID NO 11
<211> LENGTH: 195
<212> TYPE: PRT
<213> ORGANISM: Homo sapiens

<400> SEQUENCE: 11

Met Ala Phe Val Leu Ser Leu Leu Met Ala Leu Val Leu Val Ser Tyr
1               5                   10                  15

Gly Pro Gly Arg Ser Leu Gly Cys Tyr Leu Ser Glu Asp His Met Leu
            20                  25                  30

Gly Ala Arg Glu Asn Leu Arg Leu Leu Ala Arg Met Asn Arg Leu Ser
        35                  40                  45

Pro His Pro Cys Leu Gln Asp Arg Lys Asp Phe Gly Leu Pro Gln Glu
    50                  55                  60

Met Val Glu Gly Asn Gln Leu Gln Lys Asp Gln Ala Ile Ser Val Leu
65                  70                  75                  80

His Glu Met Leu Gln Gln Cys Phe Asn Leu Phe Tyr Thr Glu His Ser
                85                  90                  95

Ser Ala Ala Trp Asn Thr Thr Leu Leu Glu Gln Leu Cys Thr Gly Leu
            100                 105                 110

Gln Gln Gln Leu Glu Asp Leu Asp Ala Cys Leu Gly Pro Val Met Gly
        115                 120                 125

Glu Lys Asp Ser Asp Met Gly Arg Met Gly Pro Ile Leu Thr Val Lys
    130                 135                 140

Lys Tyr Phe Gln Gly Ile His Val Tyr Leu Lys Glu Lys Glu Tyr Ser
145                 150                 155                 160

Asp Cys Ala Trp Glu Ile Ile Arg Met Glu Met Met Arg Ala Leu Ser

```
                         165                 170                 175
Ser Ser Thr Thr Leu Gln Lys Arg Leu Arg Lys Met Gly Gly Asp Leu
            180                 185                 190

Asn Ser Leu
        195

<210> SEQ ID NO 12
<211> LENGTH: 196
<212> TYPE: PRT
<213> ORGANISM: Homo sapiens

<400> SEQUENCE: 12

Met Ala Phe Val Leu Ser Leu Leu Met Ala Leu Val Leu Val Ser Tyr
 1               5                  10                  15

Gly Pro Gly Gly Ser Leu Gly Cys Tyr Leu Ser Gln Arg Leu Met Leu
            20                  25                  30

Asp Ala Arg Glu Asn Leu Lys Leu Leu Glu Pro Met Asn Arg Leu Ser
        35                  40                  45

Pro His Ser Cys Leu Gln Asp Arg Lys Asp Phe Gly Leu Pro Gln Glu
    50                  55                  60

Met Val Glu Gly Asp Gln Leu Gln Lys Asp Gln Ala Phe Pro Val Leu
65                  70                  75                  80

Tyr Glu Met Leu Gln Gln Thr Phe Asn Leu Phe His Thr Glu His Ser
                85                  90                  95

Ser Ala Ala Trp Asp Thr Thr Leu Leu Glu Gln Leu Cys Thr Gly Leu
            100                 105                 110

Gln Gln Gln Leu Glu Asp Leu Asp Thr Cys Cys Arg Gly Gln Val Met
        115                 120                 125

Gly Glu Glu Asp Ser Glu Leu Gly Asn Met Asp Pro Ile Val Thr Val
    130                 135                 140

Lys Lys Tyr Phe Gln Gly Ile Tyr Asp Tyr Leu Gln Glu Lys Gly Tyr
145                 150                 155                 160

Ser Asp Cys Ala Trp Glu Ile Val Arg Val Glu Met Met Arg Ala Leu
                165                 170                 175

Thr Val Ser Thr Thr Leu Gln Lys Arg Leu Thr Lys Met Gly Gly Asp
            180                 185                 190

Leu Asn Ser Pro
        195

<210> SEQ ID NO 13
<211> LENGTH: 170
<212> TYPE: PRT
<213> ORGANISM: Homo sapiens

<400> SEQUENCE: 13

Met Ala Gln Ile Tyr Leu Val Met Ala Gly Val Met Leu Cys Ser Ile
 1               5                  10                  15

Ser Val Cys Phe Leu Asp Gln Asn Leu Ser Ala Val His Cys Val Glu
            20                  25                  30

Lys Arg Glu Ile Phe Lys His Leu Gln Glu Ile Lys Lys Ile Pro Ser
        35                  40                  45

Gln Leu Cys Leu Lys Asp Arg Ile Asp Phe Lys Phe Pro Trp Lys Arg
    50                  55                  60

Glu Ser Ile Thr Gln Leu Gln Lys Asp Gln Ala Phe Pro Val Leu Tyr
65                  70                  75                  80

Glu Met Leu Gln Gln Thr Phe Asn Leu Phe His Thr Glu His Ser Ser
```

```
                    85                  90                  95
Ala Ala Trp Asn Thr Thr Leu Leu Asp Gln Leu Leu Ser Ser Leu Asp
                100                 105                 110

Leu Gly Leu Arg Arg Leu Glu His Met Lys Lys Asp Asn Met Asp Cys
            115                 120                 125

Pro His Val Gly Ser Ala Leu Arg Lys Tyr Phe Gln Gly Ile Gly Leu
        130                 135                 140

Tyr Leu Lys Glu Lys Lys Tyr Ser Pro Cys Ala Trp Glu Ile Val Arg
145                 150                 155                 160

Val Glu Ile Glu Arg Cys Phe Ser Leu Thr
                165                 170

<210> SEQ ID NO 14
<211> LENGTH: 212
<212> TYPE: PRT
<213> ORGANISM: Homo sapiens

<400> SEQUENCE: 14

Met Asn Ser Phe Ser Thr Ser Ala Phe Gly Pro Val Ala Phe Ser Leu
  1               5                  10                  15

Gly Leu Leu Leu Val Leu Pro Ala Ala Phe Pro Ala Pro Val Pro Pro
                 20                  25                  30

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
         50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Lys Glu Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
        210

<210> SEQ ID NO 15
<211> LENGTH: 186
<212> TYPE: PRT
<213> ORGANISM: Homo sapiens

<400> SEQUENCE: 15

Met Thr His Arg Cys Leu Leu Gln Met Val Leu Leu Cys Phe Ser
  1               5                  10                  15

Thr Thr Ala Leu Ser Arg Ser Tyr Ser Leu Leu Arg Phe Gln Gln Arg
```

```
                    20                  25                  30
Arg Ser Leu Ala Leu Cys Gln Lys Leu Leu Arg Gln Leu Pro Ser Thr
            35                  40                  45
Pro Gln His Cys Leu Glu Ala Arg Met Asp Phe Gln Met Pro Glu Glu
        50                  55                  60
Met Lys Gln Ala Gln Gln Phe Gln Lys Glu Asp Ala Ile Leu Val Ile
65                  70                  75                  80
Tyr Glu Met Leu Gln Gln Ile Phe Asn Ile Leu Thr Arg Asp Phe Ser
                85                  90                  95
Ser Thr Gly Trp Ser Glu Thr Ile Ile Glu Asp Leu Leu Glu Leu
            100                 105                 110
Tyr Glu Gln Met Asn His Leu Glu Pro Ile Gln Lys Glu Ile Met Gln
            115                 120                 125
Lys Gln Asn Ser Thr Met Gly Asp Thr Thr Val Leu His Leu Arg Lys
        130                 135                 140
Tyr Tyr Phe Asn Leu Val Gln Tyr Leu Lys Ser Lys Glu Tyr Asn Arg
145                 150                 155                 160
Cys Ala Trp Thr Val Val Arg Val Gln Ile Leu Arg Asn Phe Ser Phe
                165                 170                 175
Leu Thr Arg Leu Thr Gly Tyr Leu Arg Glu
            180                 185
```

```
<210> SEQ ID NO 16
<211> LENGTH: 29
<212> TYPE: DNA
<213> ORGANISM: Homo sapiens

<400> SEQUENCE: 16
ggccgcatat gctggactgt aacttactg                                    29

<210> SEQ ID NO 17
<211> LENGTH: 33
<212> TYPE: DNA
<213> ORGANISM: Homo sapiens

<400> SEQUENCE: 17
ggccgcggta ccttatttcc tcctgaatag agc                               33

<210> SEQ ID NO 18
<211> LENGTH: 38
<212> TYPE: DNA
<213> ORGANISM: Homo sapiens

<400> SEQUENCE: 18
ggccgggatc cgccatcatg agcaccaaac ctgatatg                          38

<210> SEQ ID NO 19
<211> LENGTH: 33
<212> TYPE: DNA
<213> ORGANISM: Homo sapiens

<400> SEQUENCE: 19
ggccgcggta ccttatttcc tcctgaatag agc                               33

<210> SEQ ID NO 20
<211> LENGTH: 156
<212> TYPE: PRT
<213> ORGANISM: Homo sapiens

<400> SEQUENCE: 20
```

```
Met Thr Tyr Arg Cys Leu Leu Gln Met Val Leu Leu Cys Phe Ser
 1               5                  10                  15

Thr Thr Ala Leu Ser Arg Ser Tyr Ser Leu Leu Arg Phe Gln Gln Arg
             20                  25                  30

Gln Ser Leu Lys Glu Cys Gln Lys Leu Leu Gly Gln Leu Pro Ser Thr
             35                  40                  45

Ser Gln His Cys Leu Glu Ala Arg Met Asp Phe Gln Met Pro Glu Glu
             50                  55                  60

Met Lys Gln Glu Gln Gln Phe Gln Lys Glu Asp Ala Ile Leu Val Met
 65                  70                  75                  80

Tyr Glu Val Leu Gln His Ile Phe Gly Ile Leu Thr Arg Asp Phe Ser
                 85                  90                  95

Ser Thr Gly Trp Asn Ser Thr Thr Glu Asp Thr Ile Val Pro His Leu
                100                 105                 110

Gly Lys Tyr Tyr Phe Asn Leu Met Gln Tyr Leu Glu Ser Lys Glu Tyr
                115                 120                 125

Asp Arg Cys Ala Trp Thr Val Val Gln Val Gln Ile Leu Thr Asn Val
            130                 135                 140

Ser Phe Leu Met Arg Leu Thr Gly Tyr Val Arg Asp
145                 150                 155
```

```
<210> SEQ ID NO 21
<211> LENGTH: 166
<212> TYPE: PRT
<213> ORGANISM: Homo sapiens

<400> SEQUENCE: 21
```

```
Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
             35                  40                  45

Gln Phe Gln Lys Glu Asp Ala Ala Leu Thr Ile Tyr Glu Met Leu Gln
             50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Gly Asn
                165
```

```
<210> SEQ ID NO 22
<211> LENGTH: 540
<212> TYPE: DNA
<213> ORGANISM: Homo sapiens

<400> SEQUENCE: 22
```

```
ctggattgca acctgctgaa cgttcatctg cgtcgcgtga cctggcagaa cctgcgtcac    60
ctgagctcta tgagcaactc cttcccggtt gagtgcctgc gtgaaaacat cgcgtttgaa   120
ctgccgcaag aattcctgca atacacccag ccgatgaaac gtgatatcaa gaaagcgttc   180
tacgaaatgt ccctgcaggc gttcaacatc ttcagccagc acaccttcaa atactggaaa   240
gaacgtcacc tgaaacagat ccagatcggt ctggatcagc aagcagaata cctgaaccag   300
tgcctggaag aagacgagaa cgaaaacgaa gacatgaaag aaatgaaaga gaacgaaatg   360
aaaccgtctg aagcgcgtgt tccgcagctg agctctctgg aactgcgccg ttacttccac   420
cgcatcgaca acttcctgaa agaaaagaaa tactctgact gcgcgtggga atcgtgcgt   480 gtggaaatcc gccgttgtct gtactacttc tacaaattca ccgctctgtt ccgtcgcaaa   540
```

<210> SEQ ID NO 23
<211> LENGTH: 31
<212> TYPE: DNA
<213> ORGANISM: Homo sapiens

<400> SEQUENCE: 23

```
ggcctgggat cccctggact gtaacttact g                                   31
```

<210> SEQ ID NO 24
<211> LENGTH: 33
<212> TYPE: DNA
<213> ORGANISM: Homo sapiens

<400> SEQUENCE: 24

```
cgcgcggtac cttattattt cctcctgaat aga                                 33
```

<210> SEQ ID NO 25
<211> LENGTH: 86
<212> TYPE: DNA
<213> ORGANISM: Homo sapiens

<400> SEQUENCE: 25

```
gcgcctcgag atttccccga aatctagatt tccccgaaat gatttccccg aaatgatttc    60
cccgaaatat ctgccatctc aattag                                         86
```

<210> SEQ ID NO 26
<211> LENGTH: 27
<212> TYPE: DNA
<213> ORGANISM: Homo sapiens

<400> SEQUENCE: 26

```
gcggcaagct ttttgcaaag cctaggc                                        27
```

<210> SEQ ID NO 27
<211> LENGTH: 271
<212> TYPE: DNA
<213> ORGANISM: Homo sapiens

<400> SEQUENCE: 27

```
ctcgagattt ccccgaaatc tagatttccc cgaaatgatt ccccgaaat gatttccccg    60 aaatatctgc catctcaatt agtcagcaac catagtcccg cccctaactc cgcccatccc   120
gcccctaact ccgcccagtt ccgcccattc tccgcccat ggctgactaa ttttttttat    180
ttatgcagag gccgaggccg cctcggcctc tgagctattc cagaagtagt gaggaggctt   240
ttttggaggc ctaggctttt gcaaaaagct t                                  271
```

```
<210> SEQ ID NO 28
<211> LENGTH: 32
<212> TYPE: DNA
<213> ORGANISM: Homo sapiens

<400> SEQUENCE: 28
gcgctcgagg gatgacagcg atagaacccc gg                              32

<210> SEQ ID NO 29
<211> LENGTH: 31
<212> TYPE: DNA
<213> ORGANISM: Homo sapiens

<400> SEQUENCE: 29
gcgaagcttc gcgactcccc ggatccgcct c                               31

<210> SEQ ID NO 30
<211> LENGTH: 12
<212> TYPE: DNA
<213> ORGANISM: Homo sapiens

<400> SEQUENCE: 30
ggggactttc cc                                                    12

<210> SEQ ID NO 31
<211> LENGTH: 73
<212> TYPE: DNA
<213> ORGANISM: Homo sapiens

<400> SEQUENCE: 31
gcggcctcga ggggactttc ccggggactt tccggggact tccgggact ttccatcctg    60 ccatctcaat tag                                                   73

<210> SEQ ID NO 32
<211> LENGTH: 256
<212> TYPE: DNA
<213> ORGANISM: Homo sapiens

<400> SEQUENCE: 32
ctcgagggga ctttcccggg gactttccgg ggactttccg ggactttcca tctgccatct    60
caattagtca gcaaccatag tcccgcccct aactccgccc atcccgcccc taactccgcc   120
cagttccgcc cattctccgc ccatggctg actaatttt tttatttatg cagaggccga   180
ggccgcctcg gcctctgagc tattccagaa gtagtgagga ggctttttg gaggcctagg   240 cttttgcaaa aagctt                                                256

<210> SEQ ID NO 33
<211> LENGTH: 35
<212> TYPE: DNA
<213> ORGANISM: Homo sapiens

<400> SEQUENCE: 33
gcgcgcggta ccttatcttc tgatttccac tcgga                           35

<210> SEQ ID NO 34
<211> LENGTH: 30
<212> TYPE: DNA
<213> ORGANISM: Homo sapiens

<400> SEQUENCE: 34
caacctatga agagggacat caagaaggcc                                 30
```

<210> SEQ ID NO 35
<211> LENGTH: 22
<212> TYPE: DNA
<213> ORGANISM: Homo sapiens

<400> SEQUENCE: 35
gccccaagag tttctgcaat ac                                    22

<210> SEQ ID NO 36
<211> LENGTH: 23
<212> TYPE: DNA
<213> ORGANISM: Homo sapiens

<400> SEQUENCE: 36
ggcctgtagg gacatttcat aga                                   23

<210> SEQ ID NO 37
<211> LENGTH: 22
<212> TYPE: DNA
<213> ORGANISM: Homo sapiens

<400> SEQUENCE: 37
tgctggcacc agacttgccc tc                                    22

<210> SEQ ID NO 38
<211> LENGTH: 20
<212> TYPE: DNA
<213> ORGANISM: Homo sapiens

<400> SEQUENCE: 38
cggctaccac atccaaggaa                                       20

<210> SEQ ID NO 39
<211> LENGTH: 18
<212> TYPE: DNA
<213> ORGANISM: Homo sapiens

<400> SEQUENCE: 39
gctggaatta ccgcggct                                         18

<210> SEQ ID NO 40
<211> LENGTH: 26
<212> TYPE: DNA
<213> ORGANISM: Homo sapiens

<400> SEQUENCE: 40
aagcttcttg gtcctaacgc cagccc                                26

<210> SEQ ID NO 41
<211> LENGTH: 22
<212> TYPE: DNA
<213> ORGANISM: Homo sapiens

<400> SEQUENCE: 41
tcaatgtgga ccagctgaac at                                    22

<210> SEQ ID NO 42
<211> LENGTH: 20
<212> TYPE: DNA
<213> ORGANISM: Homo sapiens

<400> SEQUENCE: 42

-continued cgtccacgga atgagaccat 20

<210> SEQ ID NO 43
<211> LENGTH: 21
<212> TYPE: DNA
<213> ORGANISM: Homo sapiens

<400> SEQUENCE: 43
ccacggttcc ctgcctggca g 21

<210> SEQ ID NO 44
<211> LENGTH: 21
<212> TYPE: DNA
<213> ORGANISM: Homo sapiens

<400> SEQUENCE: 44
ggatctgctg gaggaaggaa a 21

<210> SEQ ID NO 45
<211> LENGTH: 22
<212> TYPE: DNA
<213> ORGANISM: Homo sapiens

<400> SEQUENCE: 45
gatgagctcg ctggtaagtt tt 22

<210> SEQ ID NO 46
<211> LENGTH: 34
<212> TYPE: DNA
<213> ORGANISM: Homo sapiens

<400> SEQUENCE: 46
tggcagctat aaacctaacc cccaaatcta tgtc 34

<210> SEQ ID NO 47
<211> LENGTH: 20
<212> TYPE: DNA
<213> ORGANISM: Homo sapiens

<400> SEQUENCE: 47
ctttgatgcc ctgggtcagt 20

<210> SEQ ID NO 48
<211> LENGTH: 19
<212> TYPE: DNA
<213> ORGANISM: Homo sapiens

<400> SEQUENCE: 48
tcggtgcact cctcgatga 19

<210> SEQ ID NO 49
<211> LENGTH: 22
<212> TYPE: DNA
<213> ORGANISM: Homo sapiens

<400> SEQUENCE: 49
tggccctcct ggtgctcagc tg 22

<210> SEQ ID NO 50
<211> LENGTH: 22
<212> TYPE: DNA
<213> ORGANISM: Homo sapiens

<400> SEQUENCE: 50

```
tggccttgac ctttgcttta ct                                                    22

<210> SEQ ID NO 51
<211> LENGTH: 19
<212> TYPE: DNA
<213> ORGANISM: Homo sapiens

<400> SEQUENCE: 51
agcccacaga gcagcttga                                                        19

<210> SEQ ID NO 52
<211> LENGTH: 23
<212> TYPE: DNA
<213> ORGANISM: Homo sapiens

<400> SEQUENCE: 52
cagttccaga aggaggacgc cgc                                                   23

<210> SEQ ID NO 53
<211> LENGTH: 23
<212> TYPE: DNA
<213> ORGANISM: Homo sapiens

<400> SEQUENCE: 53
gacatccctg aggagattaa gca                                                   23

<210> SEQ ID NO 54
<211> LENGTH: 24
<212> TYPE: DNA
<213> ORGANISM: Homo sapiens

<400> SEQUENCE: 54
ctggagcatc tcatagatgg tcaa                                                  24
```